United States Patent
Xi et al.

(10) Patent No.: US 9,657,007 B2
(45) Date of Patent: May 23, 2017

(54) SUBSTITUTED AMINOPYRIMIDINE COMPOUNDS AND METHODS OF USE

(71) Applicants: Calitor Sciences, LLC, Newbury Park, CA (US); Sunshine Lake Pharma Co., Ltd., Dongguan, Guangdong (CN)

(72) Inventors: Ning Xi, Newbury Park, CA (US); Liang Wang, Guangdong (CN); Tingjin Wang, Guangdong (CN)

(73) Assignees: CALITOR SCIENCES, LLC, Newbury Park, CA (US); SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 14/488,296

(22) Filed: Sep. 17, 2014

(65) Prior Publication Data

US 2015/0087658 A1   Mar. 26, 2015

Related U.S. Application Data

(60) Provisional application No. 61/880,974, filed on Sep. 22, 2013, provisional application No. 61/983,444, filed on Apr. 23, 2014.

(51) Int. Cl.

| | | |
|---|---|---|
| *A01N 43/54* | (2006.01) | |
| *C07D 239/42* | (2006.01) | |
| *C07D 401/00* | (2006.01) | |
| *C07D 403/00* | (2006.01) | |
| *C07D 413/14* | (2006.01) | |
| *C07D 401/14* | (2006.01) | |
| *A61K 31/517* | (2006.01) | |
| *C07D 403/14* | (2006.01) | |
| *A61K 45/06* | (2006.01) | |

(52) U.S. Cl.
CPC .......... *C07D 413/14* (2013.01); *A61K 31/517* (2013.01); *A61K 45/06* (2013.01); *C07D 401/14* (2013.01); *C07D 403/14* (2013.01)

(58) Field of Classification Search
USPC .......................................... 514/256; 544/328
See application file for complete search history.

(56) References Cited

U.S. PATENT DOCUMENTS

| | | | |
|---|---|---|---|
| 6,518,277 B1 | 2/2003 | Sadhu et al. | |
| 6,800,620 B2 | 10/2004 | Sadhu et al. | |
| 6,949,535 B2 | 9/2005 | Sadhu et al. | |
| 7,932,260 B2 | 4/2011 | Fowler et al. | |
| 8,138,195 B2 | 3/2012 | Sadhu et al. | |
| 8,193,182 B2 | 6/2012 | Ren et al. | |
| 8,207,153 B2 | 6/2012 | Fowler et al. | |
| 8,492,389 B2 | 7/2013 | Sadhu et al. | |
| 8,569,323 B2 | 10/2013 | Ren et al. | |
| 8,604,032 B2 | 12/2013 | Ren et al. | |
| 8,623,881 B2 | 1/2014 | Sadhu et al. | |
| 8,637,533 B2 | 1/2014 | Sadhu et al. | |
| 8,653,077 B2 | 2/2014 | Sadhu et al. | |
| 8,703,777 B2 | 4/2014 | Ren et al. | |
| 8,785,433 B2 | 7/2014 | Knight et al. | |
| 8,785,456 B2 | 7/2014 | Ren et al. | |
| 8,785,470 B2 | 7/2014 | Castro et al. | |
| 2010/0256167 A1 | 10/2010 | Fowler et al. | |
| 2011/0021541 A1 | 1/2011 | White et al. | |
| 2012/0015964 A1 | 1/2012 | Fowler et al. | |
| 2013/0029982 A1 | 1/2013 | Castro et al. | |
| 2013/0029984 A1 | 1/2013 | Castro et al. | |
| 2013/0143902 A1 | 6/2013 | Evarts et al. | |
| 2013/0345216 A1 | 12/2013 | Ren et al. | |
| 2014/0088099 A1 | 3/2014 | Ren et al. | |
| 2014/0100214 A1 | 4/2014 | Castro et al. | |
| 2014/0154772 A1 | 6/2014 | Sadhu et al. | |
| 2014/0179673 A1 | 6/2014 | Evarts et al. | |
| 2014/0179718 A1 | 6/2014 | Evarts et al. | |
| 2014/0206684 A1 | 7/2014 | Ren et al. | |
| 2014/0288048 A1 | 9/2014 | Castro et al. | |
| 2014/0296260 A1 | 10/2014 | Askew et al. | |
| 2014/0341894 A1 | 11/2014 | Ren et al. | |

FOREIGN PATENT DOCUMENTS

| | | |
|---|---|---|
| WO | 2010129816 | 11/2010 |
| WO | 2011008302 | 1/2011 |
| WO | 2013116562 | 8/2013 |
| WO | 2014023083 | 2/2014 |
| WO | 2014060432 | 4/2014 |
| WO | 2014106800 | 7/2014 |
| WO | 2014124757 | 8/2014 |
| WO | 2014201409 | 12/2014 |

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802.*
Berndt et al., The p110delta structure uncovers mechanisms for selectivity and potency of novel PI3K inhibitors, Nat. Chem. Biol., 2010, vol. 6, Issue 2, p. 117-124.
ISR of PCT/US2014/055967.
Written Opinion of PCT/US2014/055967.
The extended European search report of EP14845629.6.

* cited by examiner

*Primary Examiner* — Marcos Sznaidman
(74) *Attorney, Agent, or Firm* — Kam W. Law; Squire Patton Boggs (US) LLP

(57) ABSTRACT

The invention relates to the preparation and use of new aminopyrimidine derivatives as drug candidates in free form or in pharmaceutically acceptable salt form and formulations thereof for the modulation of a disorder or disease which is mediated by the activity of the PI3K enzymes. The invention also provides pharmaceutically acceptable compositions comprising such compounds and methods of using the compositions in the treatment of disorders or diseases, such as disorders of immunity and inflammation in which PI3K enzymes play a role in leukocyte function, and hyperproliferative disorders associated with PI3K activity, including but not restricted to leukemias and solid tumors, in mammals, especially humans.

16 Claims, No Drawings

SUBSTITUTED AMINOPYRIMIDINE COMPOUNDS AND METHODS OF USE

CROSS-REFERENCE TO RELATED APPLICATIONS

This application claims the benefits of U.S. Provisional Application No. 61/880,974, filed on Sep. 22, 2013, and U.S. Provisional Application No. 61/983,444, filed on Apr. 23, 2014, all of which are hereby incorporated by reference in their entirety.

FIELD OF THE INVENTION

The present invention is directed to certain novel compounds which are inhibitors of kinase activity, processes for their preparation, pharmaceutical compositions comprising the compounds, and the use of the compounds or the compositions in the treatment of various disorders. More specifically, the compounds of the invention are inhibitors of the activity or function of the phosphatidylinositol 3-kinase kinase family (hereinafter PI3-kinases, PI3Ks), for example PI3Kδ, PI3Kα, PI3Kβ and/or PI3Kγ.

The compounds of the present invention are therefore potentially useful in the treatment of a wide range of disorders, particularly disorders including but not limited to autoimmune disorders, inflammatory diseases, allergic diseases, disease or infection associated immunopathologies, airway diseases, such as asthma and COPD, transplant rejection, cancers such as hematopoietic origin or solid tumors.

The compounds of the present invention are inhibitors of the activity or function of PI3-kinases that may be useful in the treatment of disorders of general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, including but not restricted to autoimmune diseases such as systemic lupus erythematosis (SLE), myestenia gravis, rheumatoid arthritis, acute disseminated encephalomyelitis, idiopathic thrombocytopenic purpura, multiples sclerosis, Sjoegren's syndrome and autoimmune hemolytic anemia, allergic conditions including all forms of hypersensitivity; respiratory diseases such as asthma, chronic obstructive pulmonary disease (COPD) and idiopathic pulmonary fibrosis (IPF); viral infections including viral respiratory tract infections and viral exacerbation of respiratory diseases such as asthma and COPD; non-viral respiratory infections including aspergillosis and leishmaniasis; cardiovascular diseases including thrombosis and atherosclerosis; neurodegenerative diseases; pancreatitis; multiorgan failure; kidney diseases; platelet aggregation; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia and Central pain; hematologic malignancies such as acute myeloid leukaemia (AML), myelo-dysplastic syndrome (MDS), myelo-proliferative diseases (MPD), chronic myeloid leukemia (CML), T-cell acute lymphoblastic leukaemia (T-ALL), B-cell acute lymphoblastic leukaemia (B-ALL), Non Hodgkins Lymphoma (NHL), B-cell lymphoma and solid tumors, such as breast cancer.

BACKGROUND OF THE INVENTION

The phosphoinositide 3-kinases (PI3 kinases or PI3Ks), a family of lipid kinases, have been found to have key regulatory roles in many cellular processes including cell survival, proliferation and differentiation. As major effectors downstream of receptor tyrosine kinases (RTKs) and G protein-coupled receptors (GPCRs), PI3Ks transduce signals from various growth factors and cytokines into intracellular massages by generating phospholipids, which activate the serine-threonine protein kinase AKT (also known as protein kinase B (PKB)) and other downstream effector pathways. The tumor suppressor or PTEN (phosphatase and tensin homologue) is the most important negative regulator of the PI3K signaling pathway ("Small-molecule inhibitors of the PI3K signaling network." *Future Med Chem.*, 2011, 3, 5, 549-565).

To date, eight mammalian PI3Ks have been identified, divided into three main classes (I, II and III) on the basis of their genetic sequence, structure, adapter molecules, expression, mode of activation, and preferred substrate. Among them, Class I PI3Ks are further divided based on signaling pathways and regulatory proteins into class IA and class IB. The class IA PI3Ks comprise three closely related kinases, PI3Kα, PI3Kβ, and PI3Kδ, which exist as heterodimers composed of a catalytic subunit (p110α, p110β, and p110δ respectively) and a p85 regulatory adapter subunits (i.e., p85α, p85β, p55δ, p55α and p50α). The catalytic p110 subunit uses ATP to phosphorylate phosphatidylinositol (PI, PtdIns), PI4P and PI (4,5) P2. These respond to signaling generally through receptor tyrosine kinases (RTKs). The class IB PI3Kγ signals through G-protein-coupled receptors (GPCRs) and is composed of a p110γ catalytic domain that can associate with regulatory subunits distinct from the class IA isoforms.

In relation to function and regulation of effector enzymes in phospholipids signaling pathways, class I PI3-kinases (e.g. PI3Kδ, PI3Kdelta) generate second messengers from the membrane phospholipid pools. Class I PI3Ks convert the membrane phospholipid PI(4,5) P2 into PI(3,4,5)P3, which functions as a second messenger. PI and PI(4)P are also substrates of PI3K and can be phosphorylated and converted into PI3P and PI(3,4)P2, respectively. In addition, these phosphoinositides can be converted into other phosphoinositides by 5'-specific and 3'-specific phosphatases. Thus, PI3K enzymatic activity results either directly or indirectly in the generation of two 3'-phosphoinositide subtypes which function as second messengers in intracellular signal transduction pathways (*Nature Reviews Molecular Cell Biology*, 2010, 11, 329).

Expression of the PI3Kα and PI3Kβ isoforms is ubiquitous, while the expression pattern of PI3Kδ and PI3Kγ seems more restricted, with both isoforms found primarily in leukocytes. The relatively restricted expression pattern of PI3Kδ and PI3Kγ, in addition to data accumulated from studies in mice suggests that these two isoforms play a major role in the adaptive and innate immune systems (*J. Med. Chem.*, 2012, 55, 20, 8559-8581).

In B and T cells, PI3Ks have an important role through activation of the Tec family of protein tyrosine kinases which include Bruton's tyrosine kinase (BTK) in B cells and Interleukin-2-inducible T-cell kinase (ITK) in T cells. Upon PI3K activation, BTK or ITK translocate to the plasma membrane where they are subsequently phosphorylated by Src kinases. One of the major targets of activated ITK is phospholipase C-gamma (PLCγ1), which hydrolyses PI(4,5)P2 into PI(3,4,5)P3 and initiates an intracellular increase in calcium levels and diacylglycerol (DAG) which can activate Protein Kinases C in activated T cells.

The PI3Kδ kinase dead knock-in mice are viable and their phenotype is restricted to defects in immune signaling (Okkenhaug et al., *Science*, 2002, 297, p. 1031-4). These transgenic mice have offered insight into the function of PI3Kδ in B-cell and T-cell signaling. In particular, PI3Kδ is required for PI(3,4,5)P3 formation downstream of CD28 and/or T cell Receptor (TCR) signaling. A key effect of PI3K signaling downstream of TCR is the activation of Akt, which phosphorylates anti-apoptotic factors as well as various transcription factors for cytokine production. As a consequence, T cells with inactive PI3Kδ have defects in proliferation and TM and Th2 cytokine secretion. Activation of T cells through CD28 lowers the threshold for TCR activation by antigen and increases the magnitude and duration of the proliferative response. These effects are mediated by the PI3Kδ-dependent increase in the transcription of a number of genes including IL2, an important T cell growth factor.

Therefore, PI3K inhibitors are anticipated to provide therapeutic benefit via its role in modulating T-cell mediated inflammatory responses associated to respiratory diseases such as asthma, COPD and cystic fibrosis. In addition, there is indication that T-cell directed therapies may provide corticosteroid sparing properties (*Lancet*, 1992, 339, p. 324-8) suggesting that it may provide a useful therapy either as a standalone or in combination with inhaled or oral glucocorticosteroids in respiratory diseases. A PI3K inhibitor might also be used alongside other conventional therapies such as long acting beta-agonists (LABA) in asthma.

In the vasculature, PI3Kδ is expressed by endothelial cells and participates in neutrophil trafficking by modulating the proadhesive state of these cells in response to TNFalpha (*Blood*, 2004, 103, 9, p. 3448). A role for PI3Kδ in TNFalpha-induced signaling of endothelial cells is demonstrated by the pharmacological inhibition of Akt phosphorylation and PDK1 activity. In addition, PI3Kδ is implicated in vascular permeability and airway tissue edema through the VEGF pathway (*Allergy Clin. Immunol.*, 2006, 118, 2, p. 403). These observations suggest additional benefits of PI3Kδ inhibition in asthma by the combined reduction of leukocyte extravasation and vascular permeability associated with asthma. In addition, PI3Kδ activity is required for mast cell function both in vitro and in vivo (*Nature*, 2004, 431, p. 1007; *J. Immunol.*, 2008, 180, 4, p. 2538) further suggesting that PI3K inhibition should be of therapeutic benefit for allergic indications such asthma, allergic rhinitis and atopic dermatitis.

The role of PI3Kδ in B cell proliferation, antibody secretion, B-cell antigen and IL-4 receptor signaling, B-cell antigen presenting function is also well established (*J. Immunol.*, 2007, 178, 4, p. 2328-35; *Blood*, 2006, 107, 2, p. 642-50) and indicates a role in autoimmune diseases such as rheumatoid arthritis or systemic lupus erythematosus. Therefore PI3K inhibitors may also be of benefit for these indications.

Pharmacological inhibition of PI3Kδ inhibits fMLP-dependent neutrophil chemotaxis on an ICAM coated agarose matrix integrin-dependent biased system (*J. Immunol.*, 2003, 170, 5, p. 2647-54) Inhibition of PI3Kδ regulates neutrophil activation, adhesion and migration without affecting neutrophil mediated phagocytosis and bactericidal activity over *Staphylococcus aureus* (*Biochem. Biophys. Res. Commun*, 2003, 308, 4, p. 764-9). Overall, the data suggest that PI3Kδ inhibition should not globally inhibit neutrophil functions required for innate immune defense. PI3Kδ's role in neutrophils offers further scope for treating inflammatory diseases involving tissue remodeling such as COPD or rheumatoid arthritis.

PI3Kγ has been identified as a mediator of G beta-gamma-dependent regulation of JNK activity, and G beta-gamma are subunits of heterotrimeric G proteins (*J. Biol. Chem.*, 1998, 273, 5, p. 2505-8). It has been described that PI3Kγ relays inflammatory signals through various G(i)-coupled receptors and is central to mast cell function, stimuli in the context of leukocytes, and immunology including cytokines, chemokines, adenosines, antibodies, integrins, aggregation factors, growth factors, viruses or hormones for example (*Immunity*, 2002, 16, 3, p. 441-51; *J. Cell Sci.*, 2001, 114 (Pt 16), p. 2903-10 and *Curr. Opinion Cell Biol.*, 2002, 14, 2, p. 203-13).

It is now well understood that deregulation of oncogenes and tumor suppressor genes contributes to the formation of malignant tumors, for example by way of increased cell growth and proliferation or increased cell survival. It is also now known that signaling pathways mediated by the PI3K family have a central role in a number of cell processes including proliferation and survival, and deregulation of these pathways is a causative factor a wide spectrum of human cancers and other diseases (*Annual Rev. Cell Dev. Biol.*, 2001, 17, p. 615-675 and *J. Cell Science*, 2003, 116, 15, p. 3037-3040).

There is good evidence that class I PI3K enzymes contribute to tumorigenesis in a wide variety of human cancers, either directly or indirectly (*Nature Reviews Cancer*, 2002, 2, 7, p. 489-501). For example, inhibition of PI3Kδ may have a therapeutic role for the treatment of malignant haematological disorders such as acute myeloid leukaemia (*Oncogene*, 2006, 25, 50, p. 6648-59). Moreover, activating mutations within p110α (PIK3CA gene) have been associated with various other tumors such as those of the colon and of the breast and lung (*Science*, 2004, 304, 5670, p. 554; *Nature Reviews Cancer*, 2009, 9, 551).

It has also been shown that PI3K is involved in the establishment of central sensitization in painful inflammatory conditions (*J. of Neuroscience*, 2008, 28, 16, p. 4261-4270).

A wide variety of retroviruses and DNA based viruses activate the PI3K pathway as a way of preventing host cell death during viral infection and ultimately exploiting the host cell synthesis machinery for its replication (*Virology*, 2006, 344, 1, p. 131-8 and *Nat. Rev. Microbiol.*, 2008, 6, 4, p. 265-75). Therefore PI3K inhibitors may have anti-viral properties in addition to more established oncolytic and anti-inflammatory indications. These antiviral effects raise interesting prospects in viral induced inflammatory exacerbations. For example, the common cold human rhinovirus (HRV) is responsible for more than 50% of respiratory tract infections but complications of these infections can be significant in certain populations. This is particularly the case in respiratory diseases such as asthma or chronic obstruction pulmonary disease (COPD). Rhinoviral infection of epithelial cells leads to a PI3K dependent cytokine and chemokine secretion (*J. Biol. Chem.*, 2005, 280, 44, p. 36952). This inflammatory response correlates with worsening of respiratory symptoms during infection. Therefore PI3K inhibitors may dampen an exaggerated immune response to an otherwise benign virus. The majority of HRV strains infect bronchial epithelial cells by initially binding to the ICAM-1 receptor. The HRV-ICAM-1 complex is then further internalised by endocytosis and it has been shown that this event requires PI3K activity (*J. Immunol.*, 2008, 180, 2, p. 870-880). Therefore, PI3K inhibitors may also block viral infections by inhibiting viral entry into host cells.

PI3K inhibitors may be useful in reducing other types of respiratory infections including the fungal infection aspergillosis (*Mucosa Immunol.*, 2010, 3, 2, p. 191-205). In addition, PI3Kδ deficient mice are more resistant towards infections by the protozoan parasite *Leishmania major* (*J. Immunol.*, 2009, 183, 3, p. 1921-1933). Taken with effects on viral infections, these reports suggest that PI3K inhibitors may be useful for the treatment of a wide variety of infections.

PI3K inhibition has also been shown to promote regulatory T cell differentiation (*Proc. Natl. Acad. Sci. USA*, 2008, 105, 22, p. 7797-7802) suggesting that PI3K inhibitors may serve therapeutic purposes in auto-immune or allergic indications by inducing immuno-tolerance towards self-antigen or allergen. Recently the PI3Kδ isoform has also been linked to smoke induced glucocorticoid insensitivity (*Am. J. Respir. Crit. Care Med.*, 2009, 179, 7, p. 542-548). This observation suggests that COPD patients, which otherwise respond poorly to corticosteroids, may benefit from the combination of a PI3K inhibitor with a corticosteroid.

PI3K has also been involved in other respiratory conditions such as idiopathic pulmonary fibrosis (IPF). IPF is a fibrotic disease with progressive decline of lung function and increased mortality due to respiratory failure. In IPF, circulating fibrocytes are directed to the lung via the chemokine receptor CXCR4. PI3K is required for both signaling and expression of CXCR4 (*Int. J. Biochem. and Cell Biol.*, 2009, 41, p. 1708-1718). Therefore, by reducing CXCR4 expression and blocking its effector function, a PI3K inhibitor should inhibit the recruitment of fibrocytes to the lung and consequently slow down the fibrotic process underlying IPF, a disease with high unmet need.

PI3Kα and PI3Kβ play an essential role in maintaining homeostasis and pharmacological inhibition of these molecular targets has been associated with cancer therapy (Maira et al., *Expert Opin. Ther. Targets*, 2008, 12, 223).

PI3Kα is involved in insulin signaling and cellular growth pathways (*Nature*, 2006, 441, 366). PI3Kδ isoform-selective inhibition is expected to avoid potential side effects such as hyperglycemia, and metabolic or growth disregulation.

Selective compounds to modulate PI3Kγ are being developed by several groups as immunosuppressive agents for autoimmune disease (*Nature Reviews*, 2006, 5, 903-918). Of note, AS 605240, a selective PI3K gamma inhibitor, has been shown to be efficacious in a mouse model of rheumatoid arthritis (*Nature Medicine*, 2005, 11, 936-943) and to delay onset of disease in a model of systemic lupus erythematosis (*Nature Medicine*, 2005, 11, 933-935).

PI3Kδ-selective inhibitors have also been described recently. The most selective compounds include the quinazolinone purine inhibitors (PIK39 and IC87114). IC87114 inhibits PI3Kδ in the high nanomolar range (triple digit) and has greater than 100-fold selectivity against PI3Kδ, is 52 fold selective against PI3Kβ but lacks selectivity against PI3Kγ (approx. 8-fold). It shows no activity against any protein kinases tested (*Cell*, 2006, 125, 733-747). Using delta-selective compounds or genetically manipulated mice (PI3Kβ$^{D910A}$), it was shown that in addition to playing a key role in B and T cell activation, PI3Kδ is also partially involved in neutrophil migration and primed neutrophil respiratory burst and leads to a partial block of antigen-IgE mediated mast cell degranulation (*Blood*, 2005, 106, 1432-1440; *Nature*, 2002, 431, 1007-1011). Hence PI3Kδ is emerging as an important mediator of many key inflammatory responses that are also known to participate in aberrant inflammatory conditions, including but not limited to auto-immune disease and allergy. To support this notion, there is a growing body of PI3Kδ target validation data derived from studies using both genetic tools and pharmacologic agents.

Thus, using the delta-selective compound 18714 and the PI3Kδ$^{D910A}$ mice, Ali et al. (*Nature*, 2002, 431, 1007-1011) have demonstrated that PI3Kδ plays a critical role in a murine model of allergic disease. In the absence of functional delta, passive cutaneous anaphylaxis (PCA) is significantly reduced and can be attributed to a reduction in allergen-NE induced mast cell activation and degranulation. In addition, inhibition of delta with IC 87114 has been shown to significantly ameliorate inflammation and disease in a murine model of asthma using ovalbumin-induced airway inflammation (*FASEB*, 2006, 20: 455-465). These data utilizing compound were corroborated in PI3Kδ$^{D910A}$ mutant mice using the same model of allergic airway inflammation by a different group (*Eur. J. Immunol.*, 2007, 37, 416-424).

There is a need to provide new PI3K inhibitors that are good drug candidates. In particular, compounds of the invention should bind potently to PI3K whilst showing little affinity for other receptors and show functional activity as inhibitors. They should be well absorbed from the gastro-intestinal tract, be metabolically stable and possess favorable pharmacokinetic properties. When targeted against receptors in the central nervous system they should cross the blood brain barrier freely and when targeted selectively against receptors in the peripheral nervous system they should not cross the blood brain barrier. They should be non-toxic and demonstrate few side-effects. Furthermore, the ideal drug candidate will exist in a physical form that is stable, non-hygroscopic and easily formulated. The compounds of the invention show a certain level of selectivity against the different paralogs PI3K α, β, γ and δ. In particular, show a certain level of selectivity for the isoform PI3Kδ.

The compounds of the present invention are therefore potentially useful in the treatment of a wide range of disorders, particularly disorders including but not limited to autoimmune disorders, inflammatory diseases, allergic diseases, disease or infection associated immunopathologies, airway diseases, transplant rejection, cancers of hematopoietic origin or solid tumors.

The invention also relates to the treatment, either alone or in combination, with one or more other pharmacologically active compounds, includes methods of treating conditions, diseases or disorders in respiratory diseases including asthma, chronic obstructive pulmonary disease (COPD) and idiopathic pulmonary fibrosis (IPF); viral infections including viral respiratory tract infections and viral exacerbation of respiratory diseases such as asthma and COPD; non-viral respiratory infections including aspergillosis and leishmaniasis; allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis (*Future Med. Chem.*, 2013, 5, 4, 479-492; *Biochemical Society Transactions*, 2004, 32, 378); hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia and Central pain;

hematologic malignancies such as Acute Myeloid leukaemia (AML) Myelo-dysplastic syndrome (MDS) myelo-proliferative diseases (MPD) Chronic Myeloid Leukemia (CML) T-cell acute lymphoblastic leukaemia (T-ALL) B-cell Acute Lymphoblastic leukaemia (B-ALL) NonHodgkins Lymphoma (NHL) B-cell lymphoma and solid tumors, such as breast cancer.

SUMMARY OF THE INVENTION

The present inventors have discovered novel compounds which are inhibitors of kinase activity, in particular PI3-kinase activity. Compounds which are PI3-kinase inhibitors may be useful in the treatment of disorders associated with inappropriate kinase activity, in particular inappropriate PI3-kinase activity, for example in the treatment and prevention of disorders mediated by PI3-kinase mechanisms. Such disorders include respiratory diseases including asthma, chronic obstructive pulmonary disease (COPD) and idiopathic pulmonary fibrosis (IPF); viral infections including viral respiratory tract infections and viral exacerbation of respiratory diseases such as asthma and COPD; non-viral respiratory infections including aspergillosis and leishmaniasis; allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia and central pain.

In one embodiment, compounds of the invention may show selectivity for PI3-kinases over other kinases.

In another embodiment, compounds of the invention may be potent inhibitors of PI3Kδ.

In a further embodiment, compounds of the invention may show selectivity for PI3Kδ over other PI3-kinases.

In one aspect, provided herein is a compound having Formula (I):

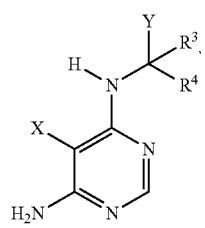

(I)

or a stereoisomer, a geometric isomer, a tautomer, an N-oxide, a solvate, a hydrate, a metabolite, a pharmaceutically acceptable salt or a prodrug thereof, wherein each of X, Y, $R^3$ and $R^4$ is as defined herein.

In certain embodiments, X is $(C_3-C_7)$heterocyclyl, $-(C_1-C_4)$alkylene-$(C_3-C_7)$heterocyclyl, $(C_6-C_{10})$aryl, $-(C_1-C_4)$alkylene-$(C_6-C_{10})$aryl, 5-10 membered heteroaryl, or $-(C_1-C_4)$alkylene-(5-10 membered heteroaryl), wherein X is optionally substituted by 1, 2, 3, 4 or 5 $R^1$ groups;

Y is

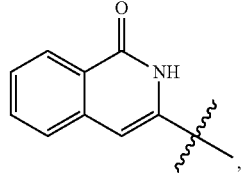

wherein Y is optionally substituted by 1, 2, 3, 4 or 5 $R^2$ groups;

each $R^1$ and $R^2$ is independently H, F, Cl, Br, CN, $NO_2$, oxo (=O), $-C(=O)R^a$, $-C(=O)OR^a$, $-C(=O)NR^aR^b$, $-OC(=O)NR^aR^b$, $-OC(=O)OR^a$, $-N(R^c)C(=O)NR^aR^b$, $-N(R^c)C(=O)OR^a$, $-N(R^c)C(=O)R^a$, $-S(=O)_2NR^aR^b$, $-S(=O)_2R^a$, $-N(R^c)S(=O)_2R^a$, $-N(R^c)-(C_1-C_4)$alkylene-$S(=O)_2R^a$, $-(C_1-C_4)$alkylene-$C(=O)NR^aR^b$, $-(C_1-C_4)$alkylene-$N(R^c)C(=O)NR^aR^b$, $-(C_1-C_4)$alkylene-$N(R^c)C(=O)OR^a$, $-(C_1-C_4)$alkylene-$OC(=O)NR^aR^b$, $-(C_1-C_4)$alkylene-$S(=O)_2NR^aR^b$, $-(C_1-C_4)$alkylene-$N(R^c)S(=O)_2R^a$, $OR^a$, $NR^aR^b$, $-(C_1-C_4)$alkylene-$OR^a$, $-(C_1-C_4)$alkylene-$NR^aR^b$, $(C_1-C_6)$alkyl, $(C_2-C_6)$alkenyl, $(C_2-C_6)$alkynyl, $(C_3-C_8)$cycloalkyl, $-(C_1-C_4)$alkylene-$(C_3-C_8)$cycloalkyl, $(C_3-C_7)$heterocyclyl, $-(C_1-C_4)$alkylene-$(C_3-C_7)$heterocyclyl, $(C_6-C_{10})$aryl, $-(C_1-C_4)$alkylene-$(C_6-C_{10})$aryl, 5-10 membered heteroaryl, or $-(C_1-C_4)$alkylene-(5-10 membered heteroaryl), wherein each of the $(C_1-C_6)$alkyl, $(C_2-C_6)$alkenyl, $(C_2-C_6)$alkynyl, $(C_3-C_8)$cycloalkyl, $-(C_1-C_4)$alkylene-$(C_3-C_8)$cycloalkyl, $(C_3-C_7)$heterocyclyl, $-(C_1-C_4)$alkylene-$(C_3-C_7)$heterocyclyl, $(C_6-C_{10})$aryl, $(C_1-C_4)$alkylene-$(C_6-C_{10})$aryl, 5-10 membered heteroaryl and $-(C_1-C_4)$alkylene-(5-10 membered heteroaryl) is optionally substituted with 1, 2, 3 or 4 substitutents independently selected from F, Cl, Br, CN, $OR^a$, $NR^aR^b$, $(C_1-C_6)$alkyl, $-(C_1-C_4)$alkylene-$OR^a$ and $-(C_1-C_4)$alkylene-$NR^aR^b$;

each of $R^3$ and $R^4$ is independently H, F, CN, $-C(=O)R^a$, $-C(=O)OR^a$, $-C(=O)NR^aR^b$, $-(C_1-C_4)$alkylene-$C(=O)NR^aR^b$, $-(C_1-C_4)$alkylene-$N(R^c)C(=O)NR^aR^b$, $-(C_1-C_4)$alkylene-$N(R^c)C(=O)OR^a$, $-(C_1-C_4)$alkylene-$OC(=O)NR^aR^b$, $-(C_1-C_4)$alkylene-$S(=O)_2NR^aR^b$, $-(C_1-C_4)$alkylene-$N(R^c)S(=O)_2R^b$, $-(C_1-C_4)$alkylene-$OR^a$, $-(C_1-C_4)$alkylene-$NR^aR^b$, $(C_1-C_6)$alkyl, $(C_2-C_6)$alkenyl, $(C_2-C_6)$alkynyl, $(C_3-C_8)$cycloalkyl, $-(C_1-C_4)$alkylene-$(C_3-C_8)$cycloalkyl, $(C_3-C_7)$heterocyclyl, $-(C_1-C_4)$alkylene-$(C_3-C_7)$heterocyclyl, $(C_6-C_{10})$aryl, $-(C_1-C_4)$alkylene-$(C_6-C_{10})$aryl, 5-10 membered heteroaryl, or $-(C_1-C_4)$alkylene-(5-10 membered heteroaryl), wherein each of the $(C_1-C_6)$alkyl, $(C_2-C_6)$alkenyl, $(C_2-C_6)$alkynyl, $(C_3-C_8)$cycloalkyl, $-(C_1-C_4)$alkylene-$(C_3-C_8)$cycloalkyl, $(C_3-C_7)$heterocyclyl, $-(C_1-C_4)$alkylene-$(C_3-C_7)$heterocyclyl, $(C_6-C_{10})$aryl, $-(C_1-C_4)$alkylene-$(C_6-C_{10})$aryl, 5-10 membered heteroaryl and $-(C_1-C_4)$alkylene-(5-10 membered heteroaryl) is optionally substituted with 1, 2, 3 or 4 substitutents independently selected from F, Cl, Br, CN, $OR^a$, $NR^aR^b$, $(C_1-C_6)$alkyl, $-(C_1-C_4)$alkylene-$OR^a$ and $-(C_1-C_4)$alkylene-$NR^aR^b$; or $R^3$ and $R^4$, together with the carbon atom they are attached to, form an optionally substituted 3-8 membered carbocyclic or heterocyclic ring; and each $R^a$, $R^b$ and $R^c$ is independently H, $(C_1-C_6)$alkyl, $(C_2-C_6)$alkenyl, $(C_2-C_6)$alkynyl, $(C_3-C_6)$cycloalkyl, $-(C_1-C_4)$alkylene-$(C_3-C_6)$cycloalkyl, $(C_3-C_6)$heterocyclyl, $-(C_1-C_4)$alkylene-$(C_3-C_6)$heterocyclyl, $(C_6-C_{10})$aryl, $-(C_1-C_4)$alkylene-$(C_6-C_{10})$aryl, 5-10 membered heteroaryl, or —(C$_1$-C$_4$)alkylene-(5-10 membered heteroaryl), wherein each of the (C$_1$-C$_6$)alkyl, (C$_2$-C$_6$)alkenyl, (C$_2$-C$_6$) alkynyl, (C$_3$-C$_6$)cycloalkyl, —(C$_1$-C$_4$)alkylene-(C$_3$-C$_6$)cycloalkyl, (C$_3$-C$_6$)heterocyclyl, —(C$_1$-C$_4$)alkylene-(C$_3$-C$_6$) heterocyclyl, (C$_6$-C$_{10}$)aryl, —(C$_1$-C$_4$)alkylene-(C$_6$-C$_{10}$) aryl, 5-10 membered heteroaryl and —(C$_1$-C$_4$)alkylene-(5-10 membered heteroaryl) is optionally substituted with 1, 2, 3 or 4 substitutents independently selected from F, Cl, CN, N$_3$, OH, NH$_2$, (C$_1$-C$_6$)alkyl, (C$_1$-C$_6$)haloalkyl, (C$_1$-C$_6$) alkoxy and (C$_1$-C$_6$)alkylamino; or R$^a$ and R$^b$, together with the nitrogen atom they are attached to, form an optionally substituted 3-8 membered heterocyclic ring.

In another embodiment, X is (C$_3$-C$_7$)heterocyclyl or 5-10 membered heteroaryl, wherein X is optionally substituted by 1, 2, 3 or 4 R$^1$ groups.

In another embodiment, each R$^1$ and R$^2$ is independently H, F, Cl, CN, oxo (=O), —C(=O)OR$^a$, —C(=O)NR$^a$R$^b$, —N(R$^c$)C(=O)NR$^a$R$^b$, —N(R$^c$)C(=O)OR$^a$, —N(R$^c$)C(=O)R$^a$, —S(=O)$_2$NR$^a$R$^b$, —N(R$^c$)S(=O)$_2$R$^a$, —N(R$^c$)—(C$_1$-C$_4$)alkylene-S(=O)$_2$R$^a$, —(C$_1$-C$_4$)alkylene-C(=O)NR$^a$R$^b$, —(C$_1$-C$_4$)alkylene-N(R$^c$)C(=O)NR$^a$R$^b$, —(C$_1$-C$_4$)alkylene-S(=O)$_2$NR$^a$R$^b$, —(C$_1$-C$_4$)alkylene-N(R$^c$)S(=O)$_2$R$^a$, OR$^a$, NR$^a$R$^b$, —(C$_1$-C$_4$)alkylene-OR$^a$, —(C$_1$-C$_4$)alkylene-NR$^a$R$^b$, (C$_1$-C$_6$)alkyl, (C$_2$-C$_6$)alkenyl, (C$_2$-C$_6$)alkynyl, (C$_3$-C$_8$)cycloalkyl, —(C$_1$-C$_4$)alkylene-(C$_3$-C$_8$)cycloalkyl, (C$_3$-C$_7$)heterocyclyl, —(C$_1$-C$_4$)alkylene-(C$_3$-C$_7$)heterocyclyl, (C$_6$-C$_{10}$)aryl, —(C$_1$-C$_4$)alkylene-(C$_6$-C$_{10}$)aryl, 5-10 membered heteroaryl, or —(C$_1$-C$_4$)alkylene-(5-10 membered heteroaryl), wherein each of the (C$_1$-C$_6$) alkyl, (C$_2$-C$_6$)alkenyl, (C$_2$-C$_6$)alkynyl, (C$_3$-C$_8$)cycloalkyl, —(C$_1$-C$_4$)alkylene-(C$_3$-C$_8$)cycloalkyl, (C$_3$-C$_7$)heterocyclyl, —(C$_1$-C$_4$)alkylene-(C$_3$-C$_7$)heterocyclyl, (C$_6$-C$_{10}$)aryl, —(C$_1$-C$_4$)alkylene-(C$_6$-C$_{10}$)aryl, 5-10 membered heteroaryl, and —(C$_1$-C$_4$)alkylene-(5-10 membered heteroaryl) is optionally substituted with 1, 2, 3 or 4 substitutents independently selected from F, Cl, CN, OR$^a$, NR$^a$R$^b$, (C$_1$-C$_3$)alkyl, —(C$_1$-C$_4$)alkylene-OR$^a$ and —(C$_1$-C$_4$)alkylene-NR$^a$R$^b$.

In another embodiment, each of R$^3$ and R$^4$ is independently H, F, CN, —C(=O)NR$^a$R$^b$, —(C$_1$-C$_2$)alkylene-C(=O)NR$^a$R$^b$, —(C$_1$-C$_2$)alkylene-N(R$^c$)C(=O)NR$^a$R$^b$, —(C$_1$-C$_2$)alkylene-N(R$^c$)C(=O)OR$^a$, —(C$_1$-C$_2$)alkylene-OC(=O)NR$^a$R$^b$, —(C$_1$-C$_2$)alkylene-S(=O)$_2$NR$^a$R$^b$, —(C$_1$-C$_2$)alkylene-N(R$^c$)S(=O)$_2$R$^b$, —(C$_1$-C$_2$)alkylene-OR$^a$, —(C$_1$-C$_2$)alkylene-NR$^a$R$^b$, (C$_1$-C$_4$)alkyl, (C$_2$-C$_4$)alkenyl, (C$_2$-C$_4$)alkynyl, (C$_3$-C$_6$)cycloalkyl, —(C$_1$-C$_2$)alkylene-(C$_3$-C$_6$)cycloalkyl, (C$_3$-C$_5$)heterocyclyl, —(C$_1$-C$_2$) alkylene-(C$_3$-C$_5$)heterocyclyl, phenyl, —(C$_1$-C$_2$)alkylene-phenyl, 5-membered heteroaryl, or —(C$_1$-C$_2$)alkylene-(5-membered heteroaryl), wherein each of the (C$_1$-C$_4$)alkyl, (C$_2$-C$_4$)alkenyl, (C$_2$-C$_4$)alkynyl, (C$_3$-C$_6$)cycloalkyl, —(C$_1$-C$_2$)alkylene-(C$_3$-C$_6$)cycloalkyl, (C$_3$-C$_5$)heterocyclyl, —(C$_1$-C$_2$)alkylene-(C$_3$-C$_5$)heterocyclyl, phenyl, —(C$_1$-C$_2$) alkylene-phenyl, 5-membered heteroaryl and —(C$_1$-C$_2$) alkylene-(5-membered heteroaryl) is optionally substituted with 1, 2, 3 or 4 substitutents independently selected from F, Cl, Br, CN, OR$^a$, NR$^a$R$^b$, (C$_1$-C$_6$)alkyl, —(C$_1$-C$_4$)alkylene-OR$^a$ and —(C$_1$-C$_4$)alkylene-NR$^a$R$^b$; or R$^3$ and R$^4$, together with the carbon atom they are attached to, form an optionally substituted 3-8 membered carbocyclic or heterocyclic ring.

In another embodiment, each R$^a$, R$^b$ and R$^c$ is independently H, (C$_1$-C$_6$)alkyl, (C$_2$-C$_6$)alkenyl, (C$_2$-C$_6$)alkynyl, (C$_3$-C$_6$)cycloalkyl, —(C$_1$-C$_4$)alkylene-(C$_3$-C$_6$)cycloalkyl, (C$_3$-C$_6$)heterocyclyl, —(C$_1$-C$_4$)alkylene-(C$_3$-C$_6$)heterocyclyl, or 5-10 membered heteroaryl, wherein each of the (C$_1$-C$_6$)alkyl, (C$_2$-C$_6$)alkenyl, (C$_2$-C$_6$)alkynyl, (C$_3$-C$_6$)cycloalkyl, —(C$_1$-C$_4$)alkylene-(C$_3$-C$_6$)cycloalkyl, (C$_3$-C$_6$)het-erocyclyl, —(C$_1$-C$_4$)alkylene-(C$_3$-C$_6$)heterocyclyl and 5-10 membered heteroaryl is optionally substituted with 1, 2, 3 or 4 substitutents independently selected from F, CN, N$_3$, OH, NH$_2$, (C$_1$-C$_3$)alkyl, (C$_1$-C$_3$)haloalkyl, (C$_1$-C$_4$)alkoxy and (C$_1$-C$_4$)alkylamino.

In another embodiment, X is a monovalent heterocyclyl or heteroaryl group derived from one of the following structures:

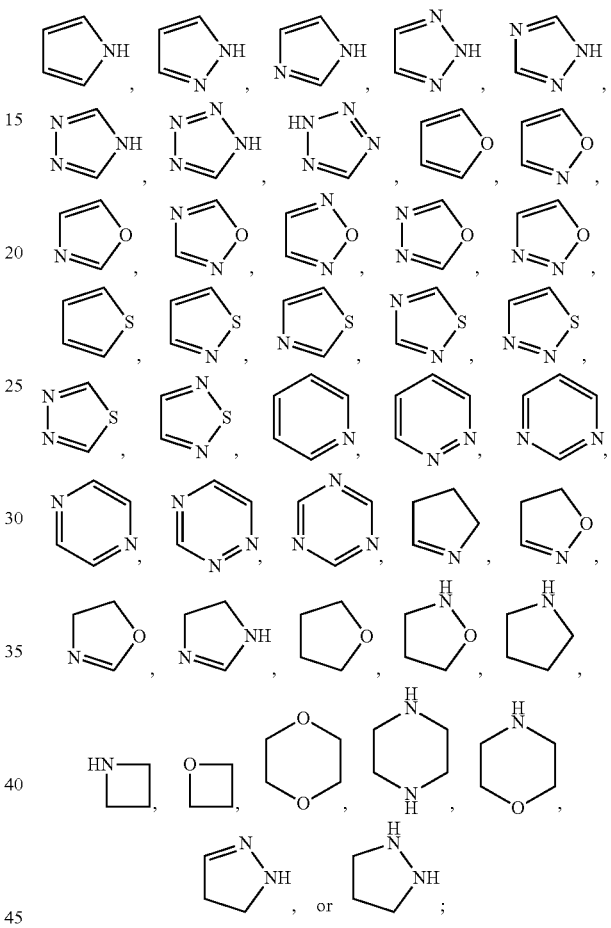

and wherein X is optionally substituted by 1, 2 or 3 R$^1$ groups.

In another embodiment, Y is

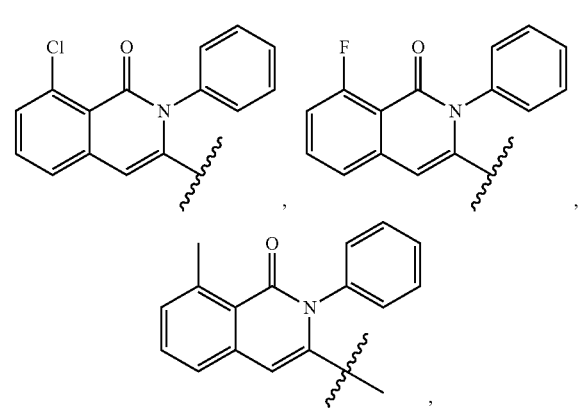

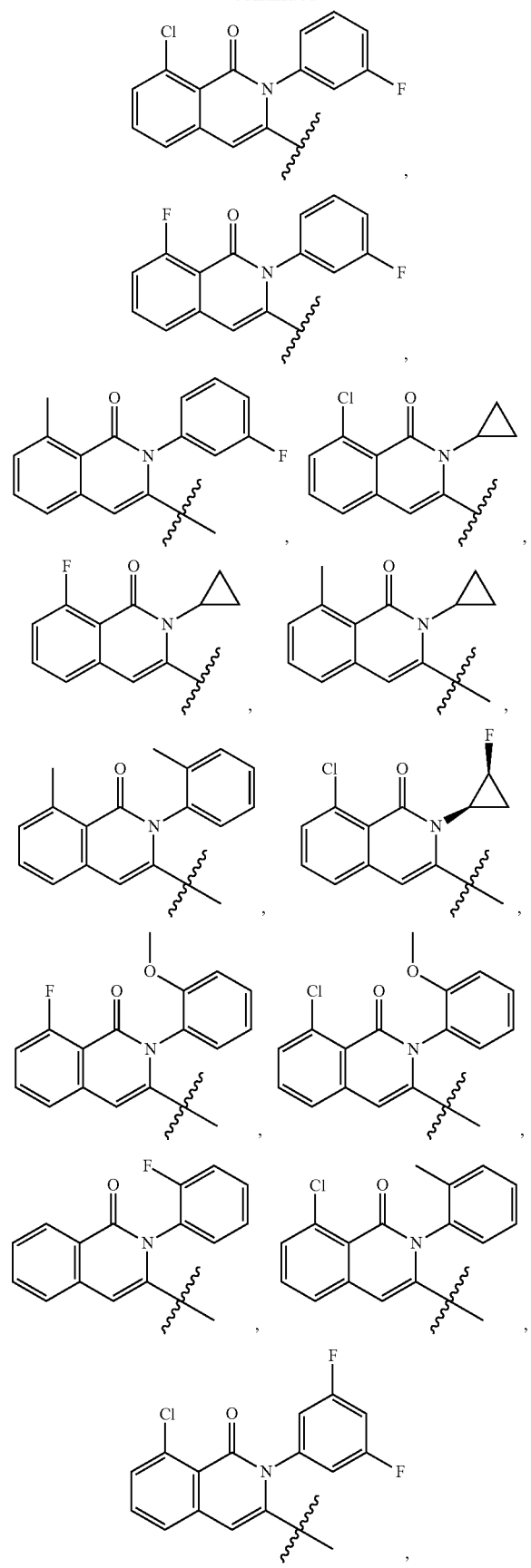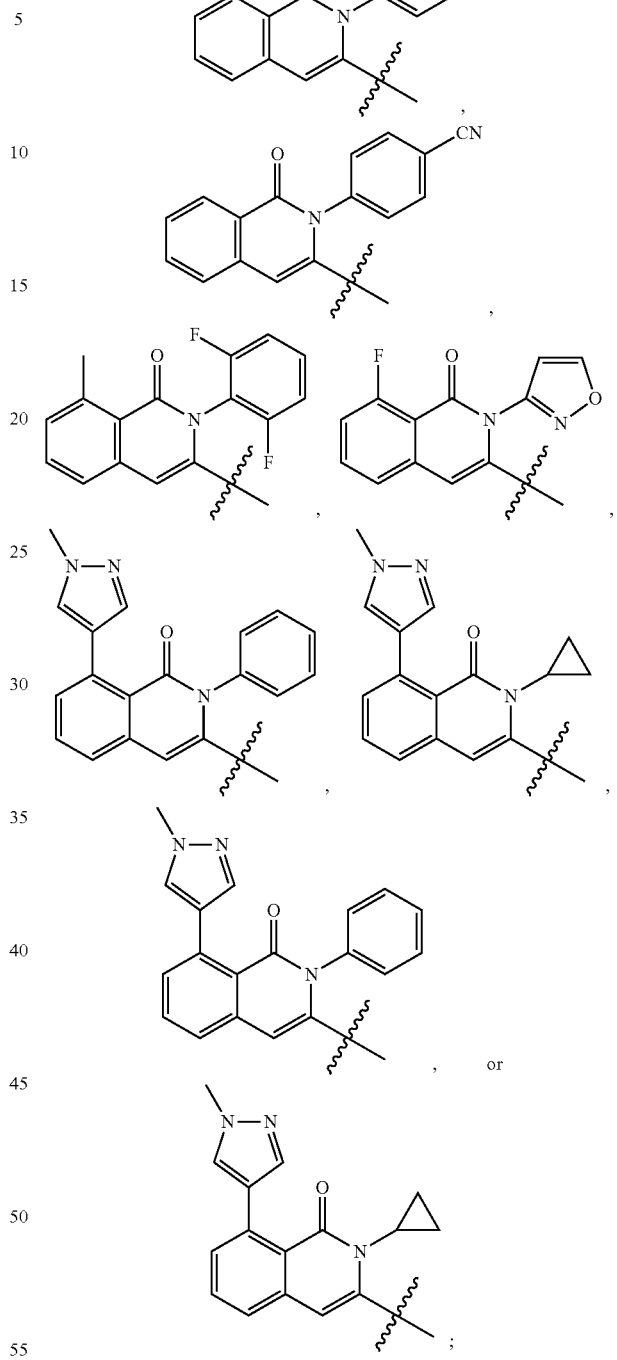

and wherein Y is optionally substituted by 1, 2 or 3 $R^2$ groups.

In another embodiment, each of $R^3$ and $R^4$ is independently H, F, CN, $(C_1-C_3)$alkyl, $(C_3-C_6)$cycloalkyl, $(C_3-C_5)$heterocyclyl, or $-(C_1-C_2)$alkylene-$(C_3-C_5)$heterocyclyl, wherein each of the $(C_1-C_3)$alkyl, $(C_3-C_6)$cycloalkyl, $(C_3-C_5)$heterocyclyl and $-(C_1-C_2)$alkylene-$(C_3-C_5)$heterocyclyl is optionally substituted with 1, 2, 3 or 4 substitutents independently selected from F, Cl, Br, CN, $OR^a$, $NR^aR^b$, $(C_1-C_6)$alkyl, $-(C_1-C_4)$alkylene-$OR^a$ and $-(C_1-C_4)$alkylene-$NR^aR^b$; or $R^3$ and $R^4$, together with the carbon atom they are attached to, form an optionally substituted 3-8 membered carbocyclic or heterocyclic ring.

In another embodiment, each $R^1$ and $R^2$ is independently H, F, Cl, CN, oxo (=O), —C(=O)$OR^a$, —C(=O)$NR^aR^b$, —N($R^c$)C(=O)$NR^aR^b$, —N($R^c$)C(=O)$OR^a$, —N($R^c$)C(=O)$R^a$, —N($R^c$)—($C_1$-$C_2$)alkylene-S(=O)$_2R^a$, —($C_1$-$C_2$)alkylene-C(=O)$NR^aR^b$, —($C_1$-$C_2$)alkylene-N($R^c$)C(=O)$NR^aR^b$, —($C_1$-$C_2$)alkylene-N($R^c$)S(=O)$_2R^a$, $OR^a$, $NR^aR^b$, —($C_1$-$C_2$)alkylene-$OR^a$, —($C_1$-$C_2$)alkylene-$NR^aR^b$, ($C_1$-$C_4$)alkyl, ($C_2$-$C_4$)alkenyl, ($C_2$-$C_4$)alkynyl, ($C_3$-$C_6$)cycloalkyl, —($C_1$-$C_2$)alkylene-($C_3$-$C_6$)cycloalkyl, ($C_3$-$C_5$)heterocyclyl, —($C_1$-$C_2$)alkylene-($C_3$-$C_5$)heterocyclyl, phenyl, —($C_1$-$C_2$)alkylene-phenyl, 5-6 membered heteroaryl, or —($C_1$-$C_2$)alkylene-(5-6 membered heteroaryl), wherein each of the ($C_1$-$C_4$)alkyl, ($C_2$-$C_4$)alkenyl, ($C_2$-$C_4$)alkynyl, ($C_3$-$C_6$)cycloalkyl, —($C_1$-$C_2$)alkylene-($C_3$-$C_6$)cycloalkyl, ($C_3$-$C_5$)heterocyclyl, —($C_1$-$C_2$)alkylene-($C_3$-$C_5$)heterocyclyl, phenyl, —($C_1$-$C_2$)alkylene-phenyl, 5-6 membered heteroaryl and —($C_1$-$C_2$)alkylene-(5-6 membered heteroaryl) is optionally substituted with 1, 2, 3 or 4 substitutents independently selected from F, Cl, CN, $OR^a$, $NR^aR^b$ and ($C_1$-$C_3$)alkyl.

In one aspect of the invention, the compound disclosed herein, or the pharmaceutically acceptable salt disclosed herein is provided for use as a medicament.

In another of the invention, a pharmaceutical composition is provided which comprises a pharmaceutically acceptable carrier, excipient, diluent, adjuvant, vehicle or a combination thereof, and a compound of formula (I) or a pharmaceutically acceptable salt thereof. In some embodiments, the composition comprising one or more therapeutic agents. In another embodiment, the composition is a liquid, solid, semi-solid, gel, or an aerosol form.

Another aspect of the invention provides a method of modulating the activity of the PI3K enzymes, preferably of the PI3Kδ isoform, in a subject, which comprises administering to the subject a therapeutically effective amount of a compound disclosed herein, or a pharmaceutically acceptable salt thereof.

Another aspect of the invention provides a method of treating a disorder mediated by inappropriate PI3-kinase activity comprising administering a safe and effective amount of a compound disclosed herein, or a pharmaceutically acceptable salt thereof, to a patient in need thereof.

Another aspect of the invention provides a method of treating a disorder mediated by inappropriate PI3-kinase activity comprising administering a pharmaceutical disclosed herein, to a patient in need thereof.

In some embodiments, the disorder mediated by inappropriate PI3-kinase activity is a respiratory disease, a viral infection, a non-viral respiratory infection, an allergic disease, an autoimmune disease, an inflammatory disorder, a cardiovascular disease, a hematologic malignancy, a neurodegenerative disease, pancreatitis, multiorgan failure, kidney disease, platelet aggregation, cancer, sperm motility, transplantation rejection, graft rejection, lung injury, or pain.

In another embodiments, the disorder mediated by inappropriate PI3-kinase activity is asthma, chronic obstructive pulmonary disease (COPD), viral respiratory tract infections, viral exacerbation of respiratory diseases, aspergillosis, leishmaniasis, allergic rhinitis, atopic dermatitis, rheumatoid arthritis, multiple sclerosis, inflammatory bowel disease, thrombosis, atherosclerosis, hematologic malignancy, neurodegenerative disease, pancreatitis, multiorgan failure, kidney disease, platelet aggregation, cancer, sperm motility, transplantation rejection, graft rejection, lung injury, pain associated with rheumatoid arthritis or osteoarthritis, back pain, general inflammatory pain, post hepatic neuralgia, diabetic neuropathy, inflammatory neuropathic pain (trauma), trigeminal neuralgia or central pain.

Another aspect of the invention provides use of the compound disclosed herein, or a pharmaceutically acceptable salt thereof, or the pharmaceutical composition disclosed herein in the manufacture of a medicament for the treatment of a disorder or a disease selected from asthma, chronic obstructive pulmonary disease (COPD), viral respiratory tract infections, viral exacerbation of respiratory diseases, aspergillosis, leishmaniasis, allergic rhinitis, atopic dermatitis, rheumatoid arthritis, multiple sclerosis, inflammatory bowel disease, thrombosis, atherosclerosis, hematologic malignancy, neurodegenerative disease, pancreatitis, multiorgan failure, kidney disease, platelet aggregation, cancer, spermmotility, transplantation rejection, graft rejection, lung injury, pain associated with rheumatoid arthritis or osteoarthritis, back pain, general inflammatory pain, post hepatic neuralgia, diabetic neuropathy, inflammatory neuropathic pain (trauma), trigeminal neuralgia or central pain.

In another aspect of the invention, a method of inhibiting a phosphatidyl inositol-3 kinase (PI3 kinase), is provided comprising: contacting the PI3 kinase with an effective amount of a compound disclosed herein. In some embodiments, the step of contacting comprises contacting a cell that contains said PI3 kinase. In some embodiments of the method, the inhibition takes place in a subject suffering from a disorder associated with malfunctioning of one or more types of PI3 kinase. Some exemplary diseases involving malfunctioning of one or more types of PI3 kinases are selected from the group consisting of autoimmune diseases, rheumatoid arthritis, respiratory disease, allergic reactions, and various types of cancers.

In some embodiments, the method comprises administering a second therapeutic agent to the subject.

In certain embodiments, the PI3K-mediated condition or disorder is selected from rheumatoid arthritis, ankylosing spondylitis, osteoarthritis, psoriatic arthritis, psoriasis, inflammatory diseases, and autoimmune diseases. In other embodiments, the PI3K-mediated condition or disorder is selected from cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease. In still other embodiments, the PI3K-mediated condition or disorder is selected from cancer, colon cancer, glioblastoma, endometrial carcinoma, hepatocellular cancer, lung cancer, melanoma, renal cell carcinoma, thyroid carcinoma, cell lymphoma, lymphoproliferative disorders, small cell lung cancer, squamous cell lung carcinoma, glioma, breast cancer, prostate cancer, ovarian cancer, cervical cancer, and leukemia. In yet another embodiment, the PI3K-mediated condition or disorder is selected from type II diabetes. In still other embodiments, the PI3K-mediated condition or disorder is selected from respiratory diseases, bronchitis, asthma, and chronic obstructive pulmonary disease. In certain embodiments, the subject is a human.

Another aspect of the invention relates to the treatment of PI3K-mediated condition or disorder in a patient comprising the step of administering a compound according to any of the above embodiments.

Another aspect of the invention relates to the treatment of rheumatoid arthritis, ankylosing spondylitis, osteoarthritis, psoriatic arthritis, psoriasis, inflammatory diseases or autoimmune diseases in a patient comprising the step of administering a compound according to any of the above embodiments.

Another aspect of the invention relates to the treatment of respiratory diseases including asthma, chronic obstructive pulmonary disease (COPD) and idiopathic pulmonary fibrosis (IPF) in a patient comprising the step of administering a compound according to any of the above embodiments.

Another aspect of the invention relates to the treatment of inflammatory bowel disorders, inflammatory eye disorders, inflammatory or unstable bladder disorders, skin complaints with inflammatory components, chronic inflammatory conditions, systemic lupus erythematosis (SLE), myestenia gravis, acute disseminated encephalomyelitis, idiopathic thrombocytopenic purpura, multiples sclerosis, Sjoegren's syndrome and autoimmune hemolytic anemia, allergic conditions and hypersensitivity in a patient, comprising the step of administering a compound according to any of the above or below embodiments.

Another aspect of the invention relates to the treatment of cancers in a patient that are mediated, dependent on or associated with PI3K activity, particularly PI3Kdelta activity, comprising the step of administering a compound according to any of the above or below embodiments.

Another aspect of the invention relates to the treatment of cancers are selected from acute myeloid leukaemia, myelodysplastic syndrome, myeloproliferative diseases, chronic myeloid leukaemia, T-cell acute lymphoblastic leukaemia, B-cell acute lymphoblastic leukaemia, non-hodgkins lymphoma, B-cell lymphoma, solid tumors and breast cancer, comprising the step of administering a compound according to any of the above or below embodiments.

Another aspect of the invention relates to the use of a compound according to any of the above embodiments as a medicament.

Another aspect of the invention relates to the use of a compound according to any of the above embodiments in the manufacture of a medicament for the treatment of PI3K-mediated condition or disorder in a patient.

Another aspect of the invention relates to the use of a compound according to any of the above embodiments in the manufacture of a medicament for the treatment of rheumatoid arthritis, ankylosing spondylitis, osteoarthritis, psoriatic arthritis, psoriasis, inflammatory diseases, respiratory diseases including asthma, chronic obstructive pulmonary disease (COPD) and idiopathic pulmonary fibrosis (IPF), autoimmune diseases, and cancers.

Unless otherwise stated, all stereoisomers, geometric isomers, tautomers, solvates, hydrates, metabolites, salts, and pharmaceutically acceptable prodrugs of the compounds disclosed herein are within the scope of the invention.

In certain embodiments, the salt is a pharmaceutically acceptable salt. The phrase "pharmaceutically acceptable" indicates that the substance or composition must be compatible chemically and/or toxicologically, with the other ingredients comprising a formulation, and/or the mammal being treated therewith.

The compounds of the invention also include salts of such compounds which are not necessarily pharmaceutically acceptable salts, and which may be useful as intermediates for preparing and/or purifying compounds of Formula (I) and/or for separating enantiomers of compounds of Formula (I).

The compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms.

In another aspect, provided herein are methods of preparing, methods of separating, and methods of purifying compounds of Formula (I). The compounds of the present invention may have in general several asymmetric centers and are typically depicted in the form of racemic mixtures. This invention is intended to encompass racemic mixtures, partially racemic mixtures and separate enantiomers and diasteromers.

Compounds of the present invention can be in the form of one of the possible isomers, rotamers, atropisomers, tautomers or mixtures thereof. This invention is intended to encompass mixtures of isomers, rotamers, atropisomers, tautomers, partially mixed isomers, rotamers, atropisomers, or tautomers, and separated isomers, rotamers, atropisomers, tautomers.

In another aspect, the compounds of the invention include isotopically labeled compounds as defined herein, for example those into which radioactive isotopes, such as $^3$H, $^{14}$C and $^{18}$F or those into which non-radioactive isotopes, such as $^2$H and $^{13}$C are present.

In another aspect, provided herein are methods of preparing, methods of separating, and methods of purifying compounds of Formula (I).

The foregoing merely summarizes certain aspects of the invention and is not intended to be limiting in nature. These aspects and other aspects and embodiments are described more fully below.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

Unless defined otherwise, all technical and scientific terms used herein have the same meaning as is commonly understood by one of skill in the art to which this invention belongs. AU patents and publications referred to herein are incorporated by reference.

As used herein, the following definitions shall apply unless otherwise indicated. For purposes of this invention, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry", Thomas Sorrell, University Science Books, Sausalito: 1999, and "March's Advanced Organic Chemistry," by Michael B. Smith and Jerry March, John Wiley & Sons, New York: 2007, the entire contents of which are hereby incorporated by reference.

The term "a," "an," "the" and similar terms used in the context of the present invention are to be construed to cover both the singular and plural unless otherwise indicated herein or clearly contradicted by the context.

The term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, "patient" refers to a human (including adults and children or other animal. In one embodiment, "patient" refers to a human.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{16}O$, $^{17}O$, $^{18}O$, $^{31}P$, $^{32}P$, $^{36}S$, $^{18}F$, and $^{37}Cl$.

Compounds disclosed herein that contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detection. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994.

Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

The compounds disclosed herein may contain asymmetric or chiral centers, and therefore exist in different stereoisomeric forms. It is intended that all stereoisomeric forms of the compounds disclosed herein, including but not limited to, diastereomers, enantiomers, atropisomers, and geometric (or conformational) isomers as well as mixtures thereof such as racemic mixtures, form part of the present invention.

Unless otherwise stated, structures depicted herein are also meant to include all isomeric (e.g., enantiomeric, diastereomeric, atropisomeric and geometric (or conformational)) forms of the structure; for example, the R and S configurations for each asymmetric center, (Z) and (E) double bond isomers, and (Z) and (E) conformational isomers.

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. Unless otherwise stated, all tautomeric forms of the compounds disclosed herein are within the scope of the invention.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., "Enantiomers, Racemates and Resolutions," Wiley Interscience, New York, 1981; Gawley et al., *Principles of Asymmetric Synthesis,*

2nd Ed. Elsevier, Oxford, UK, 2012; Eliel et al., Stereochemistry of Carbon Compounds, McGraw-Hill, NY, 1962; Wilen et al., "Tables of Resolving Agents and Optical Resolutions," p. 268 (E. L. Eliel, Ed., Univ. of Notre Dame Press, Notre Dame, Ind., 1972) and Subramanian et al., "Chiral Separation Techniques: A Practical Approach," Ed., Wiley-VCH Verlag GmbH & Co. KGaA, Weinheim, Germany, 2007.

As described herein, compounds disclosed herein may optionally be substituted with one or more substituents, such as are illustrated generally below, or as exemplified by particular classes, subclasses, and species of the invention. It will be appreciated that the phrase "optionally substituted" is used interchangeably with the phrase "substituted or unsubstituted". In general, the term "substituted" refers to the replacement of one or more hydrogen radicals in a given structure with the radical of a specified substituent. The term "optional" or "optionally" means that the subsequently described event or circumstance may but need not occur, and that the description includes instances where the event or circumstance occurs and instances in which it does not. Unless otherwise indicated, an optionally substituted group may have a substituent at each substitutable position of the group. When more than one position in a given structure can be substituted with more than one substituent selected from a specified group, the substituent may be either the same or different at each position.

The term "alkyl" or "alkyl group" refers to a saturated linear or branched-chain monovalent hydrocarbon radical of 1 to 20 carbon atoms, wherein the alkyl radical may be optionally substituted independently with one or more substituents described below. Unless otherwise specified, the alkyl group contains 1-20 carbon atoms. In some embodiments, the alkyl group contains 1-12 carbon atoms. In other embodiments, the alkyl group contains 1-10 carbon atoms. In other embodiments, the alkyl group contains 1-8 carbon atoms. In other embodiments, the alkyl group contains 1-6 carbon atoms. In still other embodiments, the alkyl group contains 1-4 carbon atoms, and in yet other embodiments, the alkyl group contains 1-3 carbon atoms.

Some non-limiting examples of the alkyl group include methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, 1-heptyl, 1-octyl, and the like.

The prefix "alk-" is inclusive of both straight chain and branched saturated carbon chain.

The term "alkylene" refers to a saturated divalent hydrocarbon group derived from a straight or branched chain saturated hydrocarbon by the removal of two hydrogen atoms. Unless otherwise specified, the alkylene group contains 1-6 carbon atoms. In some embodiments, the alkylene group contains 1-4 carbon atoms. In other embodiments, the alkylene group contains 1-2 carbon atoms. Examples of the alkylene group include, but are not limited to, methylene (—CH$_2$—), ethylidene (—CH$_2$CH$_2$—), isopropylidene (—CH(CH$_3$)CH$_2$—), and the like.

The term "alkenyl" refers to linear or branched-chain monovalent hydrocarbon radical of 2 to 12 carbon atoms with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. Preferably the alkenyl group contains 2 to 8 carbon atoms, more preferably 2 to 6 carbon atoms, and most preferably 2 to 4 carbon atoms. Some non-limiting examples of the alkenyl group include ethylenyl or vinyl (—CH═CH$_2$), allyl (—CH$_2$CH═CH$_2$), and the like.

The term "alkynyl" refers to a linear or branched monovalent hydrocarbon radical of 2 to 12 carbon atoms with at least one site of unsaturation, i.e., a carbon-carbon, sp triple bond, wherein the alkynyl radical may be optionally substituted independently with one or more substituents described herein. Preferably the alkynyl group contains 2 to 8 carbon atoms, more preferably 2 to 6 carbon atoms, and most preferably 2 to 4 carbon atoms. Some non-limiting examples of the alkynyl group include ethynyl (—C≡CH), propynyl (propargyl, —CH$_2$CδCH), —C≡C—CH$_3$, and the like.

The term "alkoxy" refers to an alkyl group, as previously defined, attached to the principal carbon atom through an oxygen atom. Unless otherwise specified, the alkoxy group contains 1-20 carbon atoms. In some embodiments, the alkoxy group contains 1-10 carbon atoms. In other embodiments, the alkoxy group contains 1-8 carbon atoms. In still other embodiments, the alkoxy group contains 1-6 carbon atoms, and in yet other embodiments, the alkoxy group contains 1-4 carbon atoms. In further embodiments, the alkoxy group contains 1-3 carbon atoms.

Some non-limiting examples of the alkoxy group include methoxy (MeO, —OCH$_3$), ethoxy (EtO, —OCH$_2$CH$_3$), 1-propoxy (n-PrO, n-propoxy, —OCH$_2$CH$_2$CH$_3$), 2-propoxy (i-PrO, i-propoxy, —OCH(CH$_3$)$_2$), 1-butoxy (n-BuO, n-butoxy, —OCH$_2$CH$_2$CH$_2$CH$_3$), 2-methyl-1-propoxy (i-BuO, i-butoxy, —OCH$_2$CH(CH$_3$)$_2$), 2-butoxy (s-BuO, s-butoxy, —OCH(CH$_3$)CH$_2$CH$_3$), 2-methyl-2-propoxy (t-BuO, t-butoxy, —OC(CH$_3$)$_3$), 1-pentoxy (n-pentoxy, —OCH$_2$CH$_2$CH$_2$CH$_2$CH$_3$), 2-pentoxy (—OCH(CH$_3$)CH$_2$CH$_2$CH$_3$), 3-pentoxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH(CH$_3$)CH$_2$CH$_3$), and the like.

The term "haloalkyl", "haloalkenyl" or "haloalkoxy" refers to alkyl, alkenyl, or alkoxy, as the case may be, substituted with one or more halogen atoms.

The term "carbocycle", "carbocyclyl", or "carbocyclic ring" refers to a monovalent or multivalent non-aromatic, saturated or partially unsaturated ring having 3 to 12 carbon atoms as a monocyclic, bicyclic, or tricyclic ring system. The carbobicyclyl system includes a spiro carbobicyclyl or a fused carbobicyclyl. In some embodiments, the carbocyclic ring group contains 3 to 8 carbon atoms. Some non-limiting examples of the carbocyclyl group include cycloalkyl, cycloalkenyl, and cycloalkynyl. Further non-limiting examples of the carbocyclyl group include cyclopropyl, cyclobutyl, cyclopentyl, 1-cyclopent-1-enyl, 1-cyclopent-2-enyl, 1-cyclopent-3-enyl, cyclohexyl, 1-cyclohex- 1-enyl, 1-cyclohex-2-enyl, 1-cyclohex-3-enyl, cyclohexadienyl, and the like.

The term "cycloalkyl" refers to a monovalent or multivalent saturated ring having 3 to 12 carbon atoms as a monocyclic, bicyclic, or tricyclic ring system. A bicyclic ring system includes a spiro bicyclyl or a fused bicyclyl. In some embodiments, the cycloalkyl group contains 3 to 10 carbon atoms. In other embodiments, the cycloalkyl group contains 3 to 8 carbon atoms. In still other embodiments, the cycloalkyl group contains 3 to 6 carbon atoms, and in yet other embodiments, the cycloalkyl group contains 5 to 6 carbon atoms. The cycloalkyl group is optionally substituted independently with one or more substituents described herein.

The terms "fused bicyclic", "fused cyclic", "fused bicyclyl" and "fused cyclyl" are used interchangeably refer to saturated bridged ring system, which refers to a bicyclic ring system that is not aromatic. Such a system may contain isolated or conjugated unsaturation, but not aromatic or heteroaromatic rings in its core structure (but may have aromatic substitution thereon). The terms "spirocyclyl", "spirocyclic", "spiro bicyclyl" or "spiro bicyclic" are used interchangeably and refer to a ring originating from a particular annular carbon of another ring. For example, as depicted below in Structure a, a saturated bridged ring system (ring B and B') is termed as "fused bicyclic", whereas ring A and ring B share an atom between the two saturated ring system, which terms as a "spirocyclyl" or "spiro bicyclyl". Each cyclic ring in a fused bicyclyl or a spiro bicyclyl can be either a carbocyclyl or a heterocyclyl.

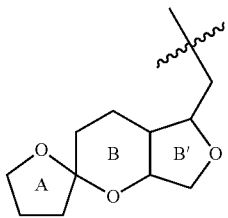

Structure a

The term "heterocycle", "heterocyclyl" or "heterocyclic ring" as used interchangeably herein refers to a monocyclic, bicyclic, or tricyclic ring system in which one or more ring members are independently selected from heteroatoms and that is completely saturated or that contains one or more units of unsaturation, but which is not aromatic, that has one or more points of attachment to the rest of the molecule. A bicyclic ring system includes a spiro bicyclyl or a fused bicyclyl, and one of the rings can be either a monocarbocycle or a monohetercycle. One or more ring atoms are optionally substituted independently with one or more substituents described herein. In some embodiments, the "heterocycle", "heterocyclyl", or "heterocyclic" group is a monocycle having 4 to 8 ring members (3 to 7 carbon atoms and 1 to 3 heteroatoms selected from N, O, P, and S, wherein the S or P is optionally substituted with one or more oxo to provide the group S=O or SO$_2$, PO or PO$_2$). In other embodiments, the "heterocycle", "heterocyclyl", or "heterocyclic" group is a monocycle having 4 to 7 ring members (3 to 6 carbon atoms and 1 to 3 heteroatoms selected from N, O, P, and S, wherein the S or P is optionally substituted with one or more oxo to provide the group S=O or SO$_2$, PO or PO$_2$). In other embodiments, the "heterocycle", "heterocyclyl", or "heterocyclic" group is a monocycle having 3 to 7 ring members (2 to 6 carbon atoms and 1 to 3 heteroatoms selected from N, O, P, and S, wherein the S or P is optionally substituted with one or more oxo to provide the group S=O or SO$_2$, PO or PO$_2$). In still other embodiments, the "heterocycle", "heterocyclyl", or "heterocyclic" group is a monocycle having 4 to 6 ring members (3 to 5 carbon atoms and 1 to 3 heteroatoms selected from N, O, P, and S, wherein the S or P is optionally substituted with one or more oxo to provide the group S=O or SO$_2$, PO or PO$_2$). In yet other embodiments, the "heterocycle", "heterocyclyl", or "heterocyclic" group is a monocycle having 3 to 6 ring members (2 to 5 carbon atoms and 1 to 3 heteroatoms selected from N, O, P, and S, wherein the S or P is optionally substituted with one or more oxo to provide the group S=O or SO$_2$, PO or PO$_2$), or a bicycle having 7 to 10 ring members (4 to 9 carbon atoms and 1 to 3 heteroatoms selected from N, O, P, and S, wherein the S or P is optionally substituted with one or more oxo to provide the group S=O or SO$_2$, PO or PO$_2$).

The heterocyclyl may be a carbon radical or heteroatom radical. Some non-limiting examples of the heterocyclyl group include pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homo-piperazinyl, azetidinyl, oxetanyl, thietanyl, homopiperidinyl, oxepanyl, thiepanyl, oxazepinyl, diazepinyl, thiazepinyl, 4,5-dihydrooxazoly, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 1,2,3,4-tetrahydroisoquinolinyl. Examples of a heterocyclic group wherein 2 ring carbon atoms are substituted with oxo (=O) moieties are pyrimidindionyl and 1,1-dioxo-thiomorpholinyl.

The term "heteroatom" refers to one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or NR (as in N-substituted pyrrolidinyl).

The term "halogen" refers to Fluoro (F), Chloro (Cl), Bromo (Br), or Iodo (I).

The term "azido" or "N$_3$" refers to an azide moiety. This radical may be attached, for example, to a methyl group to form azidomethane (methyl azide, MeN$_3$); or attached to a phenyl group to form phenyl azide (PhN$_3$).

The term "aryl" used alone or as part of a larger moiety as in "aralkyl", "aralkoxy" or "aryloxyalkyl" refers to monocyclic, bicyclic, and tricyclic carbocyclic ring systems having a total of 6 to 14 ring members, preferably, 6 to 12 ring members, and more preferably 6 to 10 ring members, wherein at least one ring in the system is aromatic, wherein each ring in the system contains 3 to 7 ring members and that has one or more points of attachment to the rest of the molecule. The term "aryl" may be used interchangeably with the term "aryl ring" or "aromatic." Some non-limiting examples of the aryl ring would include phenyl, naphthyl, and anthracenyl. The aryl radical is optionally substituted independently with one or more substituents described herein.

The term "heteroaryl" used alone or as part of a larger moiety as in "heteroaralkyl" or "heteroarylalkoxy" refers to monocyclic, bicyclic, and tricyclic ring systems having a total of 5 to 14 ring members, preferably, 5 to 12 ring members, and more preferably 5 to 10 ring members, wherein at least one ring in the system is aromatic, at least one ring in the system contains one or more heteroatoms, wherein each ring in the system contains 5 to 7 ring members and that has one or more points of attachment to the rest of the molecule. In some embodiments, heteroaryl may be a 5-10 membered heteroaryl comprises 1, 2, 3 or 4 heteroatoms independently selected from O, S and N. In another embodiments, heteroaryl may be a 5-6 membered heteroaryl comprises 1, 2, 3 or 4 heteroatoms independently selected from O, S and N. In still another embodiments, heteroaryl may be a 5-membered heteroaryl comprises 1, 2, 3 or 4 heteroatoms independently selected from O, S and N. The term "heteroaryl" may be used interchangeably with the term "heteroaryl ring" or the term "heteroaromatic". The heteroaryl radicals are optionally substituted independently with one or more substituents described herein.

Some non-limiting examples of the heteroaryl ring include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5H-tetrazolyl and 2H-tetrazolyl), triazolyl (e.g., 2-triazolyl, 5-triazolyl, 4H-1,2,4-triazolyl, 1H-1,2,4-triazolyl, and 1,2,3-triazolyl), 2-thienyl, 3-thienyl, pyrazolyl (e.g., 2-pyrazolyl and 3-pyrazolyl), isothiazolyl, 1,2,3-oxadiazolyl, 1,2,5-oxadiazolyl, 1,2,4-oxadiazolyl, 1,3,4-oxadiazolyl, 1,2,3-triazolyl, 1,2,4-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The terms "carboxy" or "carboxyl", whether used alone or with other terms, such as "carboxyalkyl", refers to —CO$_2$H. The term "carbonyl", whether used alone or with other terms, such as "aminocarbonyl", denotes —(C=O)—.

The term "alkylamino" embraces "N-alkylamino" and "N,N-dialkylamino" where amino groups are independently substituted with one alkyl radical or with two alkyl radicals, respectively. Some non-limiting examples of alkylamino radicals are "lower alkylamino" radicals having one or two alkyl radicals of one to six carbon atoms, attached to a nitrogen atom. Suitable alkylamino radicals may be mono or dialkylamino such as N-methylamino, N-ethylamino, N, N-dimethylamino, N, N-diethylamino and the like.

The term "arylamino" refers to amino groups, which have been substituted with one or two aryl radicals, such as N-phenylamino. The arylamino radicals may be further substituted on the aryl ring portion of the radical.

The term "aminoalkyl" refers to linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl.

The term "n membered" where n is an integer typically describes the number of ring-forming atoms in a moiety where the number of ring-forming atoms is n. For example, piperidinyl is an example of a 6 membered heterocycloalkyl and 1,2,3,4-tetrahydro-naphthalenyl is an example of a 10 membered carbocyclyl group.

As described herein, a bond drawn from a substituent to the center of one ring within a ring system (as shown below) represents substitution of the substituent at any substitutable position on the ring to which it is attached. For example, Structure b represents possible substitution in any of the positions on the B ring shown in Structure c-1, c-2 and c-3.

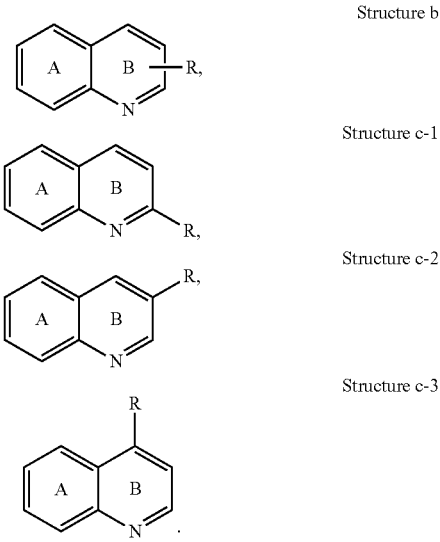

The term "unsaturated" refers to a moiety having one or more units of unsaturation.

The term "comprising" is meant to be open ended, including the indicated component but not excluding other elements.

The term "prodrug" as used herein, represents a compound that is transformed in vivo into a compound of formula (I). Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound disclosed herein that contains an OH group may be acylated at this position in its prodrug form. Other prodrug forms include phosphates, such as, for example those phosphates resulting from the phosphonation of an OH group on the parent compound. A thorough discussion of prodrugs is provided in Higuchi et al., Pro-drugs as Novel Delivery Systems, Vol. 14, A.C.S. Symposium Series; Roche et al., Bioreversible Carriers in Drug Design, American Pharmaceutical Association and Pergamon Press, 1987; Rautio et al., Prodrugs: Design and Clinical Applications, *Nat. Rev. Drug Discovery*, 2008, 7, 255-270, and Hecker et al., Prodrugs of Phosphates and Phosphonates, *J. Med. Chem.*, 2008, 51, 2328-2345, all of which are incorporated herein by reference.

A "metabolite" is a product produced through metabolism in the body of a specified compound or salt thereof. The metabolite of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds disclosed herein, including compounds produced by a process comprising contacting a compound of this invention with a mammal for a period of time sufficient to yield a metabolic product thereof.

A "pharmaceutically acceptable salt" refers to organic or inorganic salts of a compound disclosed herein. The pharmaceutically acceptable salts are well known in the art. For example, Berge et al., describe pharmaceutically acceptable salts in detail in *J. Pharm. Sci.*, 1977, 66, 1-19, which is incorporated herein by reference. Some non-limiting examples of the pharmaceutically acceptable salt include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange.

Other examples of the pharmaceutically acceptable salt include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further examples of the pharmaceutically acceptable salt include, when appropriate, nontoxic ammonium, quaternary ammonium, and amine cations formed using counterions such as halide, hydroxide, carboxylate, sulfate, phosphate, nitrate, $C_{1-8}$ sulfonate and aryl sulfonate.

A "solvate" refers to an association or complex of one or more solvent molecules and a compound disclosed herein. Some non-limiting examples of solvents that form solvates include water, isopropanol, ethanol, methanol, DMSO, ethyl acetate, acetic acid, and ethanolamine. The term "hydrate" refers to the complex where the solvent molecule is water.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, p. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by PI3K or (ii) associated with PI3K activity, or (iii) characterized by activity (normal or abnormal) of PI3K or (2) reduce or inhibit the activity of PI3K or (3) reduce or inhibit the expression of PI3K. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of PI3K; or at least partially reducing or inhibiting the expression of PI3K. The meaning of the term "a therapeutically effective amount" as illustrated in the above embodiment for PI3K also applies by the same means to any other relevant proteins/peptides/enzymes.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment, the term "treat", "treating" or "treatment" refers to alleviating or ameliorating at least one physical parameter including those which may not be discernible by the patient. In yet another embodiment, the term "treat", "treating" or "treatment" refers to modulating the disease or disorder, either physically, (e.g., stabilization of a discernible symptom), physiologically, stabilization of a physical parameter), or both, in yet another embodiment, the term "treat", "treating" or "treatment" refers to preventing or delaying the onset or development or progression of the disease or disorder.

The term "protecting group" or "PG" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxy-methy-1,2-(p-toluenesulfonyl) ethyl, 2-(p-nitrophenylsulfenyl)-ethyl, 2-(diphenylphosphino)-ethyl, nitroethyl and the like. For a general description of protecting groups and their use, see Greene et al., *Protective Groups in Organic Synthesis*, John Wiley & Sons, New York, 1991 and Kocienski et al., *Protecting Groups*, Thieme, Stuttgart, 2005.

Description of the Compounds Disclosed Herein

The present inventors have discovered novel compounds which are inhibitors of kinase activity, in particular PI3-kinase activity. Compounds which are PI3-kinase inhibitors may be useful in the treatment of disorders associated with inappropriate kinase activity, in particular inappropriate PI3-kinase activity, for example in the treatment and prevention of disorders mediated by PI3-kinase mechanisms.

Such disorders include respiratory diseases including asthma, chronic obstructive pulmonary disease (COPD) and idiopathic pulmonary fibrosis (IPF); viral infections including viral respiratory tract infections and viral exacerbation of respiratory diseases such as asthma and COPD; non-viral respiratory infections including aspergillosis and leishmaniasis; allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia and central pain.

In one embodiment, compounds of the invention may show selectivity for PI3-kinases over other kinases.

In another embodiment, compounds of the invention may be potent inhibitors of PI3Kδ.

In a further embodiment, compounds of the invention may show selectivity for PI3Kδ over other PI3-kinases.

In one aspect, provided herein is a compound having Formula (I):

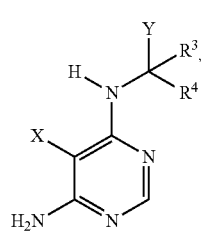

(I)

or a stereoisomer, a geometric isomer, a tautomer, an N-oxide, a solvate, a hydrate, a metabolite, a pharmaceutically acceptable salt or a prodrug thereof, wherein each of X, Y, $R^3$ and $R^4$ is as defined herein.

In certain embodiments, X is ($C_3$-$C_7$)heterocyclyl, —($C_1$-$C_4$)alkylene-($C_3$-$C_7$)heterocyclyl, ($C_6$-$C_{10}$)aryl, —($C_1$-$C_4$)alkylene-($C_6$-$C_{10}$)aryl, 5-10 membered heteroaryl, or —($C_1$-$C_4$)alkylene-(5-10 membered heteroaryl), wherein X is optionally substituted by 1, 2, 3, 4 or 5 $R^1$ groups;

Y is

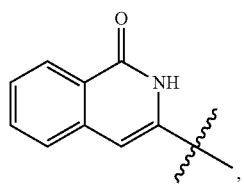

wherein Y is optionally substituted by 1, 2, 3, 4 or 5 $R^2$ groups;

each $R^1$ and $R^2$ is independently H, F, Cl, Br, CN, $NO_2$, oxo (=O), —C(=O)$R^a$, —C(=O)$OR^a$, —C(=O)$NR^aR^b$, —OC(=O)$NR^aR^b$, —OC(=O)$OR^a$, —N($R^c$)C(=O)$NR^aR^b$, —N($R^c$)C(=O)$OR^a$, —N($R^c$)C(=O)$R^a$, —S(=O)$_2NR^aR^b$, —S(=O)$_2R^a$, —N($R^c$)S(=O)$_2R^a$, —N($R^c$)—($C_1$-$C_4$)alkylene-S(=O)$_2R^a$, —($C_1$-$C_4$)alkylene-C(=O)$NR^aR^b$, —($C_1$-$C_4$)alkylene-N($R^c$)C(=O)$NR^aR^b$, —($C_1$-$C_4$)alkylene-N($R^c$)C(=O)$OR^a$, —($C_1$-$C_4$)alkylene-OC(=O)$NR^aR^b$, —($C_1$-$C_4$)alkylene-S(=O)$_2NR^aR^b$, —($C_1$-$C_4$)alkylene-N($R^c$)S(=O)$_2R^a$, $OR^a$, $NR^aR^b$, —($C_1$-$C_4$)alkylene-$OR^a$, —($C_1$-$C_4$)alkylene-$NR^aR^b$, ($C_1$-$C_6$)alkyl, ($C_2$-$C_6$)alkenyl, ($C_2$-$C_6$)alkynyl, ($C_3$-$C_8$)cycloalkyl, —($C_1$-$C_4$)alkylene-($C_3$-$C_8$)cycloalkyl, ($C_3$-$C_7$)heterocyclyl, —($C_1$-$C_4$)alkylene-($C_3$-$C_7$)heterocyclyl, ($C_6$-$C_{10}$)aryl, —($C_1$-$C_4$)alkylene-($C_6$-$C_{10}$)aryl, 5-10 membered heteroaryl, or —($C_1$-$C_4$)alkylene-(5-10 membered heteroaryl), wherein each of the ($C_1$-$C_6$)alkyl, ($C_2$-$C_6$)alkenyl, ($C_2$-$C_6$)alkynyl, ($C_3$-$C_8$)cycloalkyl, —($C_1$-$C_4$)alkylene-($C_3$-$C_8$)cycloalkyl, ($C_3$-$C_7$)heterocyclyl, —($C_1$-$C_4$)alkylene-($C_3$-$C_7$)heterocyclyl, ($C_6$-$C_{10}$)aryl, —($C_1$-$C_4$)alkylene-($C_6$-$C_{10}$)aryl, 5-10 membered heteroaryl and —($C_1$-$C_4$)alkylene-(5-10 membered heteroaryl) is optionally substituted with 1, 2, 3 or 4 substitutents independently selected from F, Cl, Br, CN, $OR^a$, $NR^aR^b$, ($C_1$-$C_6$)alkyl, —($C_1$-$C_4$)alkylene-$OR^a$ and —($C_1$-$C_4$)alkylene-$NR^aR^b$;

each of $R^3$ and $R^4$ is independently H, F, CN, —C(=O)$R^a$, —C(=O)$OR^a$, —C(=O)$NR^aR^b$, —($C_1$-$C_4$)alkylene-C(=O)$NR^aR^b$, —($C_1$-$C_4$)alkylene-N($R^c$)C(=O)$NR^aR^b$, —($C_1$-$C_4$)alkylene-N($R^c$)C(=O)$OR^a$, —($C_1$-$C_4$)alkylene-OC(=O)$NR^aR^b$, —($C_1$-$C_4$)alkylene-S(=O)$_2NR^aR^b$, —($C_1$-$C_4$)alkylene-N($R^c$)S(=O)$_2R^b$, —($C_1$-$C_4$)alkylene-$OR^a$, —($C_1$-$C_4$)alkylene-$NR^aR^b$, ($C_1$-$C_6$)alkyl, ($C_2$-$C_6$)alkenyl, ($C_2$-$C_6$)alkynyl, ($C_3$-$C_8$)cycloalkyl, —($C_1$-$C_4$)alkylene-($C_3$-$C_8$)cycloalkyl, ($C_3$-$C_7$)heterocyclyl, —($C_1$-$C_4$)alkylene-($C_3$-$C_7$)heterocyclyl, ($C_6$-$C_{10}$)aryl, —($C_1$-$C_4$)alkylene-($C_6$-$C_{10}$)aryl, 5-10 membered heteroaryl, or —($C_1$-$C_4$)alkylene-(5-10 membered heteroaryl), wherein each of the ($C_1$-$C_6$)alkyl, ($C_2$-$C_6$)alkenyl, ($C_2$-$C_6$)alkynyl, ($C_3$-$C_8$)cycloalkyl, —($C_1$-$C_4$)alkylene-($C_3$-$C_8$)cycloalkyl, ($C_3$-$C_7$)heterocyclyl, —($C_1$-$C_4$)alkylene-($C_3$-$C_7$)heterocyclyl, ($C_6$-$C_{10}$)aryl, —($C_1$-$C_4$)alkylene-($C_6$-$C_{10}$)aryl, 5-10 membered heteroaryl and —($C_1$-$C_4$)alkylene-(5-10 membered heteroaryl) is optionally substituted with 1, 2, 3 or 4 substitutents independently selected from F, Cl, Br, CN, $OR^a$, $NR^aR^b$, ($C_1$-$C_6$)alkyl, —($C_1$-$C_4$)alkylene-$OR^a$ and —($C_1$-$C_4$)alkylene-$NR^aR^b$; or $R^3$ and $R^4$, together with the carbon atom they are attached to, form an optionally substituted 3-8 membered carbocyclic or heterocyclic ring; and each $R^a$, $R^b$ and $R^c$ is independently H, ($C_1$-$C_6$)alkyl, ($C_2$-$C_6$)alkenyl, ($C_2$-$C_6$)alkynyl, ($C_3$-$C_6$)cycloalkyl, —($C_1$-$C_4$)alkylene-($C_3$-$C_6$)cycloalkyl, ($C_3$-$C_6$)heterocyclyl, —($C_1$-$C_4$)alkylene-($C_3$-$C_6$)heterocyclyl, ($C_6$-$C_{10}$)aryl, —($C_1$-$C_4$)alkylene-($C_6$-$C_{10}$)aryl, 5-10 membered heteroaryl, or —($C_1$-$C_4$)alkylene-(5-10 membered heteroaryl), wherein each of the ($C_1$-$C_6$)alkyl, ($C_2$-$C_6$)alkenyl, ($C_2$-$C_6$)alkynyl, ($C_3$-$C_6$)cycloalkyl, —($C_1$-$C_4$)alkylene-($C_3$-$C_6$)cycloalkyl, ($C_3$-$C_6$)heterocyclyl, —($C_1$-$C_4$)alkylene-($C_3$-$C_6$)heterocyclyl, ($C_6$-$C_{10}$)aryl, —($C_1$-$C_4$)alkylene-($C_6$-$C_{10}$)aryl, 5-10 membered heteroaryl and —($C_1$-$C_4$)alkylene-(5-10 membered heteroaryl) is optionally substituted with 1, 2, 3 or 4 substitutents independently selected from F, Cl, CN, $N_3$, OH, $NH_2$, ($C_1$-$C_6$)alkyl, ($C_1$-$C_6$)haloalkyl, ($C_1$-$C_6$)alkoxy and ($C_1$-$C_6$)alkylamino; or $R^a$ and $R^b$, together with the nitrogen atom they are attached to, form an optionally substituted 3-8 membered heterocyclic ring.

In another embodiment, X is ($C_3$-$C_7$)heterocyclyl or 5-10 membered heteroaryl, wherein X is optionally substituted by 1, 2, 3 or 4 $R^1$ groups.

In another embodiment, each $R^1$ and $R^2$ is independently H, F, Cl, CN, oxo (=O), —C(=O)$OR^a$, —C(=O)$NR^aR^b$, —N($R^c$)C(=O)$NR^aR^b$, —N($R^c$)C(=O)$OR^a$, —N($R^c$)C(=O)$R^a$, —S(=O)$_2NR^aR^b$, —N($R^c$)S(=O)$_2R^a$, —N(R$^c$)—(C$_1$-C$_4$)alkylene-S(=O)$_2$R$^a$, —(C$_1$-C$_4$)alkylene-C(=O)NR$^a$R$^b$, —(C$_1$-C$_4$)alkylene-N(R$^c$)C(=O)NR$^a$R$^b$, —(C$_1$-C$_4$)alkylene-S(=O)$_2$NR$^a$R$^b$, —(C$_1$-C$_4$)alkylene-N(R$^c$)S(=O)$_2$R$^a$, OR$^a$, NR$^a$R$^b$, —(C$_1$-C$_4$)alkylene-OR$^a$, —(C$_1$-C$_4$)alkylene-NR$^a$R$^b$, (C$_1$-C$_6$)alkyl, (C$_2$-C$_6$)alkenyl, (C$_2$-C$_6$)alkynyl, (C$_3$-C$_8$)cycloalkyl, —(C$_1$-C$_4$)alkylene-(C$_3$-C$_8$)cycloalkyl, (C$_3$-C$_7$)heterocyclyl, —(C$_1$-C$_4$)alkylene-(C$_3$-C$_7$)heterocyclyl, (C$_6$-C$_{10}$)aryl, —(C$_1$-C$_4$)alkylene-(C$_6$-C$_{10}$)aryl, 5-10 membered heteroaryl, or —(C$_1$-C$_4$)alkylene-(5-10 membered heteroaryl), wherein each of the (C$_1$-C$_6$)alkyl, (C$_2$-C$_6$)alkenyl, (C$_2$-C$_6$)alkynyl, (C$_3$-C$_8$)cycloalkyl, —(C$_1$-C$_4$)alkylene-(C$_3$-C$_8$)cycloalkyl, (C$_3$-C$_7$)heterocyclyl, —(C$_1$-C$_4$)alkylene-(C$_3$-C$_7$)heterocyclyl, (C$_6$-C$_{10}$)aryl, —(C$_1$-C$_4$)alkylene-(C$_6$-C$_{10}$)aryl, 5-10 membered heteroaryl, and —(C$_1$-C$_4$)alkylene-(5-10 membered heteroaryl) is optionally substituted with 1, 2, 3 or 4 substitutents independently selected from F, Cl, CN, OR$^a$, NR$^a$R$^b$, (C$_1$-C$_3$)alkyl, —(C$_1$-C$_4$)alkylene-OR$^a$ and —(C$_1$-C$_4$)alkylene-NR$^a$R$^b$.

In another embodiment, each of R$^3$ and R$^4$ is independently H, F, CN, —C(=O)NR$^a$R$^b$, —(C$_1$-C$_2$)alkylene-C(=O)NR$^a$R$^b$, —(C$_1$-C$_2$)alkylene-N(R$^c$)C(=O)NR$^a$R$^b$, —(C$_1$-C$_2$)alkylene-N(R$^c$)C(=O)OR$^a$, —(C$_1$-C$_2$)alkylene-OC(=O)NR$^a$R$^b$, —(C$_1$-C$_2$)alkylene-S(=O)$_2$NR$^a$R$^b$, —(C$_1$-C$_2$)alkylene-N(R$^c$)S(=O)$_2$R$^a$, —(C$_1$-C$_2$)alkylene-OR$^a$, —(C$_1$-C$_2$)alkylene-NR$^a$R$^b$, (C$_1$-C$_4$)alkyl, (C$_2$-C$_4$)alkenyl, (C$_2$-C$_4$)alkynyl, (C$_3$-C$_6$)cycloalkyl, —(C$_1$-C$_2$)alkylene-(C$_3$-C$_6$)cycloalkyl, (C$_3$-C$_5$)heterocyclyl, —(C$_1$-C$_2$)alkylene-(C$_3$-C$_5$)heterocyclyl, phenyl, —(C$_1$-C$_2$)alkylene-phenyl, 5-membered heteroaryl, or —(C$_1$-C$_2$)alkylene-(5-membered heteroaryl), wherein each of the (C$_1$-C$_4$)alkyl, (C$_2$-C$_4$)alkenyl, (C$_2$-C$_4$)alkynyl, (C$_3$-C$_6$)cycloalkyl, —(C$_1$-C$_2$)alkylene-(C$_3$-C$_6$)cycloalkyl, (C$_3$-C$_5$)heterocyclyl, —(C$_1$-C$_2$)alkylene-(C$_3$-C$_5$)heterocyclyl, phenyl, —(C$_1$-C$_2$)alkylene-phenyl, 5-membered heteroaryl and —(C$_1$-C$_2$)alkylene-(5-membered heteroaryl) is optionally substituted with 1, 2, 3 or 4 substitutents independently selected from F, Cl, Br, CN, OR$^a$, NR$^a$R$^b$, (C$_1$-C$_6$)alkyl, —(C$_1$-C$_4$)alkylene-OR$^a$ and —(C$_1$-C$_4$)alkylene-NR$^a$R$^b$; or R$^3$ and R$^4$, together with the carbon atom they are attached to, form an optionally substituted 3-8 membered carbocyclic or heterocyclic ring.

In another embodiment, each R$^a$, R$^b$ and R$^c$ is independently H, (C$_1$-C$_6$)alkyl, (C$_2$-C$_6$)alkenyl, (C$_2$-C$_6$)alkynyl, (C$_3$-C$_6$)cycloalkyl, —(C$_1$-C$_4$)alkylene-(C$_3$-C$_6$)cycloalkyl, (C$_3$-C$_6$)heterocyclyl, —(C$_1$-C$_4$)alkylene-(C$_3$-C$_6$)heterocyclyl, or 5-10 membered heteroaryl, wherein each of the (C$_1$-C$_6$)alkyl, (C$_2$-C$_6$)alkenyl, (C$_2$-C$_6$)alkynyl, (C$_3$-C$_6$)cycloalkyl, —(C$_1$-C$_4$)alkylene-(C$_3$-C$_6$)cycloalkyl, (C$_3$-C$_6$)heterocyclyl, —(C$_1$-C$_4$)alkylene-(C$_3$-C$_6$)heterocyclyl and 5-10 membered heteroaryl is optionally substituted with 1, 2, 3 or 4 substitutents independently selected from F, CN, N$_3$, OH, NH$_2$, (C$_1$-C$_3$)alkyl, (C$_1$-C$_3$)haloalkyl, (C$_1$-C$_4$)alkoxy and (C$_1$-C$_4$)alkylamino.

In another embodiment, X is a monovalent heterocyclyl or heteroaryl group derived from one of the following structures:

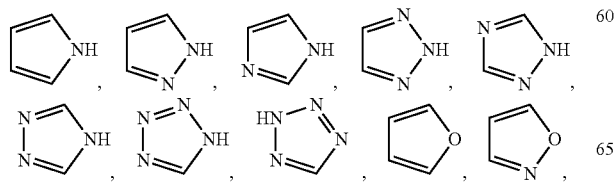

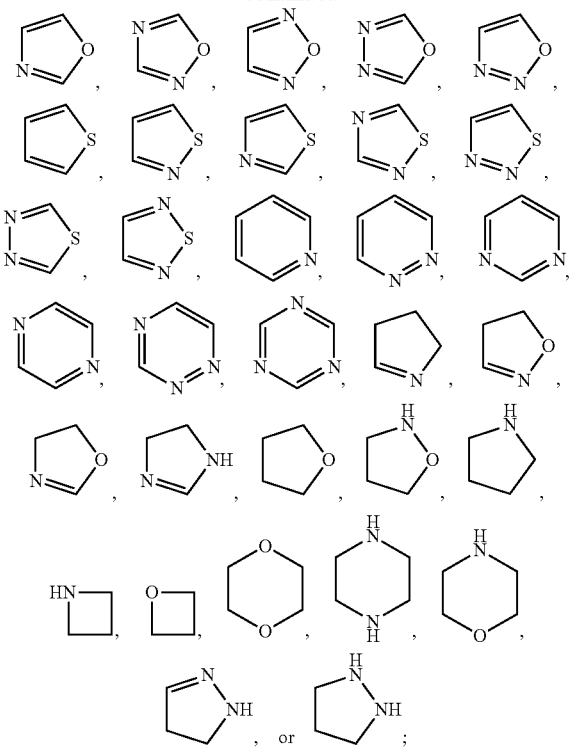

and wherein X is optionally substituted by 1, 2 or 3 R$^1$ groups.

In another embodiment, Y is

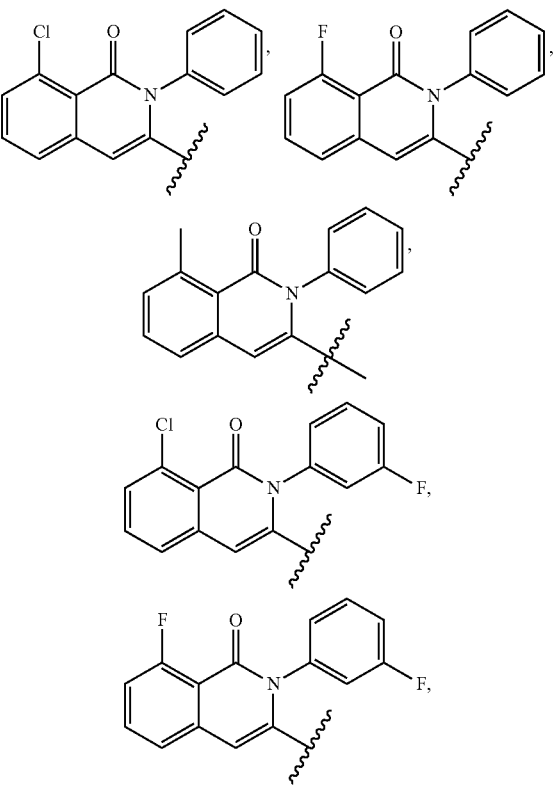

-continued

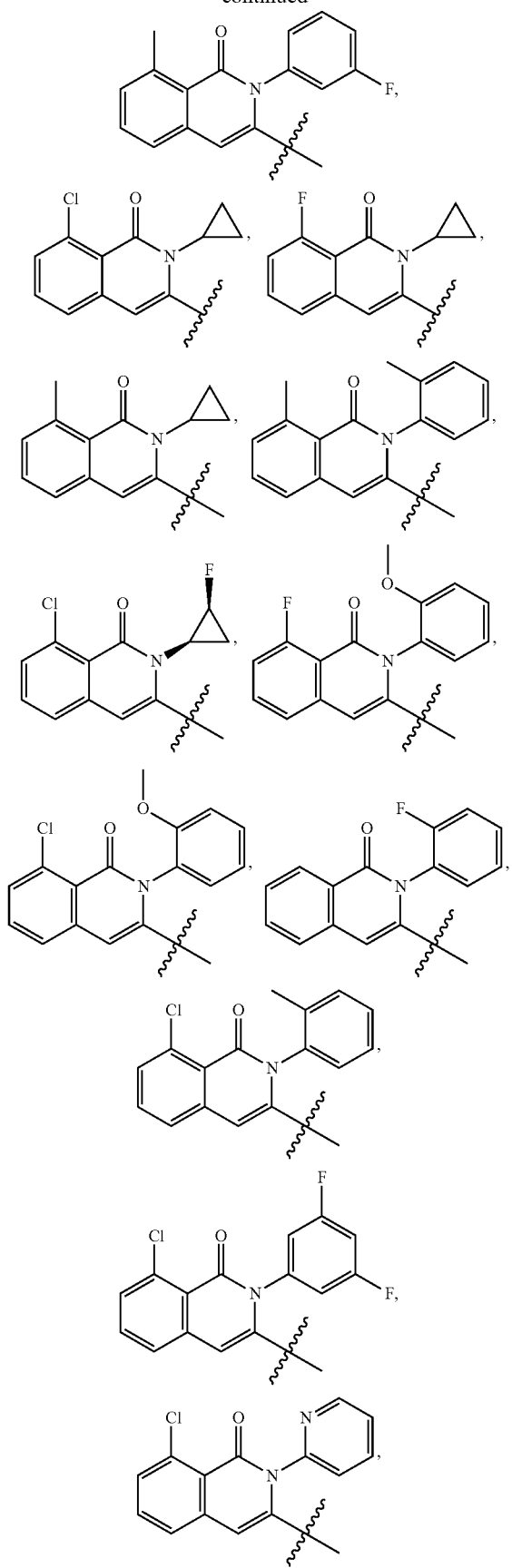

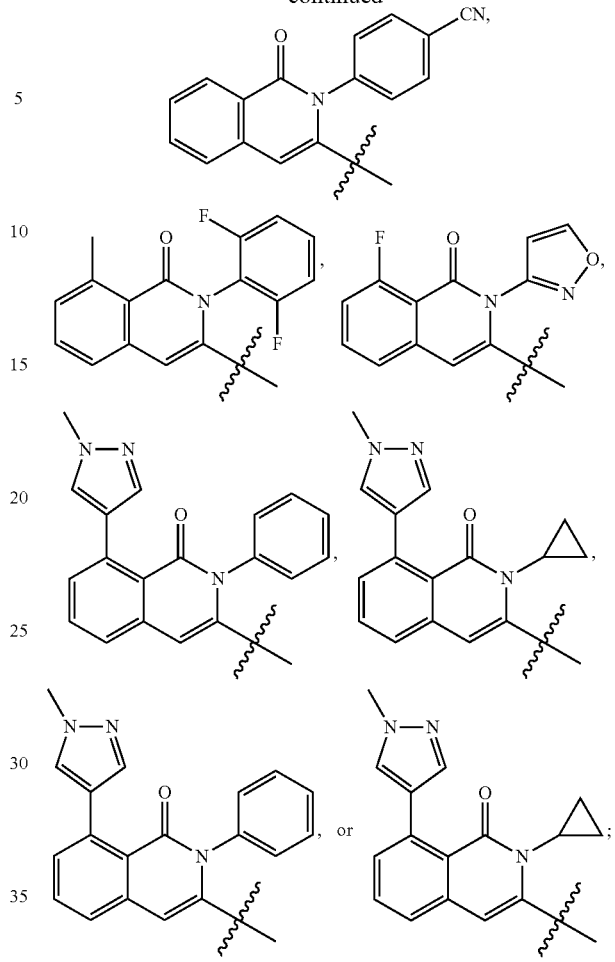

and wherein Y is optionally substituted by 1, 2 or 3 $R^2$ groups.

In another embodiment, each of $R^3$ and $R^4$ is independently H, F, CN, $(C_1-C_3)$alkyl, $(C_3-C_6)$cycloalkyl, $(C_3-C_5)$heterocyclyl, or —$(C_1-C_2)$alkylene-$(C_3-C_5)$heterocyclyl, wherein each of the $(C_1-C_3)$alkyl, $(C_3-C_6)$cycloalkyl, $(C_3-C_5)$heterocyclyl and —$(C_1-C_2)$alkylene-$(C_3-C_5)$heterocyclyl is optionally substituted with 1, 2, 3 or 4 substitutents independently selected from F, Cl, Br, CN, $OR^a$, $NR^aR^b$, $(C_1-C_6)$alkyl, —$(C_1-C_4)$alkylene-$OR^a$ and —$(C_1-C_4)$alkylene-$NR^aR^b$; or $R^3$ and $R^4$, together with the carbon atom they are attached to, form an optionally substituted 3-8 membered carbocyclic or heterocyclic ring.

In another embodiment, each $R^1$ and $R^2$ is independently H, F, Cl, CN, oxo (=O), —C(=O)$OR^a$, —C(=O)$NR^aR^b$, —N($R^c$)C(=O)$NR^aR^b$, —N($R^c$)C(=O)$OR^a$, —N($R^c$)C(=O)$R^a$, —N($R^c$)—$(C_1-C_2)$alkylene-S(=O)$_2R^a$, —$(C_1-C_2)$alkylene-C(=O)$NR^aR^b$, —$(C_1-C_2)$alkylene-N($R^c$)C(=O)$NR^aR^b$, —$(C_1-C_2)$alkylene-N($R^c$)S(=O)$_2R^a$, $OR^a$, $NR^aR^b$, —$(C_1-C_2)$alkylene-$OR^a$, —$(C_1-C_2)$alkylene-$NR^aR^b$, $(C_1-C_4)$alkyl, $(C_2-C_4)$alkenyl, $(C_2-C_4)$alkynyl, $(C_3-C_6)$cycloalkyl, —$(C_1-C_2)$alkylene-$(C_3-C_6)$cycloalkyl, $(C_3-C_5)$heterocyclyl, —$(C_1-C_2)$alkylene-$(C_3-C_5)$heterocyclyl, phenyl, —$(C_1-C_2)$alkylene-phenyl, 5-6 membered heteroaryl, or —$(C_1-C_2)$alkylene-(5-6 membered heteroaryl), wherein each of the $(C_1-C_4)$alkyl, $(C_2-C_4)$alkenyl, $(C_2-C_4)$alkynyl, $(C_3-C_6)$cycloalkyl, —$(C_1-C_2)$alkylene-$(C_3-C_6)$cycloalkyl, $(C_3-C_5)$heterocyclyl, —$(C_1-C_2)$alkylene-$(C_3-C_5)$ heterocyclyl, phenyl, —(C$_1$-C$_2$)alkylene-phenyl, 5-6 membered heteroaryl and —(C$_1$-C$_2$)alkylene-(5-6 membered heteroaryl) is optionally substituted with 1, 2, 3 or 4 substitutents independently selected from F, Cl, CN, OR$^a$, NR$^a$R$^b$ and (C$_1$-C$_3$)alkyl.
Some non-limiting examples of the compound disclosed herein are shown in the following:
TABLE 1
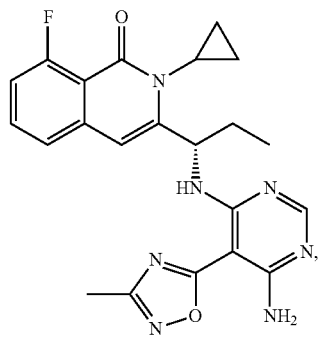 [SMILES: CC[C@H](Nc1ncnc(N)c1-c1nc(C)no1)c1cc2cccc(F)c2c(=O)n1C1CC1]
(1)
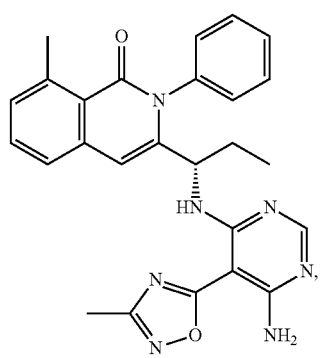 [SMILES: CC[C@H](Nc1ncnc(N)c1-c1nc(C)no1)c1cc2cccc(C)c2c(=O)n1-c1ccccc1]
(2)
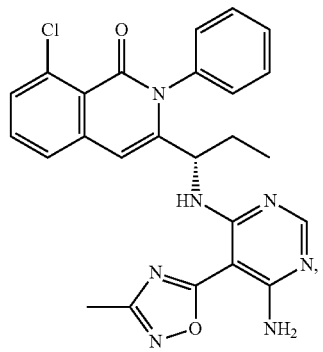 [SMILES: CC[C@H](Nc1ncnc(N)c1-c1nc(C)no1)c1cc2cccc(Cl)c2c(=O)n1-c1ccccc1]
(3)
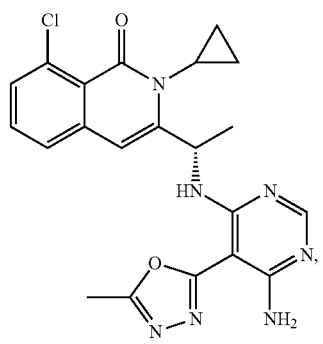 [SMILES: Cc1nnc(-c2c(N)ncnc2N[C@@H](C)c2cc3cccc(Cl)c3c(=O)n2C2CC2)o1]
(4)
TABLE 1-continued
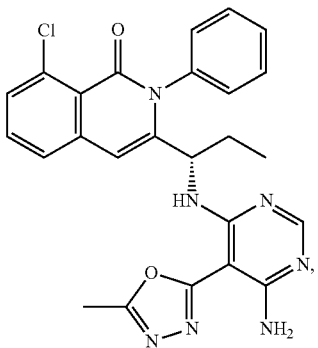 [SMILES: CC[C@H](Nc1ncnc(N)c1-c1nnc(C)o1)c1cc2cccc(Cl)c2c(=O)n1-c1ccccc1]
(5)
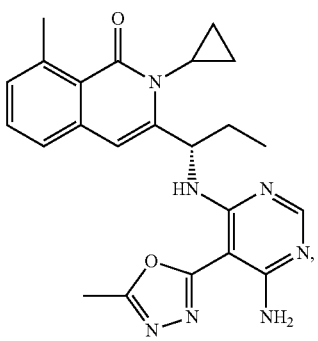 [SMILES: CC[C@H](Nc1ncnc(N)c1-c1nnc(C)o1)c1cc2cccc(C)c2c(=O)n1C1CC1]
(6)
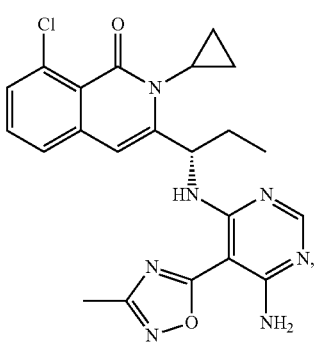
(7)
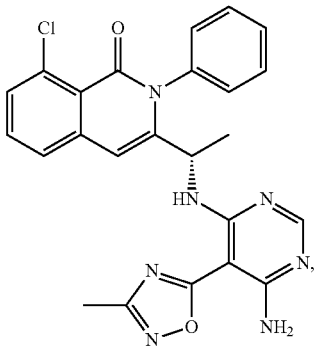 [SMILES: Cc1noc(-c2c(N)ncnc2N[C@@H](C)c2cc3cccc(Cl)c3c(=O)n2-c2ccccc2)n1]
(8)

TABLE 1-continued
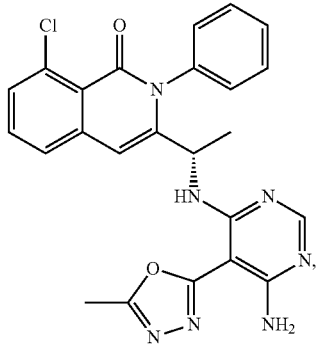 [SMILES: Cc1nnc(-c2c(N)ncnc2N[C@@H](C)c2cc3cccc(Cl)c3c(=O)n2-c2ccccc2)o1] (9)
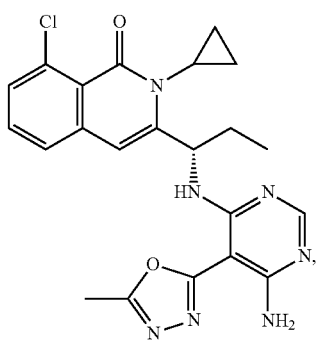 [SMILES: CC[C@H](Nc1ncnc(N)c1-c1nnc(C)o1)c1cc2cccc(Cl)c2c(=O)n1C1CC1] (10)
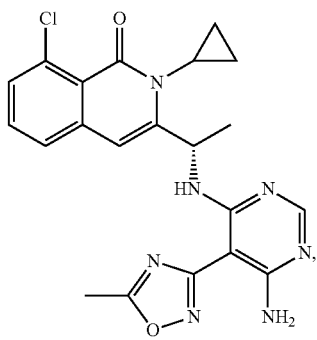 [SMILES: Cc1nc(-c2c(N)ncnc2N[C@@H](C)c2cc3cccc(Cl)c3c(=O)n2C2CC2)no1] (11)
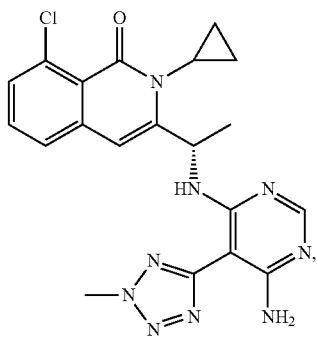 [SMILES: C[C@H](Nc1ncnc(N)c1-c1nnn(C)n1)c1cc2cccc(Cl)c2c(=O)n1C1CC1] (12)
TABLE 1-continued
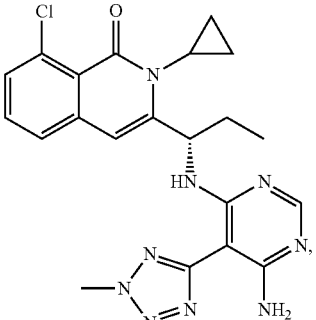 (13)
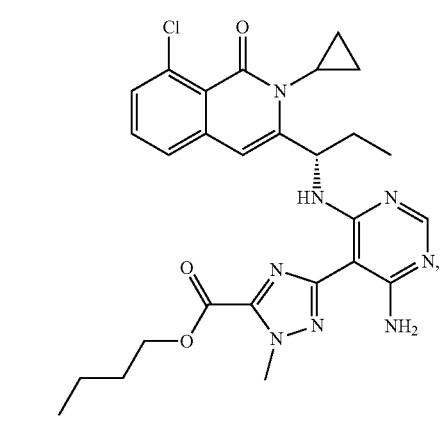 [SMILES: CCCCOC(=O)c1nc(-c2c(N)ncnc2N[C@@H](CC)c2cc3cccc(Cl)c3c(=O)n2C2CC2)nn1C] (14)
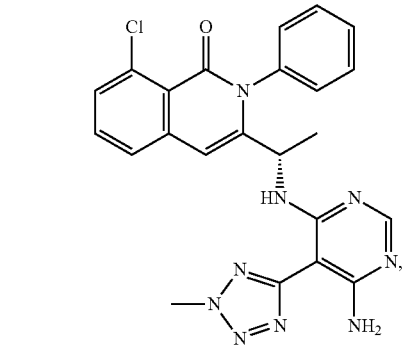 [SMILES: C[C@H](Nc1ncnc(N)c1-c1nnn(C)n1)c1cc2cccc(Cl)c2c(=O)n1-c1ccccc1] (15)
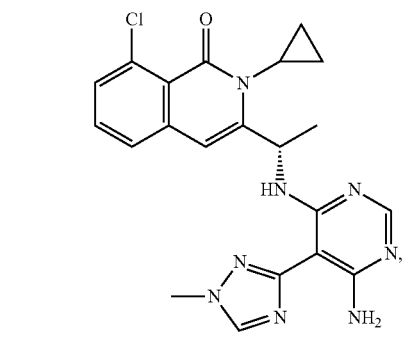 [SMILES: C[C@H](Nc1ncnc(N)c1-c1ncn(C)n1)c1cc2cccc(Cl)c2c(=O)n1C1CC1] (16)

TABLE 1-continued
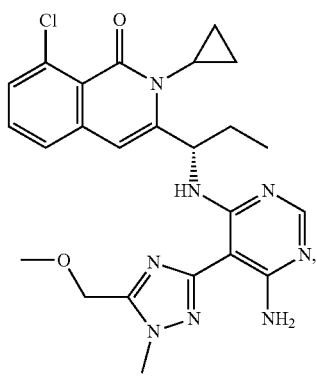 [SMILES: CC[C@H](Nc1ncnc(N)c1-c1nc(COC)n(C)n1)c1cc2cccc(Cl)c2c(=O)n1C1CC1] (17)
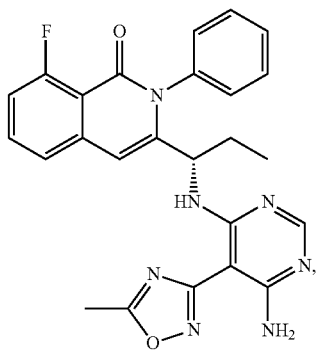 [SMILES: CC[C@H](Nc1ncnc(N)c1-c1noc(C)n1)c1cc2cccc(F)c2c(=O)n1-c1ccccc1] (18)
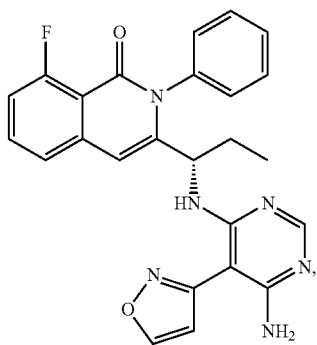 [SMILES: CC[C@H](Nc1ncnc(N)c1-c1ccon1)c1cc2cccc(F)c2c(=O)n1-c1ccccc1] (19)
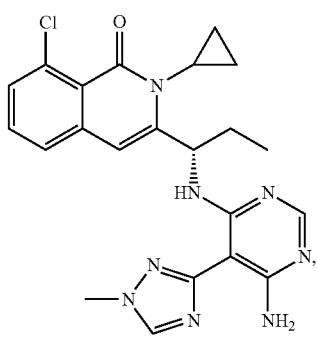 [SMILES: CC[C@H](Nc1ncnc(N)c1-c1ncn(C)n1)c1cc2cccc(Cl)c2c(=O)n1C1CC1] (20)
TABLE 1-continued
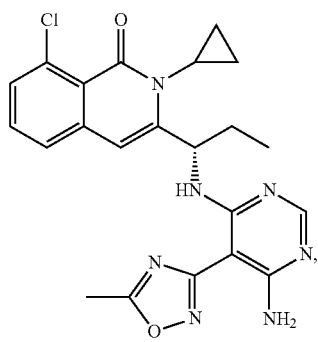 [SMILES: CC[C@H](Nc1ncnc(N)c1-c1noc(C)n1)c1cc2cccc(Cl)c2c(=O)n1C1CC1] (21)
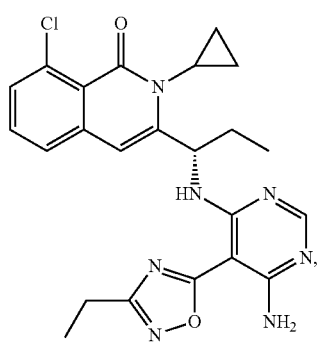 [SMILES: CCc1noc(-c2c(N)ncnc2N[C@@H](CC)c2cc3cccc(Cl)c3c(=O)n2C2CC2)n1] (22)
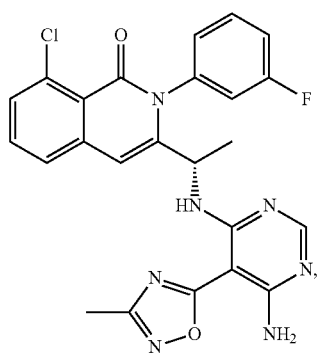 [SMILES: Cc1noc(-c2c(N)ncnc2N[C@@H](C)c2cc3cccc(Cl)c3c(=O)n2-c2cccc(F)c2)n1] (23)
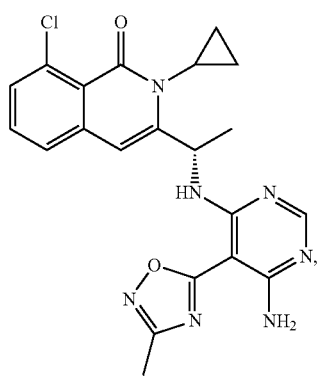 [SMILES: Cc1noc(-c2c(N)ncnc2N[C@@H](C)c2cc3cccc(Cl)c3c(=O)n2C2CC2)n1] (24)

TABLE 1-continued
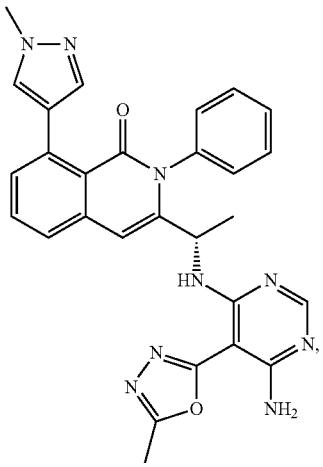 [SMILES: Cc1nnc(-c2c(N)ncnc2N[C@@H](C)c2cc3cccc(-c4cnn(C)c4)c3c(=O)n2-c2ccccc2)o1]
(25)
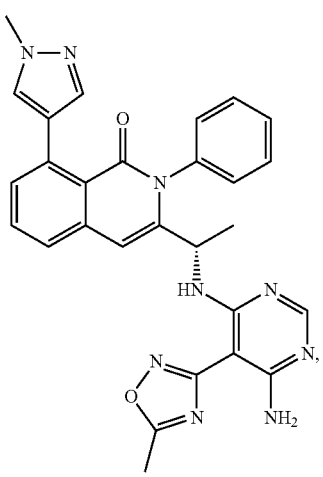 [SMILES: Cc1nc(-c2c(N)ncnc2N[C@@H](C)c2cc3cccc(-c4cnn(C)c4)c3c(=O)n2-c2ccccc2)no1]
(26)
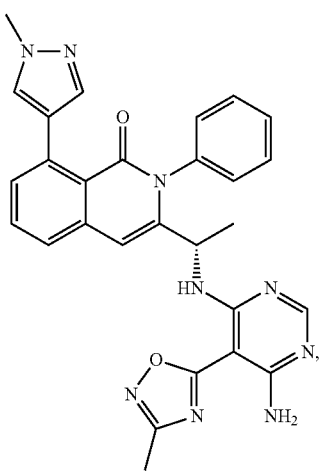 [SMILES: Cc1noc(-c2c(N)ncnc2N[C@@H](C)c2cc3cccc(-c4cnn(C)c4)c3c(=O)n2-c2ccccc2)n1]
(27)
TABLE 1-continued
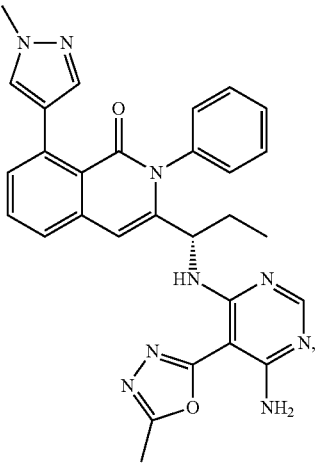 [SMILES: CC[C@H](Nc1ncnc(N)c1-c1nnc(C)o1)c1cc2cccc(-c3cnn(C)c3)c2c(=O)n1-c1ccccc1]
(28)
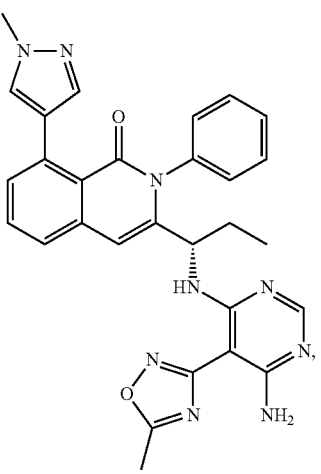 [SMILES: CC[C@H](Nc1ncnc(N)c1-c1noc(C)n1)c1cc2cccc(-c3cnn(C)c3)c2c(=O)n1-c1ccccc1]
(29)
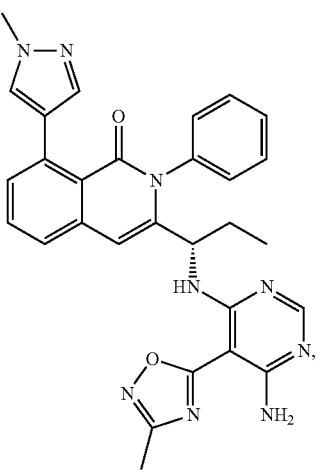 [SMILES: CC[C@H](Nc1ncnc(N)c1-c1nc(C)no1)c1cc2cccc(-c3cnn(C)c3)c2c(=O)n1-c1ccccc1]
(30)

TABLE 1-continued
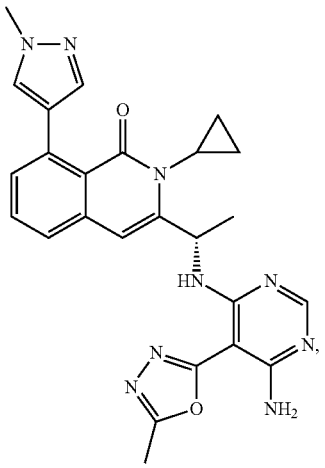 [SMILES: Cc1nnc(-c2c(N)ncnc2N[C@@H](C)c2cc3cccc(-c4cnn(C)c4)c3c(=O)n2C2CC2)o1]
(31)
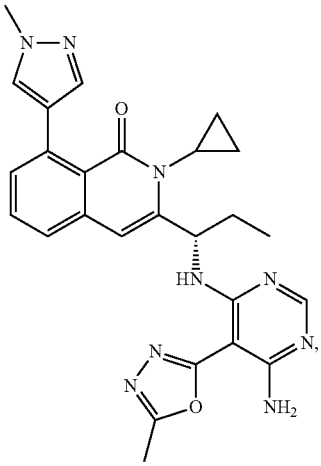
(34)
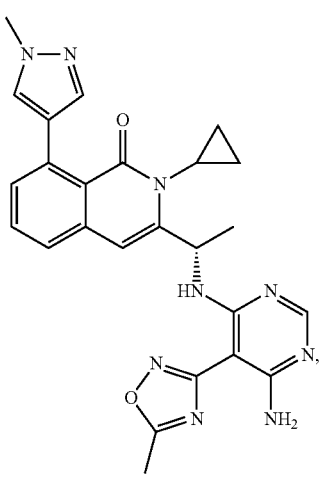 [SMILES: Cc1nc(-c2c(N)ncnc2N[C@@H](C)c2cc3cccc(-c4cnn(C)c4)c3c(=O)n2C2CC2)no1]
(32)
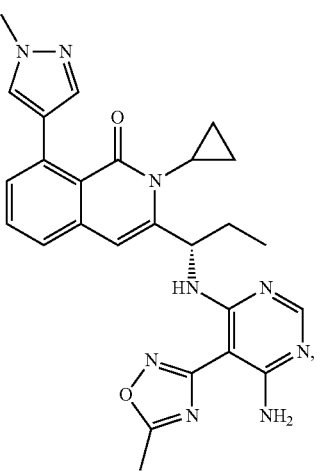
(35)
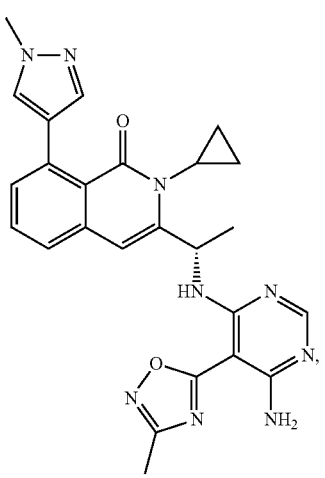 [SMILES: Cc1noc(-c2c(N)ncnc2N[C@@H](C)c2cc3cccc(-c4cnn(C)c4)c3c(=O)n2C2CC2)n1]
(33)
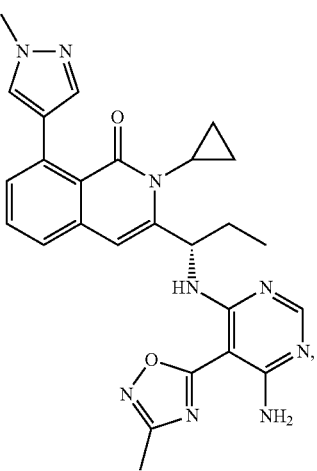 [SMILES: CC[C@H](Nc1ncnc(N)c1-c1nc(C)no1)c1cc2cccc(-c3cnn(C)c3)c2c(=O)n1C1CC1]
(36)

TABLE 1-continued

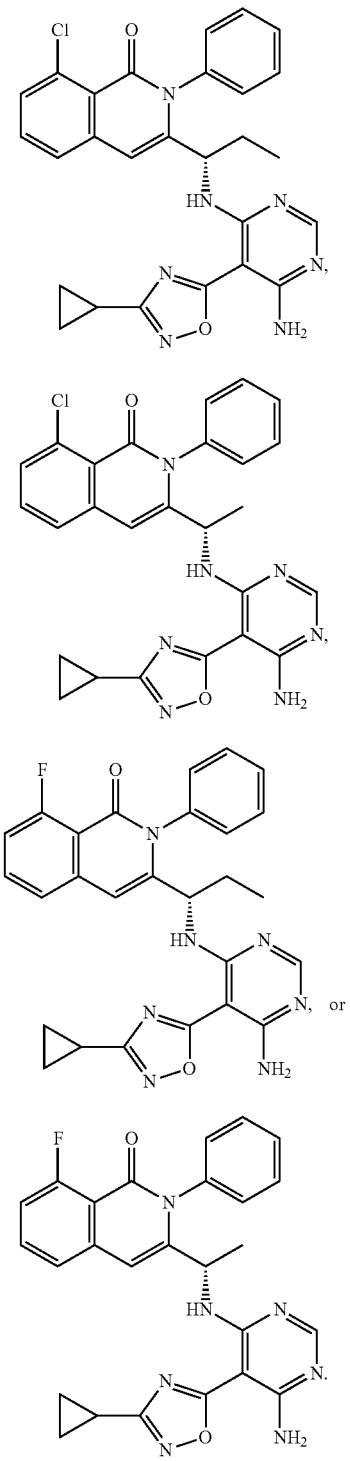

In one aspect of the invention, a pharmaceutical composition is provided which comprises a pharmaceutically acceptable carrier, excipient, diluent, adjuvant, vehicle or a combination thereof, and a compound of formula I or a pharmaceutically acceptable salt thereof. In some embodiments, the composition is a liquid, solid, semi-solid, gel, or an aerosol form.

In another aspect of the invention, a method of inhibiting a phosphatidyl inositol-3 kinase (PI3 kinase), is provided comprising: contacting the PI3 kinase with an effective amount of a compound disclosed herein. In some embodiments, the step of contacting comprises contacting a cell that contains said PI3 kinase. In some embodiments of the method, the inhibition takes place in a subject suffering from a disorder associated with malfunctioning of one or more types of PI3 kinase. Some exemplary diseases involving malfunctioning of one or more types of PI3 kinases are selected from the group consisting of autoimmune diseases, rheumatoid arthritis, respiratory disease, allergic reactions, and various types of cancers.

In some embodiments, the method comprises administering a second therapeutic agent to the subject.

In certain embodiments, the PI3K-mediated condition or disorder is selected from rheumatoid arthritis, ankylosing spondylitis, osteoarthritis, psoriatic arthritis, psoriasis, inflammatory diseases, and autoimmune diseases. In other embodiments, the PI3K-mediated condition or disorder is selected from cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease. In still other embodiments, the PI3K-mediated condition or disorder is selected from cancer, colon cancer, glioblastoma, endometrial carcinoma, hepatocellular cancer, lung cancer, melanoma, renal cell carcinoma, thyroid carcinoma, cell lymphoma, lymphoproliferative disorders, small cell lung cancer, squamous cell lung carcinoma, glioma, breast cancer, prostate cancer, ovarian cancer, cervical cancer, and leukemia. In yet another embodiment, the PI3K-mediated condition or disorder is selected from type II diabetes. In still other embodiments, the PI3K-mediated condition or disorder is selected from respiratory diseases, bronchitis, asthma, and chronic obstructive pulmonary disease. In certain embodiments, the subject is a human.

Another aspect of the invention relates to the treatment of PI3K-mediated condition or disorder in a patient comprising the step of administering a compound according to any of the above embodiments.

Another aspect of the invention relates to the treatment of rheumatoid arthritis, ankylosing spondylitis, osteoarthritis, psoriatic arthritis, psoriasis, inflammatory diseases or autoimmune diseases in a patient comprising the step of administering a compound according to any of the above embodiments.

Another aspect of the invention relates to the treatment of respiratory diseases including asthma, chronic obstructive pulmonary disease (COPD) and idiopathic pulmonary fibrosis (IPF) in a patient comprising the step of administering a compound according to any of the above embodiments.

Another aspect of the invention relates to the treatment of inflammatory bowel disorders, inflammatory eye disorders, inflammatory or unstable bladder disorders, skin complaints with inflammatory components, chronic inflammatory conditions, systemic lupus erythematosis (SLE), myestenia gravis, acute disseminated encephalomyelitis, idiopathic thrombocytopenic purpura, multiples sclerosis, Sjoegren's syndrome and autoimmune hemolytic anemia, allergic conditions and hypersensitivity in a patient, comprising the step of administering a compound according to any of the above or below embodiments.

Another aspect of the invention relates to the treatment of cancers in a patient that are mediated, dependent on or associated with PI3K activity, particularly PI3Kdelta activity, comprising the step of administering a compound according to any of the above or below embodiments.

Another aspect of the invention relates to the treatment of cancers are selected from acute myeloid leukaemia, myelodysplastic syndrome, myeloproliferative diseases, chronic myeloid leukaemia, T-cell acute lymphoblastic leukaemia, B-cell acute lymphoblastic leukaemia, non-hodgkins lymphoma, B-cell lymphoma, solid tumors and breast cancer, comprising the step of administering a compound according to any of the above or below embodiments.

Another aspect of the invention relates to the use of a compound according to any of the above embodiments as a medicament.

Another aspect of the invention relates to the use of a compound according to any of the above embodiments in the manufacture of a medicament for the treatment of PI3K-mediated condition or disorder in a patient.

Another aspect of the invention relates to the use of a compound according to any of the above embodiments in the manufacture of a medicament for the treatment of rheumatoid arthritis, ankylosing spondylitis, osteoarthritis, psoriatic arthritis, psoriasis, inflammatory diseases, respiratory diseases including asthma, chronic obstructive pulmonary disease (COPD) and idiopathic pulmonary fibrosis (IPF), autoimmune diseases, and cancers.

Unless otherwise stated, all stereoisomers, geometric isomers, tautomers, solvates, hydrates, metabolites, salts, and pharmaceutically acceptable prodrugs of the compounds disclosed herein are within the scope of the invention.

In certain embodiments, the salt is a pharmaceutically acceptable salt. The phrase "pharmaceutically acceptable" indicates that the substance or composition must be compatible chemically and/or toxicologically, with the other ingredients comprising a formulation, and/or the mammal being treated therewith.

The compounds of the invention also include salts of such compounds which are not necessarily pharmaceutically acceptable salts, and which may be useful as intermediates for preparing and/or purifying compounds of Formula (I) and/or for separating enantiomers of compounds of Formula (I).

Pharmaceutically acceptable acid addition salts can be formed with inorganic acids and organic acids, e.g., acetate, aspartate, benzoate, besylate, bromidehydrobromide, bicarbonatecarbonate, bisulfatesulfate, camphorsulfonate, chloridehydrochloride, chlortheophyllonate, citrate, ethandisulfonate, fumarate, gluceptate, gluconate, glucuronate, hippurate, hydroiodideiodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphated/hydrogen phosphate, polygalacturonate, propionate, stearate, succinate, subsalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts disclosed herein can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences," 20th ed., Mack Publishing Company, Easton, Pa., 1985; and in "Handbook of Pharmaceutical Salts: Properties, Selection, and Use" by Stahl and Wermuth, Wiley-VCH, Weinheim, Germany, 2002.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms.

In another aspect, provided herein are methods of preparing, methods of separating, and methods of purifying compounds of Formula (I). The compounds of the present invention may have in general several asymmetric centers and are typically depicted in the form of racemic mixtures. This invention is intended to encompass racemic mixtures, partially racemic mixtures and separate enantiomers and diasteromers.

Compounds of the present invention can be in the form of one of the possible isomers, rotamers, atropisomers, tautomers or mixtures thereof. This invention is intended to encompass mixtures of isomers, rotamers, atropisomers, tautomers, partially mixed isomers, rotamers, atropisomers, or tautomers, and separated isomers, rotamers, atropisomers, tautomers.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}P$, $^{36}Cl$, and $^{125}I$ respectively.

In another aspect, the compounds of the invention include isotopically labeled compounds as defined herein, for example those into which radioactive isotopes, such as $^{3}H$, $^{14}C$ and $^{18}F$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. D$_2$O, acetone-d$_6$, or DMSO-d$_6$.

Composition, Formulations and Administration of the Compounds Disclosed Herein

In one aspect, featured herein are pharmaceutical compositions that include a compound of formula (I), or a compound listed in Table 1; and a pharmaceutically acceptable carrier, adjuvant, or vehicle. The amount of compound in the pharmaceutical compositions disclosed herein is such that is effective to detectably inhibit a protein kinase in a biological sample or in a patient.

It will also be appreciated that certain of the compounds disclosed herein can exist in free form for treatment, or where appropriate, as a pharmaceutically acceptable derivative thereof. Some non-limiting examples of pharmaceutically acceptable derivative include pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As described above, the pharmaceutical compositions or pharmaceutically acceptable compositions disclosed herein additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds disclosed herein, such as by producing any undesirable biological effect or otherwise interacting in a deleterious manner with any other component(s) of the pharmaceutically acceptable composition, its use is contemplated to be within the scope of this invention.

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups. Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.5 mg to 1 g, or from 1 mg to 700 mg, or from 5 mg to 100 mg of a compound of formula (I) or a pharmaceutically acceptable salt thereof.

The pharmaceutical compositions of the invention typically contain one compound of formula (I) or a pharmaceutically acceptable salt thereof.

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formula (I) or a pharmaceutically acceptable salt thereof when administered to a patient and interactions which would result in pharmaceutical compositions that are not pharmaceutically acceptable are avoided. In addition, each excipient must of course be pharmaceutically-acceptable eg of sufficiently high purity. The compound of formula (I) or a pharmaceutically acceptable salt thereof and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The pharmaceutical compositions of the invention are prepared using techniques and methods known to those skilled in the art. Some of the methods commonly used in the art are described in Remington's Pharmaceutical Sciences (Mack Publishing Company).

Accordingly, in another aspect the invention is directed to process for the preparation of a pharmaceutical composition comprising a compound of formula (I) or a pharmaceutically acceptable salt thereof and one or more pharmaceutically acceptable excipients which comprises mixing the ingredients. A pharmaceutical composition comprising a compound of formula (I) or a pharmaceutically acceptable salt thereof may be prepared by, for example, admixture at ambient temperature and atmospheric pressure.

In one embodiment, the compounds of formula (I) or pharmaceutically acceptable salts thereof will be formulated for oral administration. In another embodiment, the compounds of formula (I) or pharmaceutically acceptable salts thereof will be formulated for inhaled administration. In a further embodiment, the compounds of formula (I) or pharmaceutically acceptable salts thereof will be formulated for intranasal administration.

In one aspect, the invention is directed to a solid oral dosage form such as a tablet or capsule comprising a safe and effective amount of a compound of formula (I) or a pharmaceutically acceptable salt thereof and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The compounds of formula (I) or pharmaceutically acceptable salts thereof may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of formula (I) or pharmaceutically acceptable salts thereof may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a compound of formula (I) or a pharmaceutically acceptable salt thereof. Syrups can be prepared by dissolving the compound of formula (I) or a pharmaceutically acceptable salt thereof in a suitably flavored aqueous solution, while elixirs are prepared through the use of a non-toxic alcoholic vehicle. Suspensions can be formulated by dispersing the compound of formula (I) or a pharmaceutically acceptable salt thereof in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

In another aspect, the invention is directed to a dosage form adapted fix administration to a patient by inhalation, for example as a dry powder, an aerosol, a suspension, or a solution composition. In one embodiment, the invention is directed to a dosage form adapted for administration to a patient by inhalation as a dry powder. In a further embodiment, the invention is directed to a dosage form adapted for administration to a patient by inhalation via a nebulizer. Dry powder compositions for delivery to the lung by inhalation typically comprise a compound of formula (I) or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (eg micronised) compound can be defined by a $D_{50}$ value of about 1 to about 10 microns (for example as measured using laser diffraction).

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation.

Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 20 μg-10 mg of the compound of formula (I) or a pharmaceutically acceptable salt thereof.

Aerosols may be formed by suspending or dissolving a compound of formula (I) or a pharmaceutically acceptable salt thereof in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (I) or a pharmaceutically acceptable salt thereof will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

There is thus provided as a further aspect of the invention a pharmaceutical aerosol formulation comprising a compound of formula (I) or a pharmaceutically acceptable salt thereof and a fluorocarbon or hydrogen-containing chlorofluorocarbon as propellant, optionally in combination with a surfactant and/or a cosolvent.

According to another aspect of the invention, there is provided a pharmaceutical aerosol formulation wherein the propellant is selected from 1,1,1,2-tetrafluoroethane, 1,1,1,2,3,3,3-heptafluoro-n-propane and mixtures thereof.

The formulations of the invention may be buffered by the addition of suitable buffering agents.

Capsules and cartridges for use in an inhaler or insufflator, of for example gelatine, may be formulated containing a powder mix for inhalation of a compound of formula (I) or a pharmaceutically acceptable salt thereof and a suitable powder base such as lactose or starch. Each capsule or cartridge may generally contain from 20 μg to 10 mg of the compound of formula (I) or pharmaceutically acceptable salt thereof. Alternatively, the compound of formula (I) or pharmaceutically acceptable salt thereof may be presented without excipients such as lactose.

The proportion of the active compound of formula (I) or pharmaceutically acceptable salt thereof in the local compositions according to the invention depends on the precise type of formulation to be prepared but will generally be within the range of from 0.001 to 10% by weight. Generally, for most types of preparations, the proportion used will be within the range of from 0.005 to 1%, for example from 0.01 to 0.5%. However, in powders for inhalation or insufflation the proportion used will normally be within the range of from 0.1% to 5%.

Aerosol formulations are preferably arranged so that each metered dose or "puff" of aerosol contains from 20 μg to 10 mg, preferably from 20 μg to 2000 μg, more preferably from about 20 μg to 500 μg of a compound of formula (I). Administration may be once daily or several times daily, for example 2, 3, 4 or 8 times, giving for example 1, 2 or 3 doses each time. The overall daily dose with an aerosol will be within the range from 100 μg to 10 mg, preferably from 200 μg to 2000 μg. The overall daily dose and the metered dose delivered by capsules and cartridges in an inhaler or insufflator will generally be double that delivered with aerosol formulations.

In the case of suspension aerosol formulations, the particle size of the particulate (e.g., micronised) drug should be such as to permit inhalation of substantially all the drug into the lungs upon administration of the aerosol formulation and will thus be less than 100 microns, desirably less than 20 microns, and in particular in the range of from 1 to 10 microns, such as from 1 to 5 microns, more preferably from 2 to 3 microns.

The formulations of the invention may be prepared by dispersal or dissolution of the medicament and a compound of formula (I) or a pharmaceutically acceptable salt thereof in the selected propellant in an appropriate container, for example, with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The stability of the suspension aerosol formulations according to the invention may be measured by conventional techniques, for example, by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopeia 1988, pages A204-207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above.

The term "metered dose inhaler" or MDI means a unit comprising a can, a secured cap covering the can and a formulation metering valve situated in the cap, MDI system includes a suitable channeling device. Suitable channeling devices comprise for example, a valve actuator and a cylindrical or cone-like passage through which medicament may be delivered from the filled canister via the metering valve to the nose or mouth of a patient such as a mouthpiece actuator.

MIDI canisters generally comprise a container capable of withstanding the vapour pressure of the propellant used such as a plastic or plastic-coated glass bottle or preferably a metal can, for example, aluminium or an alloy thereof which may optionally be anodised, lacquer-coated and/or plastic-coated (for example incorporated herein by reference WO 96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g. see Byron, above and WO 96/32099). Preferably the canister is fitted with a cap assembly, wherein a drug-metering valve is situated in the cap, and said cap is crimped in place.

In one embodiment of the invention the metallic internal surface of the can is coated with a fluoropolymer, more preferably blended with a non-fluoropolymer. In another embodiment of the invention the metallic internal surface of the can is coated with a polymer blend of polytetrafluoroethylene (PTFE) and polyethersulfone (PES). In a further embodiment of the invention the whole of the metallic internal surface of the can is coated with a polymer blend of polytetrafluoroethylene (PTFE) and polyethersulfone (PES). The metering valves are designed to deliver a metered amount of the formulation per actuation and incorporate a gasket to prevent leakage of propellant through the valve. The gasket may comprise any suitable elastomeric material such as, fix example, low density polyethylene, chlorobutyl, bromobutyl, EPDM, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak pie, UK (e.g. BK300, BK357) and 3M-™ Neotechnic Ltd, UK (e.g. Spraymiser).

In various embodiments, the MDIs may also be used in conjunction with other structures such as, without limitation, overwrap packages for storing and containing the MDIs, including those described in U.S. Pat. Nos. 6,119,853; 6,179,118; 6,315,112; 6,352,152; 6,390,291; and 6,679,374, as well as dose counter units such as, but not limited to, those described in U.S. Pat. Nos. 6,360,739 and 6,431,168.

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method for preparing suspension aerosol formulations a metering valve is crimped onto an aluminium can to form an empty canister. The particulate medicament is added to a charge vessel and liquefied propellant together with the optional excipients is pressure fitted through the charge vessel into a manufacturing vessel. The drug suspension is mixed before recirculation to a filling machine and an aliquot of the drug suspension is then filled through the metering valve into the canister. In one example bulk manufacturing method for preparing solution aerosol formulations a metering valve is crimped onto an aluminium can to form an empty canister. The liquefied propellant together with the optional excipients and the dissolved medicament is pressure filled through the charge vessel into a manufacturing vessel.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing. Suspensions and solutions comprising a compound of formula (I) or a pharmaceutically acceptable salt thereof may also be administered to a patient via a nebulizer. The solvent or suspension agent utilized for nebulization may be any pharmaceutically-acceptable liquid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically-acceptable excipients may be added to the suspension or solution. The compound of formula (I) or pharmaceutically acceptable salt thereof may be stabilized by the addition of an inorganic acid, e.g., hydrochloric acid, nitric acid, sulphuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of formula (I) or pharmaceutically acceptable salt thereof. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

In a further aspect, the invention is directed to a dosage form adapted for intranasal administration.

Formulations for administration to the nose may include pressurised aerosol formulations and aqueous formulations administered to the nose by pressurised pump. Formulations which are non-pressurised and adapted to be administered topically to the nasal cavity are of particular interest. Suitable formulations contain water as the diluent or carrier for this purpose. Aqueous formulations for administration to the lung or nose may be provided with conventional excipients such as buffering agents, tonicity modifying agents and the like. Aqueous formulations may also be administered to the nose by nebulisation. The compounds of formula (I) or pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user fix spray dispensing of the fluid formulation into the nasal cavity. A fluid dispenser of the aforementioned type is described and illustrated in WO 05/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. In one embodiment, the fluid dispenser is of the general type illustrated in FIGS. 30-40 of WO 05/044354.

Pharmaceutical compositions adapted for intranasal administration wherein the carrier is a solid include a coarse powder having a particle size for example in the range 20 to 500 microns which is administered by rapid inhalation through the nasal passage from a container of the powder held close up to the nose. Suitable compositions wherein the carrier is a liquid, for administration as a nasal spray or as nasal drops, include aqueous or oil solutions of the compound of formula (I) or a pharmaceutically acceptable salt thereof.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils. Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Topical preparations may be administered by one or more applications per day to the affected area; over skin areas occlusive dressings may advantageously be used. Continuous or prolonged delivery may be achieved by an adhesive reservoir system.

For treatments of the eye or other external tissues, for example mouth and skin, the compositions may be applied as a topical ointment or cream. When formulated in an ointment, the compound of formula (I) or a pharmaceutically acceptable salt thereof may be employed with either a paraffinic or a water-miscible ointment base. Alternatively, the compound of formula (I) or pharmaceutically acceptable salt thereof may be formulated in a cream with an oil-in-water cream base or a water-in-oil base.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The compound and pharmaceutical formulations according to the invention may be used in combination with or include one or more other therapeutic agents, for example selected from anti-inflammatory agents, anticholinergic agents (particularly an $M_1/M_2/M_3$ receptor antagonist), $\beta_2$-adrenoreceptor agonists, antiinfective agents, such as antibiotics or antivirals, or antihistamines. The invention thus provides, in a further aspect, a combination comprising a compound of formula (I) or a pharmaceutically acceptable salt thereof together with one or more other therapeutically active agents, for example selected from an anti-inflammatory agent, such as a corticosteroid or an NSAID, an anticholinergic agent, a $\beta_2$-adrenoreceptor agonist, an anti-infective agent, such as an antibiotic or an antiviral, or an antihistamine. One embodiment of the invention encompasses combinations comprising a compound of formula (I) or a pharmaceutically acceptable salt thereof together with a $\beta_2$-adrenoreceptor agonist, and/or an anticholinergic, and/or a PDE-4 inhibitor, and/or an antihistamine.

In one embodiment, the invention encompasses a method of treating a disorder mediated by inappropriate PI3-kinase activity comprising administering a safe and effective amount of a combination comprising a compound of formula (I) or a pharmaceutically acceptable salt thereof together with one or more therapeutically active agents.

Certain compounds of the invention may show selectivity for PI3Kδ over other PI3-kinases. The invention thus provides, in a further aspect, a combination comprising a compound of formula (I) or a pharmaceutically acceptable salt thereof which is selective for PI3Kδ together with a compound or pharmaceutically acceptable salt thereof which is selective for another PI3-kinase, for example PI3γ.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimise the activity and/or stability and/or physical characteristics, such as solubility, of the therapeutic ingredient. It will be clear also that, where appropriate, the therapeutic ingredients may be used in optically pure form.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by the activity of the PI3K enzymes. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, fix example, oral and parenteral, fix administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by the activity of the PI3K enzymes, wherein the medicament is prepared for administration with another therapeutic agent. The invention also provides the use of another therapeutic agent for treating a disease or condition mediated by the activity of the PI3K enzymes, wherein the medicament is administered with a compound of formula (I).

The invention also provides a compound of formula (I) for use in a method of treating a disease or condition mediated by the activity of the PI3K enzymes, wherein the compound of formula (I) is prepared for administration with another therapeutic agent. The invention also provides another therapeutic agent for use in a method of treating a disease or condition mediated by the activity of the PI3K enzymes, wherein the other therapeutic agent is prepared for administration with a compound of formula (I). The invention also provides a compound of formula (I) for use in a method of treating a disease or condition mediated by the activity of the PI3K enzymes wherein the compound of formula (I) is administered with another therapeutic agent. The invention also provides another therapeutic agent for use in a method of treating a disease or condition mediated by the activity of the PI3K enzymes wherein the other therapeutic agent is administered with a compound of formula (I).

The invention also provides the use of a compound of formula (I) for treating a disease or condition mediated by the activity of the PI3K enzymes, wherein the patient has previously (e.g. within 24 hours) been treated with another therapeutic agent. The invention also provides the use of another therapeutic agent for treating a disease or condition mediated by the activity of the PI3K enzymes, wherein the patient has previously (e.g. within 24 hours) been treated with a compound of formula (I). The compounds of formula I may be administered as the sole active ingredient or in conjunction with, e.g. as an adjuvant to, other drugs e.g. immunosuppressive or immunomodulating agents or other anti-inflammatory agents, e.g. for the treatment or prevention of alio- or xenograft acute or chronic rejection or inflammatory or autoimmune disorders, or a chemotherapeutic agent, e.g a malignant cell anti-proliferative agent. For example, the compounds of formula I may be used in combination with a calcineurin inhibitor, e.g. cyclosporin A or FK 506; a mTOR inhibitor, e.g. rapamycin, 40-O-(2-hydroxyethyl)rapamycin, CCI779, ABT578, AP23573, TAFA-93, biolimus-7 or biolimus-9; an ascormycin having immuno-suppressive properties, e.g. ABT-281, ASM981, etc.; corticosteroids; cyclophosphamide; azathioprene; methotrexate; leflunomide; raizoribine; mycophenolic acid or salt; mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; a JAK3 kinase inhibitor, e.g. N-benzyl-3,4-dihydroxy-benzylidene-cyanoacetamide-α-cyano-(3,4-dihydroxy)-N-benzylcinnamamide (Tyrphostin AG 490), prodigiosin 25-C (PNU156804), [4-(4'-hydroxyphenyl)-amino-6,7-dimethoxyquinazoline] (WHI-P131), [4-(3-bromo-4-hydroxylphenyl)-amino-6,7-dimethoxyquinazoline] (WHI-P154), [4-(3',5'-dibromo-4'-hydroxylphenyl)-amino-6,7-dimethoxyquinazoline] WHI-P97, KRX-21, 1,3-{(3R,4R)-4-methyl-3-[methyl-(7H-pyrrolo[2,3]-d]pyrimidin-4-yl)-aminol-piperidin-1-yl}-3-oxo-propionitrile, in free form or in a pharmaceutically acceptable salt form, e.g. mono-citrate (also called CP-690,550), or a compound as disclosed in WO 04/052359 or WO 05/066156; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig ((or ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or antihistamines; or antitussives, or a bronchodilatory agent; or an angiotensin receptor blockers; or an anti-infectious agent.

Where the compounds of formula (I) are administered in conjunction with other immunosuppressive/immunomodulatory, anti-inflammatory, chemotherapeutic or anti-infectious therapy, dosages of the co-administered immunosuppressant, immunomodulatory, anti-inflammatory, chemotherapeutic or anti-infectious compound will of course vary depending on the type of co-drug employed, e.g. whether it is a steroid or a calcineurin inhibitor, on the specific drug employed, on the condition being treated and so forth.

In one embodiment, the invention encompasses a combination comprising a compound of formula (I) or a pharmaceutically acceptable salt thereof together with a $\beta_2$-adrenoreceptor agonist.

Examples of $\beta_2$-adrenoreceptor agonists include salmeterol (which may be a racemate or a single enantiomer such as the R-enantiomer), salbutamol (which may be a racemate or a single enantiomer such as the R-enantiomer), formoterol (which may be a racemate or a single duastereomer such as the R,R-diastereomer), salmefamol, fenoterol, carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment, tong-acting β$_2$-adrenoreceptor agonists, for example, compounds which provide effective bronchodilation for about 12 hrs or longer, are preferred.

The β$_2$-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, naphthaleneacrylic, benzoic, 4-methoxybenzoic, 2- or 4-hydroxybenzoic, 4-chlorobenzoic and 4-phenylbenzoic acid.

Suitable antiinflammatory agents include corticosteroids. Suitable corticosteroids which may be used in combination with the compounds of formula (I) or pharmaceutically acceptable salts thereof are those oral and inhaled corticosteroids and their pro-drugs which have antiinflammatory activity. Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-ethycyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid 5-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Non-steroidal compounds having glucocorticoid agonism that may possess selectivity for transrepression over transactivation and that may be useful in combination therapy include those covered in the following patents: WO 03/082827, WO 98/54159, WO 04/005229, WO 04/009017, WO 04/018429, WO 03/104195, WO 03/082787, WO 03/082280, WO 03/059899, WO 03/101932, WO 02/02565, WO 01/16128, WO 00/66590, WO 03/086294, WO 04/026248, WO 03/061651 and WO 03/08277. Further non-steroidal compounds are covered in: WO 2006/000401, WO 2006/000398 and WO 2006/015870.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a COO antagonist) or inhibitors of cytokine synthesis, or 5-lipoxygenase inhibitors. An iNOS (inducible nitric oxide synthase inhibitor) is preferably for oral administration. Examples of iNOS inhibitors include those disclosed in WO 93/13055, WO 98/30537, WO 02/50021, WO 95/34534 and WO 99/62875, Examples of CCR3 inhibitors include those disclosed in WO 02/26722.

In one embodiment, the invention provides the use of the compounds of formula (I) in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4. Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical firms, which is described in U.S. Pat. No. 5,552,438 issued 3 Sep. 1996; this patent and the compounds it discloses are incorporated herein in full by reference.

Examples of anticholinergic agents are those compounds that act as antagonists at the muscarinic receptors, in particular those compounds which are antagonists of the M$_1$ or M$_3$ receptors, dual antagonists of the M$_1$/M$_3$ or M$_2$/M$_3$, receptors or pan-antagonists of the M$_1$/M$_2$/M$_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO 01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (for example, as the bromide, CAS 26095-59-0, sold under the name Spasmomen), trospium chloride (CAS 10405-02-4) and solifenacin (GAS 242478-37-1, or GAS 242478-38-2 for the succinate also known as YM-905 and sold under the name Vesicare).

In one embodiment the invention provides a combination comprising a compound of formula (I) or a pharmaceutically acceptable salt thereof together with an H1 antagonist. Some non-limiting examples of the H1 antagonist include amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In a further embodiment the invention provides a combination comprising a compound of formula (I) or a pharmaceutically acceptable salt thereof together with an H3 antagonist (and/or inverse agonist). Examples of H3 antagonists include, for example, those compounds disclosed in WO 2004/035556 and in WO 2006/045416. Other histamine receptor antagonists which may be used in combination with the compounds of the present invention include antagonists (and/or inverse agonists) of the 1-14 receptor, for example, the compounds disclosed in Jablonowski et al., *J. Med. Chem.*, 2003, 46, 3957-3960.

The invention thus provides, in a further aspect, a combination comprising a compound of formula (I) or a pharmaceutically acceptable salt thereof together with a PDE4 inhibitor.

The invention thus provides, in a further aspect, a combination comprising a compound of formula (I) or a pharmaceutically acceptable salt thereof together with a $\beta_2$-adrenoreceptor agonist.

The invention thus provides, in a further aspect, a combination comprising a compound of formula (I) or a pharmaceutically acceptable salt thereof together with a corticosteroid.

The invention thus provides, in a further aspect, a combination comprising a compound of formula (I) or a pharmaceutically acceptable salt thereof together with a non-steroidal GR agonist.

The invention thus provides, in a further aspect, a combination comprising a compound of formula (I) or a pharmaceutically acceptable salt thereof together with an anticholinergic.

The invention thus provides, in a further aspect, a combination comprising a compound of formula (I) or a pharmaceutically acceptable salt thereof together with an antihistamine.

The invention thus provides, in a further aspect, a combination comprising a compound of formula (I) or a pharmaceutically acceptable salt thereof together with a PDE4 inhibitor and a $\beta_2$-adrenoreceptor agonist.

The invention thus provides, in a further aspect, a combination comprising a compound of formula (I) or a pharmaceutically acceptable salt thereof together with an anticholinergic and a PDE-4 inhibitor.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of a compound of formula (I) or a pharmaceutically acceptable salt thereof together with another therapeutically active agent.

The invention thus provides, in a further aspect, a pharmaceutical composition comprising a combination of a compound of formula (I) or a pharmaceutically acceptable salt thereof together with a PDE4 inhibitor.

The invention thus provides, in a further aspect, a pharmaceutical composition comprising a combination of a compound of formula (I) or a pharmaceutically acceptable salt thereof together with a $\beta_2$-adrenoreceptor agonist.

The invention thus provides, in a further aspect, a pharmaceutical composition comprising a combination of a compound of formula (I) or a pharmaceutically acceptable salt thereof together with a corticosteroid.

The invention thus provides, in a further aspect, a pharmaceutical composition comprising a combination of a compound of formula (I) or a pharmaceutically acceptable salt thereof together with a non-steroidal GR agonist.

The invention thus provides, in a further aspect, a pharmaceutical composition comprising a combination of a compound of formula (I) or a pharmaceutically acceptable salt thereof together with an anticholinergic.

The invention thus provides, in a further aspect, a pharmaceutical composition comprising a combination of a compound of formula (I) or a pharmaceutically acceptable salt thereof together with an antihistamine.

The invention thus provides, in a further aspect, a pharmaceutical composition comprising a combination of a compound of formula (I) or a pharmaceutically acceptable salt thereof together with a PDE4 inhibitor and a $\beta_2$-adrenoreceptor agonist.

The invention thus provides, in a further aspect, a pharmaceutical composition comprising a combination of a compound of formula (I) or a pharmaceutically acceptable salt thereof together with an anticholinergic and a PDE4 inhibitor.

A compound of the formula (I) may also be used to advantage in combination with each other or in combination with other therapeutic agents, especially other antiproliferative agents. Such antiproliferative agents include, but are not limited to, aromatase inhibitors; antiestrogens; topoisomerase I inhibitors; topoisomerase II inhibitors; microtubule active agents; alkylating agents; histone deacetylase inhibitors; compounds, which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; antiandrogens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; agents used in the treatment of hematologic malignancies; compounds which target, decrease or inhibit the activity of Flt-3; Hsp90 inhibitors; temozolomide (TEMODAL®); and leucovorin.

The term "aromatase inhibitor", as used herein, relates to a compound which inhibits the estrogen production, i.e., the conversion of the substrates androstenedione and testosterone to estrone and estradiol, respectively. The term includes, but is not limited to, steroids, especially atamestane, exemestane and formestane; and, in particular, nonsteroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g., under the trademark AROMASIN. Formestane can be administered, e.g., in the form as it is marketed, e.g., under the trademark LENTARON. Fadrozole can be administered, e.g., in the form as it is marketed, e.g., under the trademark AFEMA. Anastrozole can be administered, e.g., in the form as it is marketed, e.g., under the trademark ARIMIDEX. Letrozole can be administered, e.g., in the form as it is marketed, e.g., under the trademark FEMARA or FEMAR. Aminoglutethimide can be administered, e.g., in the form as it is marketed, e.g., under the trademark ORIMETEN. A combination of the invention comprising a chemotherapeutic agent which is an aromatase inhibitor is particularly useful for the treatment of hormone receptor positive tumors, e.g., breast tumors.

The term "anti-estrogen", as used herein, relates to a compound which antagonizes the effect of estrogens at the estrogen receptor level. The term includes, but is not limited to, tamoxifen, fulvestrant, raloxifene and raloxifene hydrochloride. Tamoxifen can be administered, e.g., in the form as it is marketed, e.g., under the trademark NOLVADEX. Raloxifene hydrochloride can be administered, e.g., in the form as it is marketed, e.g., under the trademark EVISTA. Fulvestrant can be formulated as disclosed in U.S. Pat. No. 4,659,516 or it can be administered, e.g., in the form as it is marketed, e.g., under the trademark FASLODEX. A combination of the invention comprising a chemotherapeutic agent which is an antiestrogen is particularly useful for the treatment of estrogen receptor positive tumors, e.g., breast tumors.

The term "anti-androgen", as used herein, relates to any substance which is capable of inhibiting the biological effects of androgenic hormones and includes, but is not limited to, bicalutamide (CASODEX), which can be formulated, e.g., as disclosed in U.S. Pat. No. 4,636,505.

The term "gonadorelin agonist", as used herein, includes, but is not limited to, abarelix, goserelin and goserelin acetate. Goserelin is disclosed in U.S. Pat. No. 4,100,274 and can be administered, e.g., in the form as it is marketed, e.g., under the trademark ZOLADEX. Abarelix can be formulated, e.g., as disclosed in U.S. Pat. No. 5,843,901.

The term "topoisomerase I inhibitor", as used herein, includes, but is not limited to, topotecan, gimatecan, irinotecan, camptothecian and its analogues, 9-nitrocamptothecin and the macromolecular camptothecin conjugate PNU-166148 (compound A1 in WO 99/17804). Irinotecan can be administered, e.g., in the form as it is marketed, e.g., under the trademark CAMPTOSAR. Topotecan can be administered, e.g., in the form as it is marketed, e.g., under the trademark HYCAMTIN.

The term "topoisomerase II inhibitor", as used herein, includes, but is not limited to, the anthracyclines, such as doxorubicin, including liposomal formulation, e.g., CAELYX; daunorubicin; epirubicin; idarubicin; nemorubicin; the anthraquinones mitoxantrone and losoxantrone; and the podophillotoxines etoposide and teniposide. Etoposide can be administered, e.g., in the form as it is marketed, e.g., under the trademark ETOPOPHOS. Teniposide can be administered, e.g., in the form as it is marketed, e.g., under the trademark VM 26-BRISTOL. Doxortibicin can be administered, e.g., in the form as it is marketed, e.g., under the trademark ADRIBLASTIN or ADRIAMYCIN.

Epirubicin can be administered, e.g., in the form as it is marketed, e.g., under the trademark FARMORUBICIN. Idarubicin can be administered, e.g., in the form as it is marketed, e.g., under the trademark ZAVEDOS. Mitoxantrone can be administered, e.g., in the form as it is marketed, e.g., under the trademark NOVANTRON.

The term "microtubule active agent" relates to microtubule microtubule destabilizing agents and microtublin polymerization inhibitors including, but not limited to, taxanes, e.g., paclitaxel and docetaxel; vinca alkaloids, e.g., vinblastine, especially vinblastine sulfate; vincristine, especially vincristine sulfate and vinorelbine; discodermolides; cochicine; and epothilones and derivatives thereof, e.g., epothilone B or D or derivatives thereof. Paclitaxel may be administered, e.g., in the form as it is marketed, e.g., TAXOL. Docetaxel can be administered, e.g., in the form as it is marketed, e.g., under the trademark TAXOTERE. Vinblastine sulfate can be administered, e.g., in the form as it is marketed, e.g., under the trademark VINBLASTIN R.P. Vincristine sulfate can be administered, e.g., in the form as it is marketed, e.g., under the trademark FARMISTIN. Discodermolide can be obtained, e.g., as disclosed in U.S. Pat. No. 5,010,099. Also included are epothilone derivatives which are disclosed in WO 98/10121, U.S. Pat. No. 6,194,181, WO 98/25929, WO 98/08849, WO 99/43653, WO 98/22461 and WO 00/31247. Especially preferred are epothilone A and/or B.

The term "alkylating agent", as used herein, includes, but is not limited to, cyclophosphamide, ifosfamide, melphalan or nitrosourea (BCNU or Gliadel). Cyclophosphamide can be administered, e.g., in the form as it is marketed, e.g., under the trademark CYCLOSTIN. Ifosfamide can be administered, e.g., in the form as it is marketed, e.g., under the trademark HOLOXAN.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further especially includes suberoylanilide hydroxamic acid (SAHA).

The term "antineoplastic antimetabolite" includes, but is not limited to, 5-fluorouracil or 5-FU; capecitabine; gemcitabine; DNA demethylating agents, such as 5-azacytidine and decitabine; methotrexate and edatrexate; and folic acid antagonists, such as pemetrexed. Capecitabine can be administered, e.g., in the form as it is marketed, e.g., under the trademark XELODA. Gemcitabine can be administered, e.g., in the form as it is marketed, e.g., under the trademark GEMZAR. Also included is the monoclonal antibody trastuzumab which can be administered, e.g., in the form as it is marketed, e.g., under the trademark HERCEPTIN.

The term "platin compound", as used herein, includes, but is not limited to, carboplatin, cis-platin, cisplatinum and oxaliplatin. Carboplatin can be administered, e.g., in the form as it is marketed, e.g., under the trademark CARBOPLAT. Oxaliplatin can be administered, e.g., in the form as it is marketed, e.g., under the trademark ELOXATIN. The term "compounds targeting/decreasing a protein or lipid kinase activity; or a protein or lipid phosphatase activity; or further anti-angiogenic compounds", as used herein, includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g., a N-phenyl-2-pyrimidine-amine derivative, e.g., imatinib, SU101, SU6668 and GIB-111;

b) compounds targeting, decreasing or inhibiting the activity of the fibroblast growth factor-receptors (FGFR);

c) compounds targeting, decreasing or inhibiting the activity of the insulin-like growth factor receptor 1 (IGF-IR), such as compounds which target, decrease or inhibit the activity of IGF-IR, especially compounds which inhibit the IGF-IR receptor, such as those compounds disclosed in WO 02/092599;

d) compounds targeting, decreasing or inhibiting the activity of the Trk receptor tyrosine kinase family;

e) compounds targeting, decreasing or inhibiting the activity of the Axl receptor tyrosine kinase family;

f) compounds targeting, decreasing or inhibiting the activity of the c-Met receptor;

g) compounds targeting, decreasing or inhibiting the activity of the Kit/SCFR receptor tyrosine kinase;

h) compounds targeting, decreasing or inhibiting the activity of the C-kit receptor tyrosine kinases—(part of the PDGFR family), such as compounds which target, decrease or inhibit the activity of the c-Kit receptor tyrosine kinase family, especially compounds which inhibit the c-Kit receptor, e.g., imatinib;

i) compounds targeting, decreasing or inhibiting the activity of members of the c-Abl family and their gene-fusion products, e.g., BCR-Abl kinase, such as compounds which target decrease or inhibit the activity of c-Abl family members and their gene fusion products, e.g., a N-phenyl-2-pyrimidine-amine derivative, e.g., imatinib, PD180970, AG957, NSC 680410 or PD173955 from ParkeDavis; j) compounds targeting, decreasing or inhibiting the activity of members of the protein kinase C (PKC) and Raf family of serine/threonine kinases, members of the MEK, SRC, JAK, FAK, PDK and Ras/MAPK family members, or PI(3) kinase family, or of the PI(3)-kinase-related kinase family, and/or members of the cyclin-dependent kinase family (CDK) and are especially those staurosporine derivatives disclosed in U.S. Pat. No. 5,093,330, e.g., midostaurin; examples of further compounds include, e.g., UCN-01; safingol; BAY 43-9006; Bryostatin 1; Perifosine; llmofosine; RO 318220 and RO 320432; GO 6976; Isis 3521; LY333531/LY379196; isochinoline compounds, such as those disclosed in WO 00/09495; FT's; PD184352; or QAN697 (a PI3K inhibitor);

k) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemaionirile or bisubstrate quinoline class of compounds, more especially any compound selected from the group consisting of Tyrphostin A23/RG-50810, AG 99, Tyrphostin AG 213, Tyrphostin AG 1748, Tyrphostin AG 490, Tyrphostin B44, Tyrphostin B44 (+) enantiomer, Tyrphostin AG 555, AG 494, Tyrphostin AG 556, AG 957 and adaphostin (4-{[(2,5-dihydroxyphenyl)methyl]amino}-benzoic acid adamantyl ester, NSC 680410, adaphostin; and l) compounds targeting, decreasing or inhibiting the activity of the epidermal growth factor family of receptor tyrosine kinases (EGFR, ErbB2, ErbB3, ErbB4 as homo- or hetero-dimers), such as compounds which target, decrease or inhibit the activity of the epidermal growth factor receptor family are especially compounds, proteins or antibodies which inhibit members of the EGF receptor tyrosine kinase family, e.g., EGF receptor, ErbB2, ErbB3 and ErbB4 or bind to EGF or EGF related ligands, and are in particular those compounds, proteins or monoclonal antibodies generically and specifically disclosed in WO 97/02266, e.g., the compound of Example 39, or in EP 0 564 409; WO 99/03854; EP 0520722; EP 0 566 226; EP 0 787 722; EP 0 837 063; U.S. Pat. No. 5,747,498; WO 98/10767; WO 97/30034; WO 97/49688; WO 97/38983 and, especially, WO 96/30347, e.g., compound known as CP 358774; WO 96/33980, e.g., compound ZD 1839; and WO 95/03283, e.g., compound ZM105180, e.g., trastuzumab (HERCEPTIN), cetuximab, Iressa, Tarceva, OSI-774, CI-1033, EKB-569, GW-2016, E1.1, E2.4, E2.5, E6.2, E6.4, E2.11, E6.3 or E7.6.3; and 7H-pyrrolo-[2,3-d]pyrimidine derivatives which are disclosed in WO 03/013541. Further anti-angiogenic compounds include compounds having another mechanism for their activity, e.g., unrelated to protein or lipid kinase inhibition, e.g., thalidomide (THALOMID) and TNP-470. Compounds which target, decrease or inhibit the activity of a protein or lipid phosphatase are, e.g., inhibitors of phosphatase 1, phosphatase 2A, PTEN or CDC25, e.g., okadaic acid or a derivative thereof.

Compounds which induce cell differentiation processes are e.g. retinoic acid, α- γ- or δ-tocopherol or α- γ- or δ-tocotrienol.

The term cyclooxygenase inhibitor, as used herein, includes, but is not limited to, e.g., Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g., 5-methyl-2-(2'-chloro-6'-fluoroanilino)phenyl acetic acid or lumiracoxib.

The term "bisphosphonates", as used herein, includes, but is not limited to, etridonic, clodronic, tiludronic, pamidronic, alendronic, ibandronic, risedronic and zoledronic acid. "Etridonic acid" can be administered, e.g., in the form as it is marketed, e.g., under the trademark DIDRONEL, "Clodronic acid" can be administered, e.g., in the form as it is marketed, e.g., under the trademark BONEFOS. "Tiludronic acid" can be administered, e.g., in the form as it is marketed, e.g., under the trademark SKELID. "Pamidronic acid" can be administered, e.g., in the form as it is marketed, e.g., under the trademark AREDIA™. "Alendronic acid" can be administered, e.g., in the form as it is marketed, e.g., under the trademark FOSAMAX. "Ibandronic acid" can be administered, e.g., in the form as it is marketed, e.g., under the trademark BONDRANAT. "Risedronic acid" can be administered, e.g., in the form as it is marketed, e.g., under the trademark ACTONEL. "Zoledronic acid" can be administered, e.g., in the form as it is marketed, e.g., under the trademark ZOMETA.

The term "mTOR inhibitors" relates to compounds which inhibit the mammalian target of rapamycin (mTOR) and which possess antiproliferative activity, such as sirolimus (RAPAMUNE®), everolimus (CERTICAN™), CCI-779 and ABT578.

The term "heparanase inhibitor", as used herein, refers to compounds which target, decrease or inhibit heparin sulphate degradation. The term includes, but is not limited to, PI-88.

The term n "biological response modifier", as used herein, refers to a lymphokine or interferons, e.g., interferon γ.

The term "inhibitor of Ras oncogenic isoforms", e.g., H-Ras, K-Ras or N-Ras, as used herein, refers to compounds which target, decrease or inhibit the oncogenic activity of Ras, e.g., a "farnesyl transferase inhibitor", e.g., L-744832, DK8G557 or R115777 (Zarnestra).

The term "telomerase inhibitor", as used herein, refers to compounds which target, decrease or inhibit the activity of telomerase. Compounds which target, decrease or inhibit the activity of telomerase are especially compounds which inhibit the telomerase receptor, e.g., telomestatin.

The term "methionine aminopeptidase inhibitor", as used herein, refers to compounds which target, decrease or inhibit the activity of methionine aminopeptidase. Compounds which target, decrease or inhibit the activity of methionine aminopeptidase are, e.g., bengamide or a derivative thereof.

The term "proteasome inhibitor", as used herein, refers to compounds which target, decrease or inhibit the activity of the proteasome. Compounds which target, decrease or inhibit the activity of the proteasome include, e.g., PS-341 and MLN 341.

The term "matrix metalloproteinase inhibitor" or "MMP inhibitor", as used herein, includes, but is not limited to, collagen peptidomimetic and nonpeptidomimetic inhibitors, tetracycline derivatives, e.g., hydroxamate peptidomimetic inhibitor batimastat and its orally bioavailable analogue marimastat (BB-2516), prinomastat (AG 3340), metastat (NSC 683551) BMS-279251, BAY 12-9566, TAA211, MMI27013 or AAJ996.

The term "agents used in the treatment of hematologic malignancies", as used herein, includes, but is not limited to, EMS-like tyrosine kinase inhibitors, e.g., compounds targeting, decreasing or inhibiting the activity of FMS-like tyrosine kinase receptors (Flt-3R); interferon, 1-b-D-arabinofuransylcytosine (ara-c) and bisulfan; and ALK inhibitors, e.g., compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g., PKC412, midostaurin, a staurosporine derivative, SUI 1248 and MLN518.

The term "HSP90 inhibitors", as used herein, includes, but is not limited to, compounds targeting, decreasing or inhibiting the intrinsic ATPase activity of HSP90; degrading, targeting, decreasing or inhibiting the HSP90 client proteins via the ubiquitin proteasome pathway. Compounds targeting, decreasing or inhibiting the intrinsic ATPase activity of HSP90 are especially compounds, proteins or antibodies which inhibit the ATPase activity of HSP90, e.g., 17-allylamino, 17-demethoxygeldanamycin (17AAG), a geldanamycin derivative, other geldanamycin related compounds, radicicol and HDAC inhibitors.

The term "antiproliferative antibodies", as used herein, includes, but is not limited to, trastuzumab (Herceptin™), Trastuzumab-DM1, erlotinib (Tarceva™), bevacizumab (Avastin™), rituximab (Rituxan®), PR064553 (anti-CD40) and 2C4 antibody, By antibodies is meant, e.g., intact monoclonal antibodies, polyclonal antibodies, multispecific antibodies formed from at least two intact antibodies, and antibodies fragments so long as they exhibit the desired biological activity. For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

A compound of the formula (I) may also be used to advantage in combination with each other or in combination with other therapeutic agents, especially other anti-malarial agents. Such anti-malarial agents include, but are not limited to proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, inhaled NO, L-arginine, Dipropylenetri-amine NONOate (NO donor), Rosiglitzone (PPARy agonist), activated charcoal, Erythropoietin, Levamisole, and pyronaridine.

A compound of the formula (I) may also be used to advantage in combination with each other or in combination with other therapeutic agents, such as used for the treatment of Leishmaniosis, Trypanosomiasis, Toxoplasmosis and Neurocysticercosis, Such agents include, but are not limited to chloroquine sulfate, atovaquone-proguanil, artemether-lumefantrine, quinine-sulfate, artesunate, quinine, doxycycline, clindamycin, meglumine antimoniate, sodium stibogluconate, miltefosine, ketoconazole, pentamidine, amphotericin B (AmB), liposornal-AmB, paromomycine, eflornithine, nifurtimox, suramin, melarsoprol, prednisolone, benznidazole, sulfadiazine, pyrimethamine, clindamycin, trimetropim, sulfamethoxazole, azitromycin, atovaquone, dexamethasone, praziquantel, albendazole, beta-lactams, fluoroquinolones, macrolides, aminoglycosides, sulfadiazine and pyrimethamine.

The structure of the active agents identified by code nos., generic or trade names may be taken from the actual edition of the standard compendium "The Merck Index" or from databases, e.g., Patents International, e.g., IMS World Publications.

The above-mentioned compounds, which can be used in combination with a compound of the formula (I), can be prepared and administered as described in the art, such as in the documents cited above.

A compound of the formula (I) may also be used to advantage in combination with known therapeutic processes, e.g., the administration of hormones or especially radiation.

A compound of formula (I) may in particular be used as a radiosensitizer, especially for the treatment of tumors which exhibit poor sensitivity to radiotherapy.

By "combination", there is meant either a fixed combination in one dosage unit form, or a kit of parts for the combined administration where a compound of the formula (I) and a combination partner may be administered independently at the same time or separately within time intervals that especially allow that the combination partners show a cooperative, e.g., synergistic, effect or any combination thereof. The terms "coadministration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula I and a combination partner, are both administered to a patient simultaneously in the form of a single entity or dosage. The term "non-fixed combination" means that the active ingredients, e.g. a compound of formula (I) and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

Uses of the Compounds and Compositions Disclosed Herein

The compounds of the invention are inhibitors of kinase activity, in particular PI3-kinase activity. Compounds which are PI3-kinase inhibitors may be useful in the treatment of disorders wherein the underlying pathology is (at least in part) attributable to inappropriate PI3-kinase activity, such as asthma and chronic obstructive pulmonary disease (COPD). "Inappropriate PI3-kinase activity" refers to any PI3-kinase activity that deviates from the normal PI3-kinase activity expected in a particular patient. Inappropriate PI3-kinase may take the form of for instance, an abnormal increase in activity, or an aberration in the timing and or control of PI3-kinase activity. Such inappropriate activity may result then, for example, from overexpression or mutation of the protein kinase leading to inappropriate or uncontrolled activation. Accordingly, in another aspect the invention is directed to methods of treating such disorders.

Such disorders include, but not limited to, respiratory diseases including asthma, chronic obstructive pulmonary disease (COPD) and idiopathic pulmonary fibrosis (IPF); viral infections including viral respiratory tract infections and viral exacerbation of respiratory diseases such as asthma and COPD; non-viral respiratory infections including aspergillosis and leishmaniasis; allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia and Central pain.

In one embodiment, such disorders include respiratory diseases including asthma and chronic obstructive pulmonary disease (COPD); allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia and central pain.

The methods of treatment of the invention comprise administering a safe and effective amount of a compound of formula (I) or a pharmaceutically acceptable salt thereof to a patient in need thereof. Individual embodiments of the invention include methods of treating any one of the above-mentioned disorders by administering a safe and effective amount of a compound of formula (I) or a pharmaceutically acceptable salt thereof to a patient in need thereof.

The compounds of formula (I) or pharmaceutically acceptable salts thereof may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. Inhalation refers to administration into the patient's lungs whether inhaled through the mouth or through the nasal passages. In one embodiment, the compounds of formula (I) or pharmaceutically acceptable salts thereof may be administered orally. In another embodiment, the compounds of formula (I) or pharmaceutically acceptable salts thereof may be administered by inhalation. In a further embodiment, the compounds of formula (I) or pharmaceutically acceptable salts thereof may be administered intranasally.

The compounds of formula (I) or pharmaceutically acceptable salts thereof may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for a compound of formula (f) or a pharmaceutically acceptable salt thereof depend on the pharmacokinetic properties of that compound, such as absorption, distribution, and half-life, which can be determined by the skilled artisan. In addition, suitable dosing regimens, including the duration such regimens are administered, for a compound of formula (I) or a pharmaceutically acceptable salt thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

The compound of the present invention may be administered either simultaneously with, or before or after, one or more other therapeutic agent. The compound of the present invention may be administered separately, by the same or different route of administration, or together in the same pharmaceutical composition as the other agents.

The pharmaceutical composition or combination of the present invention can be in unit dosage of about 1-1000 mg of active ingredient(s) for a subject of about 50-70 kg, or about 1-500 mug or about 1-250 mug or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease. The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. A therapeutically effective amount in vivo may range depending on the route of administration, between about 0.01-500 mg/kg, or between about 1-100 mg/kg.

Additionally, the compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of the activity of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleavable in vivo. Such modifications, which include the preparation of phosphates, amides, esters, thioesters, carbonates, and carbamates, are well known to those skilled in the art.

In one aspect, the invention provides a method of treating a disorder mediated by inappropriate PI3-kinase activity comprising administering a safe and effective amount of a compound of formula (I) or a pharmaceutically acceptable salt thereof to a patient in need thereof.

In one embodiment, the conditions, diseases or disorders mediated by inappropriate PI3-kinase activity is selected from the group consisting of asthma, chronic obstructive pulmonary disease (COPD) and idiopathic pulmonary fibrosis (IPF); viral infections including viral respiratory tract infections and viral exacerbation of respiratory diseases such as asthma and COPD; non-viral respiratory infections including aspergillosis and leishmaniasis; allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia and Central pain.

Compounds of the invention may be useful in the treatment of conditions, diseases or disorders including disease or infection associated immunopathology in which one or more of the functions of B cells such as antibody production, antigen presentation, cytokine production or lymphoid organogenesis are abnormal or are undesirable including rheumatoid arthritis, pemphigus vulgaris and related diseases, idiopathic thrombocytopenia purpura, systemic lupus erythematosus, multiple sclerosis, myasthenia gravis, Sjogren's syndrome, autoimmune hemolytic anemia, ANCA-associated vasculitides, cryoglobulinemia, thrombotic thrombocytopenic purpura, chronic autoimmune urticaria, allergy (atopic dermatitis, contact dermatitis, allergic rhinitis), good pasture's syndrome, AMR (antibody-mediated transplant rejection), B cell-mediated hyperacute, acute and chronic transplant rejection and cancers of haematopoietic origin including but not limited to multiple myeloma; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Walden stroem disease.

The invention includes methods of treating conditions, diseases or disorders in which one or more of the functions of neutrophils, such as superoxide release, stimulated exocytosis, or chemoatractic migration are abnormal or are undesirable including rheumatoid arthritis, sepsis, pulmonary or respiratory disorders such as asthma, inflammatory dermatoses such as psoriasis as well as in disease or infection associated immunopathology and others.

The invention includes methods of treating conditions, diseases or disorders in which one or more of the functions of basophil and mast cells such as chemoatractic migration or allergen-IgE-mediated degranulation are abnormal or are undesirable including allergic diseases (atopic dermatitis, contact dermatitis, allergic rhinitis) as well as other disorders such as COPD, asthma or emphysema.

The invention includes methods of treating conditions, diseases or disorders in which one or more of the functions of T cells such as cytokine production or cell-mediated cytotoxicity abnormal or are undesirable including rheumatoid arthritis, multiple sclerosis, acute or chronic rejection of cell tissue or organ grafts or cancers of haematopoietic origin as well as in disease or infection associated immunopathology.

Further, the invention includes methods of treating neurodegenerative diseases, cardiovascular diseases and platelet aggregation.

Further, the invention includes methods of treating skin diseases such as porphyria cutanea tarda, polymorphous light eruption, dermatomyositis, solar urticaria, oral lichen planus, panniculitis, scleroderma, urticarial vasculitis.

Further, the invention includes methods of treating chronic inflammatory diseases such as sarcoidosis, granuloma annulare.

In other embodiments, the condition or disorder (e.g. PI3K-mediated) is selected from the group consisting of: polycythemia vera, essential thrombocythemia, myelofibrosis with myeloid metaplasia, asthma, COPD, ARDS, Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, psoriasis, contact dermatitis, atopic dermatitis, alopecia areata, erythema muitiforme, dermatitis herpetiformis, scleroderma, vitiligo, hypersensitivity angiitis, urticaria, bullous pemphigoid, lupus erythematosus, pemphigus, epidermolysis bullosa acquisita, autoimmune haematogical disorders (e.g. haemolytic anaemia, aplastic anaemia, pure red cell anaemia and idiopathic thrombocytopenia), systemic lupus erythematosus, polychondritis, scleroderma, Wegener granulomatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine ophthalmopathy, Grave's disease, sarcoidosis, alveolitis, chronic hypersensitivity pneumonitis, multiple sclerosis, primary biliary cirrhosis, uveitis (anterior and posterior), interstitial lung fibrosis, psoriatic arthritis, glomerulonephritis, cardiovascular diseases, atherosclerosis, hypertension, deep venous thrombosis, stroke, myocardial infarction, unstable angina, thromboembolism, pulmonary embolism, thrombolytic diseases, acute arterial ischemic, peripheral thrombotic occlusions, and coronary artery disease, reperfusion injuries, retinopathy, such as diabetic retinopathy or hyperbaric oxygen-induced retinopathy, and conditions characterized by elevated intraocular pressure or secretion of ocular aqueous humor, such as glaucoma.

In one embodiment, the disorder mediated by inappropriate PI3-kinase activity is pain.

In another embodiment, the compounds of the present invention are useful in the treatment of conditions or disorders selected from the group consisting of, primary cutaneous B-cell lymphoma, immunobullous disease, pemphigus vulgaris, pemphigus foliaceus, endemic form of Brazilian pemphigus (Fogo selvagem), paraneoplastic pemphigus, bullous pemphigoid, mucous membrane pemphigoid, epidermolysis bullosa acquisita, chronic graft versus host disease, dermatomyositis, systemic lupus erythematosus, vasculitis, small vessel vasculitis, hypocomplementemic urticarial vasculitis, antineutrophil cytoplasmic antibody-vasculitis, cryoglobulinemia, Schnitzler syndrome, Waldenstrom's macroglobulinemia, angioedema, vitiligo, systemic lupus erythematosus, idiopathic thrombocytopenic purpura, multiple sclerosis, cold agglutinin disease, autoimmune hemolytic anemia, antineutrophil cytoplasmic antibody—associated vasculitis, graft versus host disease, cryoglobulinemia and thrombotic thrombocytopenic.

In another embodiment, the compounds of the present invention are useful in the treatment, prevention, or amelioration of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, spondyloarhropathies including ankolsing spondylitis, Reiter syndrome, reactive arthritis, psoriatic arthritis, and enterophathics arthritis, hypersensitivity (including both airways hypersensitivity and dermal hypersensitivity) and allergies. Specific auto-immune diseases for which antibodies of the invention may be employed include autoimmune haematological disorders (including e.g. hemolytic anaemia, aplastic anaemia, pure red cell anaemia and idiopathic thrombocytopenia), acquired hemophilia A, cold agglutinin disease, cryoglobutinemia, thrombotic thrombocytopenic purpura, Sjogren's syndrome, systemic lupus erythematosus, inflammatory muscle disorders, polychondritis, scleredoma, anti-neutrophil cytoplasmic antibody-associated vasculitis, IgM mediated neuropathy, opsoclonus myoclonus syndrome, Wegener granulomatosis, dermatomyositis, chronic active hepatitis, myasthenia gravis, psoriasis, Steven-Johnson syndrome, pemphigus vulgaris, pemphigus foliacius, idiopathic sprue, autoimmune inflammatory bowel disease (including e.g. ulcerative colitis, Crohn's disease and Irritable Bowel Syndrome), endocrine ophthalmopathy, Graves' disease, sarcoidosis, multiple sclerosis, neuromyelitis optica, primary biliary cirrhosis, juvenile diabetes (diabetes mellitus type I), uveitis (anterior, intermediate and posterior as well as panuveitis), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy), tumors, inflammatory disease of skin and cornea, myositis, loosening of bone implants, metabolic disorders, such as atherosclerosis, diabetes, and dislipidemia.

In one embodiment, the present invention provides the use of a compound of formula (I) in therapy. In a further embodiment, the therapy is selected from a disease which may be treated by inhibition of PI3K. In another embodiment, the disease is selected from the afore-mentioned list, suitably from autoimmune disorders, inflammatory diseases, allergic diseases, airway diseases, such as asthma and COPD, transplant rejection; antibody production, antigen presentation, cytokine production or lymphoid organogenesis are abnormal or are undesirable including rheumatoid arthritis, pemphigus vulgaris, idiopathic thrombocytopenia purpura, systemic lupus erythematosus, multiple sclerosis, myasthenia gravis, Sjogren's syndrome, autoimmune hemolytic anemia, ANCA-associated vasculitides, cryoglobulinemia, thrombotic thrombocytopenic purpura, chronic autoimmune urticaria, allergy atopic dermatitis, contact dermatitis, allergic rhinitis), goodpasture's syndrome, AMR (antibody-mediated transplant rejection), B cell-mediated hyperacute, acute and chronic transplant rejection and cancers of haematopoietic origin including but not limited to multiple myeloma; a leukaemia; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Walden stroem disease; more suitably from rheumatoid arthritis (RA), pemphigus vulgaris (PV), idiopathic thrombocytopenia purpura (ITP), thrombotic thrombocytopenic purpura (TTP), autoimmune hemolytic anemia (AIHA), acquired hemophilia type A (AHA), systemic lupus erythematosus (SLE), multiple sclerosis (MS), myasthenia gravis (MG), Sjogren's syndrome (SS), ANCA-associated vasculitides, cryoglobulinemia, chronic autoimmune urticaria (CAU), allergy (atopic dermatitis, contact dermatitis, allergic rhinitis), goodpasture's syndrome, transplant rejection and cancers of haematopoietic origin as well as in disease or infection associated immunopathology, for example in severe and cerebral malaria, trypanosomiasis, leishmaniasis, toxoplasmosis and neurocysticercosis.

Thus, as a further embodiment, the present invention provides the use of a compound of formula (I) for the manufacture of a medicament. In a further embodiment, the medicament is for treatment of a disease which may be treated inhibition of PI3K. In another embodiment, the disease is selected from the afore-mentioned list, suitably from autoimmune disorders, inflammatory diseases, allergic diseases, airway diseases, such as asthma and COPD, transplant rejection; antibody production, antigen presentation, cytokine production or lymphoid organogenesis are abnormal or are undesirable including rheumatoid arthritis, pemphigus vulgaris, idiopathic thrombocytopenia purpura, systemic lupus erythematosus, multiple sclerosis, myasthenia gravis, Sjogren's syndrome, autoimmune hemolytic anemia, ANCA-associated vasculitides, cryoglobulinemia, thrombotic thrombocytopenic purpura, chronic autoimmune urticaria, allergy (atopic dermatitis, contact dermatitis, allergic rhinitis), goodpasture's syndrome, AMR (antibody-mediated transplant rejection), B cell-mediated hyperacute, acute and chronic transplant rejection and cancers of haematopoietic origin including but not limited to multiple myeloma; a leukaemia; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Walden stroem disease; more suitably from rheumatoid arthritis (RA), pemphigus vulgaris (PV), idiopathic thrombocytopenia purpura (ITP), thrombotic thrombocytopenic purpura (TTP), autoimmune hemolytic anemia (AMA), acquired hemophilia type A (AHA), systemic lupus erythematosus (SLE), multiple sclerosis (MS), myasthenia gravis (MG), Sjogren's syndrome (SS), ANCA-associated vasculitides, cryoglobulinemia, chronic autoimmune urticaria (CAU), allergy (atopic dermatitis, contact dermatitis, allergic rhinitis), goodpasture's syndrome, transplant rejection and cancers of haematopoietic origin as well as in disease or infection associated immunopathology, for example in severe and cerebral malaria, trypanosomiasis, leishmaniasis, toxoplasmosis and neurocysticercosis, General Synthetic Procedures In order to illustrate the invention, the following examples are included. However, it is to be understood that these examples do not limit the invention and are only meant to suggest a method of practicing the invention.

Generally, the compounds in this invention may be prepared by methods described herein, wherein the substituents are as defined for formula (I), above, except where further noted. The following non-limiting schemes and examples are presented to further exemplify the invention. Persons skilled in the art will recognize that the chemical reactions described herein may be readily adapted to prepare a number of other compounds of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Arco Chemical Company and Alfa Chemical Company, Shanghai Medpep. Co Ltd, Aladdin-Shanghai Jinchun Reagents, Ltd, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tainjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium Anhydrous $CH_2Cl_2$ and $CHCl_3$ were Obtained by refluxing the solvent with $CaH_2$. EtOAc, PE, hexanes, DMA and DM': were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1$H NMR spectra were recorded with a Bruker 400 MHz spectrometer or a Broker 600 MHz spectrometer at ambient temperature. NMR spectra were obtained as $CDCl_3$, DMSO-$d_6$, $CD_3OD$ or acetone-$d_6$ solutions (reported in ppm), using TMS (0 ppm) or chloroform (7.26 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants (J), when given, are reported in Hertz (Hz).

Low-resolution mass spectral (MS) data were generally determined on an Agilent 6120 Quadrupole HPLC-MS (Zorbax SB-C18, 2.1×30 mm, 3.5 micron, 6 minutes run, 0.6 mL/min flow rate, 5% to 95% (0.1% formic acid in $CH_3CN$) in (0.1% formic acid in $H_2O$)) with UV detection at 210 nm/254 nm and electrospray ionization mode (ESI).

Purities of compounds were assessed by Agilent 1260 Pre-HPLC or Calesep Pump 250 Pre-HPLC (Column NOVASEP 50/80 mm DAC) with UV detection at 210 nm/254 nm.

The following abbreviations are used throughout the specification.

aq. aqueous
ATP Adenosine Triphosphate
AcOH, HAc, $CH_3COOH$ acetic acid
AcOK, $CH_3COOK$ potassium acetate
AIBN azodiisobutyronitrile
$AlCl_3$ aluminum chloride
$BBr_3$ boron tribromide
BINAP 2,2'-bis(diphenylphosphino)-1,1'-binaphthyl
BPO benzoyl peroxide
$Bu_4NF$ tetrabutylammonium fluoride
Burgess Reagent (carboxysulfamoyl)triethylammonium hydroxide inner salt methyl ester
BSA bovine serum albumin
BOC, Boc butyloxycarbonyl
n-BuOH butyl alcohol
n-BuLi n-butyllithium
(n-Bu)$_3$SnCl tri-n-butyltin chloride
Ca(SO$_3$CF$_3$)$_2$ calcium trifluoromethyl sulfonate
Cs$_2$CO$_3$ cesium carbonate
CCl$_4$ carbon tetrachloride
CH$_2$Cl$_2$, DCM methylene chloride
CHCl$_3$ chloroform
CH$_2$I$_2$ diiodomethane
CH$_3$CHO acetaldehyde
CH$_3$MgBr methylmagnesium bromide
CDCl$_3$ chloroform deuterated
CH$_3$CN, MeCN acetonitrile
CH$_3$SO$_2$Cl, MsCl methanesulfonyl chloride
Cu copper
CuI cuprous iodide
DCC N,N'-dicyclohexylcarbodiimide
DBU 1,8-diazabicyclo[5.4.0]undec-7-ene
DBDMH 1,3-dibromo-5,5-dimethylhydantoin
D$_2$ deuterium gas
DIBAL diisobutylaluminum hydride
DIAD diisopropyl azodicarboxylate
DIEA, DIPEA, iPr$_2$Net N,N-Diisopropylethylamine
DEAD dimethyl azodicarboxylate
DMF dimethylformamide
DMAP 4-dimethylaminopyridine
DMSO dimethylsulfoxide
DMFDMA N,N-dimethylformamide dimethyl acetal DMP DessMartin periodinane
DPPA diphenylphosphoryl azide
DTT DL-Dithiothreitol
EDC, EDCI 1-(3-dimethylaminopropyl)-3-ethylcarbodiimide hydrochloride
EDTA ethylenediaminetetraacetic acid
$Et_3N$, TEA triethylamine
EtOAc, EA, ethyl acetate
$Et_2O$ diethyl ether
EtOH ethanol
EtMgBr ethylmagnesium Bromide
FBS fetal bovine serum
Fe iron
g gram
h hour
HATU 2-(7-aza-1H-benzotriazole-1-yl)-1,1,3,3-tetramethyluronium hexafluorophosphate
HBr hydrobromic acid
HCl hydrochloric acid
HOAc acetic acid
HOAT 1-hydroxy-7-azabenzotriazole
HOBt 1-hydroxybenzotriazole hydrate
$H_2$ hydrogen
$H_2O$ water
$H_2O_2$ hydrogen peroxide
$H_3PO_4$ orthophosphoric acid
$H_2SO_4$ sulphuric acid
$HNO_3$ nitric acid
HCOOK potassium formate
HMDS hexamethyldisilazane
HPLC high performance liquid chromatography or high pressure liquid chromatography
$I_2$ iodine
i-PrMgBr isopropylmagnesium Bromide
i-PrMgCl isopropylmagnesium Chloride
LiHMDS lithium bis(trimethylsilyl)-amide
LDA lithium diisopropylamide
MBP myelin basic protein
MCPBA meta-chloroperbenzoic acid
$MgSO_4$ magnesium sulfate
MeOH, $CH_3OH$ methanol
MeI, $CH_3I$ methyl iodide
MOPS 3-(N-morpholino)propanesulfonic acid
2-MeTHF 2-methyl tetrahydrofuran
mL, ml milliliter
min minute
$N_2$ nitrogen
NMP N-methylpyrrolidinone
$NaHCO_3$ sodium bicarbonate
$NaBH_4$ sodium borohydride
$NaBH_3CN$ sodium cyanoborohydride
NaOtBu sodium tert-butoxide
NaOMe, $CH_3ONa$ sodium methoxide
NaOH sodium hydroxide
$NaClO_2$ sodium chlorite
NaClO sodium hypochlorite
NaCl sodium chloride
$NaH_2PO_4$ sodium biphosphate
NaH sodium hydride
NaI sodium iodide
$Na_2SO_4$ sodium sulfate
NBS N-bromosuccinimide
NIS N-iodosuccinimide
NCS N-chlorosuccinimide
$NEt_3$ triethylamine
$NH_3$ ammonia
$NH_4Cl$ ammonium chloride
$NH_2OH$ hydroxylamine
PdC palladium on carbon
$Pd_2(dba)_3$ bis(dibenzylideneacetone) palladium
$Pd(OAc)_2$ palladium acetate
$Pd(OH)_2$ palladium hydroxide
$Pd(PPh_3)_4$ palladium tetrakis triphenylphosphine
$Pd(PPh_3)_2Cl_2$ bis(triphenylphosphine)palladium(II) chloride
$Pd(dppf)Cl_2$ 1,1-bis(diphenylphosphino)ferrocene palladium chloride
$Pd(dppf)Cl_2.CH_2Cl_2$ dichloro[1,1'bis(diphenylphosphino)ferrocene]palladium(II) dichloromethane adduct
$P(t-Bu)_3$ tri(tert-butyl)phosphine
PE petroleum ether (60-90° C.)
PBS phosphate buffered saline
$POCl_3$ phosphorous oxychloride
PPA polyphosphoricacid
$PhI(OAc)_2$ iodobenzene diacetate
$K_2CO_3$ potassium carbonate
KOH potassium hydroxide
RT rt r.t. room temperature
Rt retention time
$SOCl_2$ thionyl chloride
$SO_2Cl_2$ sulfuryl chloride
t-BuOK potassium tert-butanolate
TBTU O-benzotriazol-1-yl-N,N,N',N'-tetramethyluronium tetrafluoroborate
TBS tris buffered saline
THF tetrahydrofuran
TFA trifluoroacetic acid
TEAC bis(tetra-ethylammonium)carbonate
TLC thin layer chromatography
Tris trihydroxymethyl aminomethane
TsCl 4-toluene sulfonyl chloride
µL microliter
X-Phos 5-Bromo-4-chloro-3-indolylphosphat p-Toluidine salt
Zn zinc Representative synthetic procedures for the preparation of compounds of the disclosure are outlined below in following schemes. Unless otherwise indicated, each X, $R^2$, $R^3$ and $R^4$ carry the definitions set forth above in connection with formula (I).

Scheme 1

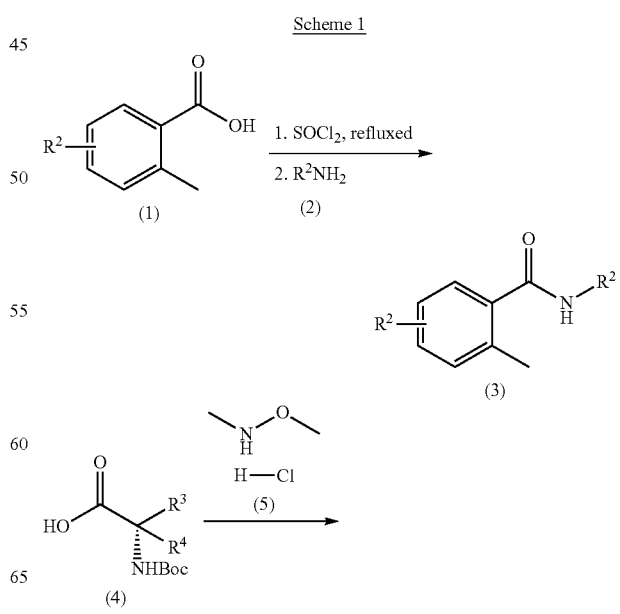

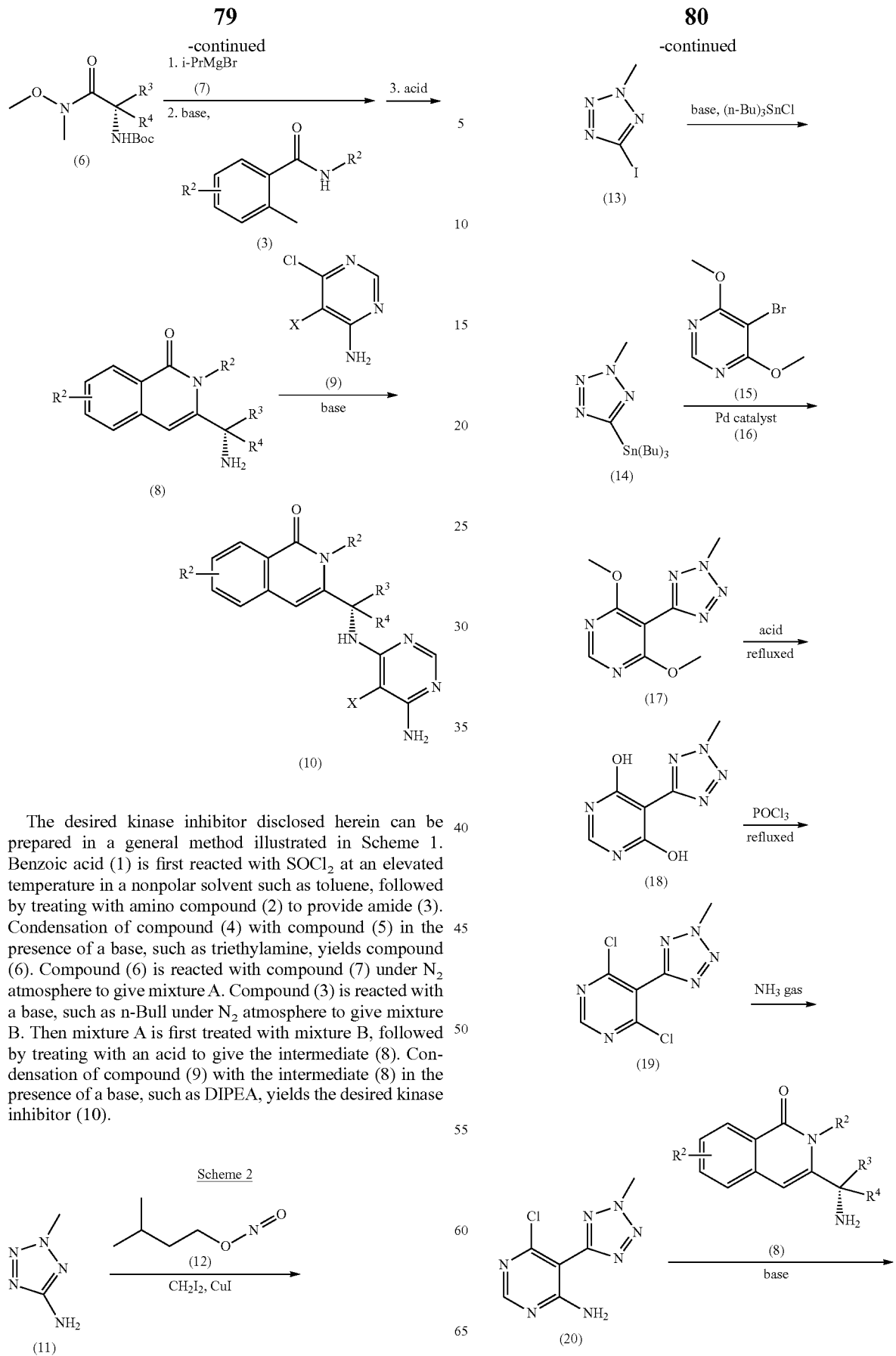

The desired kinase inhibitor disclosed herein can be prepared in a general method illustrated in Scheme 1. Benzoic acid (1) is first reacted with SOCl$_2$ at an elevated temperature in a nonpolar solvent such as toluene, followed by treating with amino compound (2) to provide amide (3). Condensation of compound (4) with compound (5) in the presence of a base, such as triethylamine, yields compound (6). Compound (6) is reacted with compound (7) under N$_2$ atmosphere to give mixture A. Compound (3) is reacted with a base, such as n-BuLi under N$_2$ atmosphere to give mixture B. Then mixture A is first treated with mixture B, followed by treating with an acid to give the intermediate (8). Condensation of compound (9) with the intermediate (8) in the presence of a base, such as DIPEA, yields the desired kinase inhibitor (10).

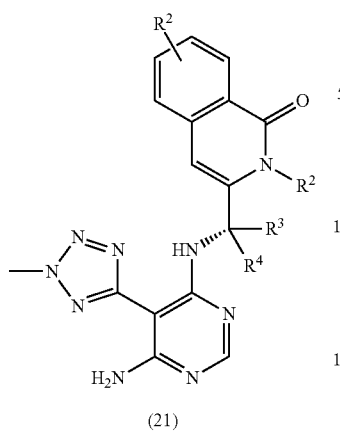

(21)

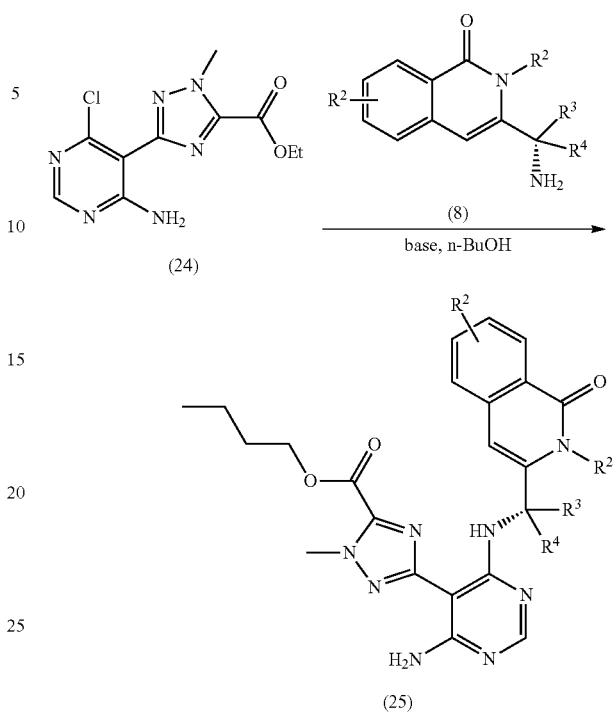

The desired kinase inhibitor disclosed herein can be prepared according to the general synthetic method illustrated in Scheme 2 and described in details in the Examples. The iodination of compound (11) in the presence of $CH_2I_2$, CuI and compound (12) at refluxed temperature affords compound (13), Iodo compound (13) is reacted with tributyltinchloride with the help of base such as n-butyllithium to give compound (14). Compound (14) is then coupled with compound (115) using an appropriate Pd complex as catalyst to provide compound (17). Compound (17) is then treated with concentrated hydrochloric acid to provide compound (18), which is converted to chloro compound (19) using a chlorinating agent such as $POCl_3$ or $SOCl_2$ under heating conditions. Subsequently, compound (19) is bubbled through $NH_3$ gas overnight to form compound (20) substituted with amine. Compound (20) is reacted with the intermediate (8) in the presence of a base such as DIPEA at refluxed temperature to afford the desired kinase inhibitor (21).

Scheme 3 shows another method to prepare the desired kinase inhibitor disclosed herein. Compound (22) is first converted to chloro compound (23) using a chlorinating agent such as $POCl_3$ or $SOCl_2$ under heating conditions. Subsequently, compound (23) is bubbled through $NH_3$ gas overnight to form compound (24) substituted with amine. Compound (24) is reacted with the intermediate (8) in the presence of a base such as DIPEA at refluxed temperature to afford the desired kinase inhibitor (25).

Scheme 3

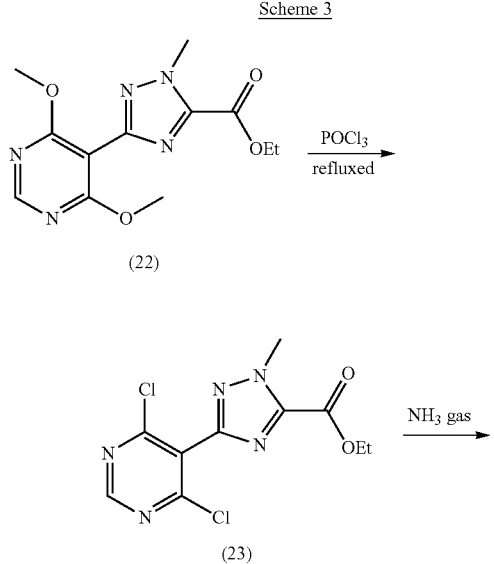

Scheme 4

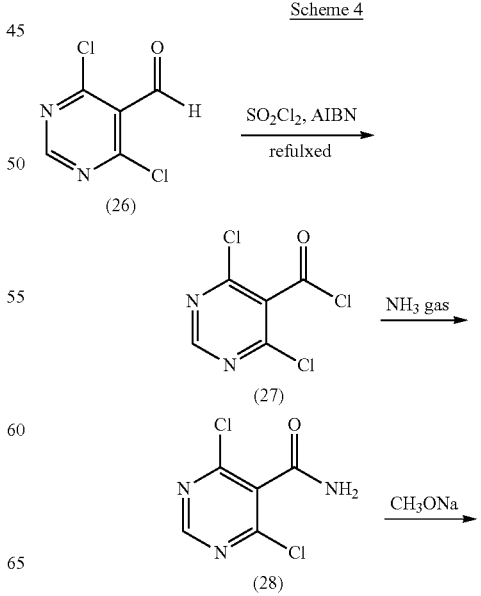

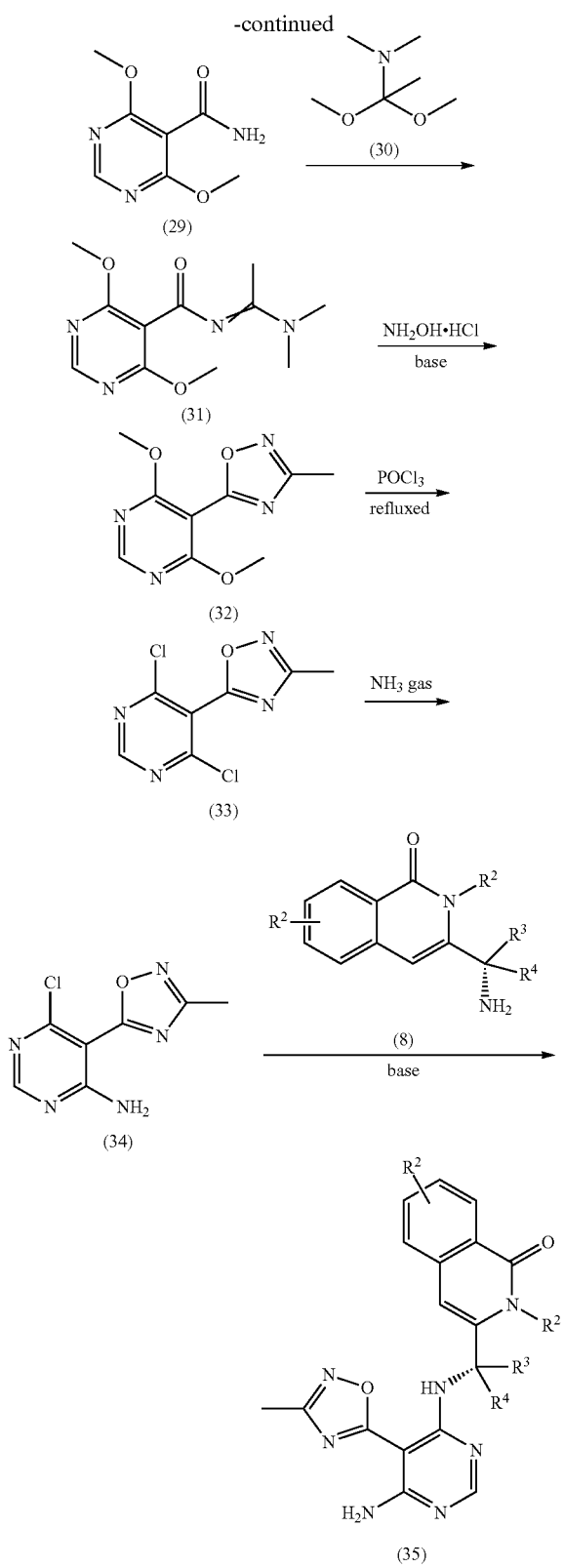

form amide (28). Compound (28) is treated with CH₃ONa to give compound (29). Subsequently, compound (29) is first treated with compound (30), followed by a cyclization reaction under the condition using hydroxylamine hydrochloride and a base to give compound (32). Compound (32) is first converted to chloro compound (33) using a chlorinating agent such as POCl₃ or SOCl₂ under heating conditions, then compound (33) is bubbled through NH₃ as overnight to form compound (34) substituted with amine. Compound (34) is reacted with the intermediate (8) in the presence of a base such as DIPEA at refluxed temperature to afford the desired kinase inhibitor (35).

EXAMPLES

Example 1 (S)-3-(1-((6-amino-5-(3-methyl-1,2,4-oxadiazol-5-yl)pyrimidin-4-yl)amino) propyl)-2-cyclopropyl-8-fluoroisoquinolin-1(2H)-one

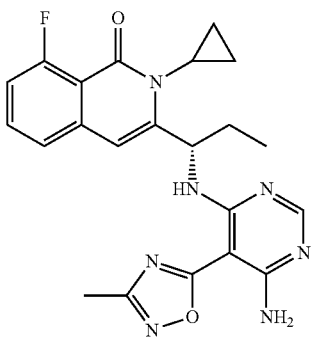

Step 1) N-cyclopropyl-2-fluoro-6-methylbenzamide

To a suspension of 2-fluoro-6-methylbenzoic acid (4.0 g, 25.95 mmol) in toluene (26 mL) was added SOCl₂ (7.5 mL, 103.80 mmol) at rt. The reaction was stirred at 90° C. overnight, then cooled down to rt and concentrated in vacuo. The residue was dissolved in a solution of NEt₃ (10.85 mL, 77.85 mmol) in THF (30 mL). Then cyclopropanamine (1.89 mL, 27.25 mmol) was added dropwise at 0° C. The resulted solution was warmed to rt and stirred further for 5 hours, then concentrated in vacuo. The residue was dissolved in H₂O (200 rut) and EtOAc (200 mL), and the separated organic phase was washed with saturated NaHCO₃ aqueous solution (200 mL) and saturated brine (200 mL), dried over anhydrous Na₂SO₄, and concentrated in vacuo to give the title compound as an off-white solid (4.25 g, 85%).

¹H NMR (400 MHz, CDCl₃) δ (ppm): 7.23-7.17 (ddd, J=8.0, 8.0, 6.0 Hz, 1H), 6.97-6.95 (d, J=7.6 Hz, 1H), 6.89-6.85 (dd, J=8.8, 8.8 Hz, 1H), 6.00 (br. s, 1H), 2.92-2.85 (m, 1H), 2.36 (s, 3H), 0.88-0.83 (m, 2H), 0.62-0.58 (m, 2H).

Step 2) (S)-tert-butyl-(1-(methoxy(methyl)amino)-1-oxobutan-2-1 carbamate

To a mixture of (S)-2-((tert-butoxycarbonyl)amino)butanoic acid (36.00 g, 177.13 mmol), N,O-dimethylhydroxylamine hydrochloride (20.73 g, 212.56 mmol), DMAP (21.64 g, 177.13 mmol) and triethylamine (96.89 mL, 690.82 mmol) in DCM (370 mL) was added EDCI (40.75 g, 212.56 mmol) portionwise at −5° C. The resulted mixture was stirred at rt overnight, then washed with H₂O (200

The desired kinase inhibitor with structure as defined in Formula (I) can also be prepared in a general method illustrated in Scheme 4. Compound (26) is converted to acyl chloride (27) in the presence of SO₂Cl₂ and AlBN. Compound (27) is then bubbled through NH₃ gas overnight to mL×2), saturated NaHCO₃ aqueous solution (200 mL) and brine (200 mL), The separated organic phase was concentrated in vacuo and the residue was purified by a silica gel column chromatography (PE/EtOAc (v/v)=4/1) to give the title compound as colorless oil (37.16 g, 85%).

¹H NMR (400 MHz, CDCl₃) δ (ppm): 5.17-5.16 (d, J=7.6 Hz, 1H), 4.62 (m, 1H), 3.76 (s, 3H), 3.20 (s, 3H), 1.79-1.70 (m, 1H), 1.61-1.50 (m, 1H), 1.43 (s, 9H), 0.95-0.91 (t, J=7.5 Hz, 3H).

Step 3) (S)-3-(1-aminopropyl)-2-cyclopropyl-8-fluoroisoquinolin-1(2H)-one

To a solution of N-cyclopropyl-2-fluoro-6-methylbenzamide (3.00 g, 15.53 mmol) in THF (22 mL) was added n-Bui (15.5 mL, 38.82 mmol) dropwise over 30 minutes at −30° C. under N₂ atmosphere. The resulted yellowish solution was stirred at this temperature for 30 minutes to give a system for the next step.

To a solution of (S)-tert-butyl(1-(methoxy(methyl)amino)-1-oxobutan-2-yl)carbamate (5.74 g, 23.29 mmol) in THF (110 mL) was added i-PrMgBr (25.6 mL, 25.6 mmol) dropwise over 30 minutes at −30° C. under N₂ atmosphere, and the mixture stirred at −30° C. for another 30 minutes, then the mixture of above system was added dropwise at this temperature. After the addition, the resulted mixture was stirred at −15° C. for 2 hours, then quenched with 5 mL of H₂O, acidified with concentrate HCl to pH=1 at 0° C., and the resulted mixture was concentrated in vacuo. The residue was dissolved in MeOH (45 mL) and concentrated HCl (22 mL). The resulted solution was stirred at 80° C. for 1 hour, cooled down to rt, and concentrated in vacuo. The residue was dissolved in DCM (40 mL) and MeOH (20 mL) which was added NaHCO₃ powder (100 mg, 1.20 mmol). The mixture was stirred at rt for 4 hours and filtered. The filtrate was concentrated in vacuo, then the residue was purified by a silica gel column chromatography (DCM/MeOH (v/v)=10/1) to give the title compound as a yellowish solid (3.08 g, 76%).

MS (ESI, pos. ion) mz: 261.0 [M+H]⁺;

¹H NMR (600 MHz, CDCl₃) δ (ppm): 7.53-7.50 (ddd, J=8.4, 8.4, 4.8 Hz, 1H), 7.35-7.34 (d, J=7.9 Hz, 1H), 7.18 (s, 1H), 7.07-7.04 (dd, J=11.2, 8.2 Hz, 1H), 5.22-5.20 (m, 1H), 3.08 (m, 1H), 2.39-3.32 (m, 1H), 2.21-2.15 (m, 1H), 2.08-2.02 (m, 1H), 1.34-1.29 (m, 1H), 1.22-1.17 (m, 1H), 1.04-1.01 (t, J=7.8 Hz, 3H), 0.66-0.62 (m, 1H).

Step 4) (S)-3-(1-((6-amino-5-(3-methyl-1,2,4-oxadiazol-5-yl)pyrimidin-4-yl)amino)propyl)-2-cyclopropyl-8-fluoroisoquinolin-1(2H)-one A mixture of (S)-3-(1-aminopropyl)-2-cyclopropyl-8-fluoroisoquinolin-1(2H)-one (35 mg, 0.13 mmol), 6-chloro-5-(3-methyl-1,2,4-oxadiazol-5-yl)pyrimidin-4-amine (28 mg, 0.13 mmol) and DIPEA (52 mg, 0.40 mmol) in n-BuOH (1 mL) was heated to 130° C., and stirred further for 24 hours, then cooled down to rt, and concentrated in vacuo. The residue was purified by a silica gel column chromatography (DCM/MeOH (v/v)=50/1) to give the title compound as an off-white solid (23 mg, 40%).

MS (ESI, pos. ion) mz: 436.0 [M+H]⁺;

¹H NMR (600 MHz, CDCl₃) δ (ppm): 8.60-8.59 (d, J=5.4 Hz, 1H), 8.11 (s, 1H), 7.45 (ddd, J=7.8, 7.8, 4.8 Hz, 1H), 7.10-7.09 (d, J=7.8 Hz, 1H), 7.01-6.98 (dd, J=10.8, 87.8 Hz, 1H), 6.33 (s, 1H), 6.01-5.98 (ddd, J=7.8, 7.8, 4.2 Hz, 1H), 3.01-2.97 (m, 1H), 2.51 (s, 3H), 2.07-2.02 (m, 1H), 1.86-1.79 (m, 1H), 1.50-1.47 (m, 1H), 1.42-1.37 (m, 1H), 1.31-1.27 (m, 1H), 1.12-1.10 (t, J=7.4 Hz, 3H), 0.94-0.89 (m, 1H).

Example 2 (S)-3-(1-((6-amino-5-(3-methyl-1,2,4-oxadiazol-5-yl)pyrimidin-4-yl)amino propyl)-8-methyl-2-phenylisoquinolin-1(2H)-one

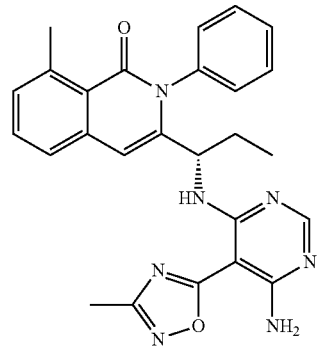 [SMILES: CC[C@H](Nc1ncnc(N)c1-c1nc(C)no1)c1cc2cccc(C)c2c(=O)n1-c1ccccc1]

Step 1) 2,6-dimethyl-N-phenylbenzamide

To a suspension of 2,6-dimethyl benzoic acid (5.0 g, 33.29 mmol) in toluene (100 was added SOCl₁₂ (12.08 mL, 166.47 mmol) at rt. The reaction was stirred at reflux overnight, then cooled to rt and concentrated in vacuo. The residue was dissolved in DCM (50 mL), and the solution was used for the next step directly.

To a mixture of triethylamine (6.73 g, 66.54 mmol) and aniline (3.10 g, 33.27 mmol) in DCM (50 mL) at 0° C. was added the above solution dropwise, followed by adding water (100 mL). The separated organic phase was washed with water (100 mL×2) and brine (50 mL), dried over anhydrous Na₂SO₄, and concentrated in vacuo. The residue was purified by a silica gel column chromatography (PE/EtOAc (v/v)=6/1) to give the title compound as a pale yellow solid (4.9 g, 65.4%).

MS (ESI, pos. ion) mz: 226.3 [M+H]⁺;

¹H NMR (600 MHz, DMSO-d₆) δ (ppm): 10.37 (s, 1H), 7.74 (d, J=7.6 Hz, 2H), 7.34 (t, J=7.9 Hz, 2H), 7.24 (t, J=7.6 Hz, 1H), 7.17-7.01 (m, 3H), 2.28 (s, 6H);

¹³C NMR (151 MHz, DMSO-d₆) δ (ppm): 168.36 (s), 139.56 (s), 138.94 (s), 134.13 (s), 129.20 (s), 128.86 (s), 127.73 (s), 124.06 (s), 120.03 (s), 19.33 (s).

Step 2) (S)-3-(1-aminopropyl)-8-methyl-2-phenylisoquinolin-1(2H)-one

To a solution of 2,6-dimethyl-N-phenylbenzamide (3.00 g, 13.32 mmol) ire THF (50 mL) was added n-BuLi in hexanes (2.4 M, 13.87 mL, 33.29 mmol) dropwise at −30°

C. under N₂ atmosphere over 30 minutes. The dark yellowish mixture was stirred at this temperature for 30 minutes, and the resulted solution was used for the next step.

To a solution of (S)-tert-butyl(1-(methoxy(methyl)amino)-1-oxobutan-2-yl)carbamate (4.92 g, 19.97 mmol) in THF (50 mL) was added i-PrMgCl in THF (2 M, 10.99 mL, 21.97 mmol) dropwise at −30° C. under N₂ atmosphere over 30 minutes. The resulted mixture was stirred at −30° C. for another 30 minutes. Then to this solution was added the above solution dropwise at −30° C. The resulted mixture was stirred at −15° C. for 3 hours, then quenched with H₂O (10 mL), acidified to pH=1-2 with concentrated HCl at 0° C. and concentrated in vacuo. The residue was dissolved in MeOH (50 mL) and then was added concentrated HCl (25 mL). The resulted mixture was stirred at reflux for 3 hours, cooled to rt and concentrated in vacuo to remove MeOH. The residue was diluted with H₂O (25 mL) and extracted with EtOAc (50 mL×2). The separated aqueous phase was neutralized to pH=7-8 with saturated NaHCO₃ aqueous solution, and the resulted mixture was extracted with EtOAc (100 mL×3). The combined organic phases were washed with brine (100 mL), dried over Na₂SO₄, and concentrated in vacuo. The residue was purified by a silica gel column chromatography (PE/EtOAc (v/v)=1/1) to give the title compound as a pale yellow solid (2.5 g, 64.2%).

MS (ESI, pos. ion) mz: 293.2 [M+H]⁺;

¹H NMR (600 MHz, DMSO-d₆) δ (ppm): 7.59-7.51 (m, 3H), 7.51-7.44 (m, 2H), 7.33 (d, J=7.6 Hz, 1H), 7.28 (d, J=6.8 Hz, 1H), 7.21 (d, J=7.2 Hz, 1H), 6.77 (s, 1H), 3.14 (dd, J=7.2, 5.1 Hz, 1H), 2.73 (s, 3H), 1.62-1.52 (m, 1H), 1.35-1.27 (m, 1H), 0.66 (t, J=7.3 Hz, 3H);

¹³C NMR (151 MHz, DMSO-d₆) δ (ppm): 163.51 (s), 149.74 (s), 141.12 (s), 139.20 (d, J=1.4 Hz), 132.41 (s), 130.26 (s), 129.70 (s), 129.45 (d, J=16.2 Hz), 128.59 (s), 124.91 (s), 123.02 (s), 102.42 (s), 53.19 (s), 30.51 (s), 23.90 (s), 11.24 (s).

Step 3) (S)-3-(1-((6-amino-5-(3-methyl-1,2,4-oxadiazol-5-yl)pyrimidin-4-yl)amino)propyl)-8-methyl-2-phenylisoquinolin-1(2H)-one To a suspension of 6-chloro-5-(3-methyl-1,2,4-oxadiazol-5-yl)pyrimidin-4-amine (31 mg, 0.147 mmol) and (S)-3-(1-aminopropyl)-8-methyl-2-phenylisoquinolin-1(2H)-one (52 mg, 0.178 mmol) in n-BuOH (2 mL) was added DIPEA (38 mg, 0.293 mmol). The reaction mixture was heated to reflux and stirred further for 22 hours. The reaction was monitored by TLC (PE/EtOAc, v/v, 1/3). After completion, the reaction mixture was cooled to rt and concentrated in vacuo. The residue was diluted with EtOAc (15 mL), and the resulted mixture was washed with water (15 mL) and brine (10 mL). The separated organic phase was dried over anhydrous Na₂SO₄, and concentrated in vacuo. The residue was purified by a silica gel column chromatography (PE/EtOAc (v/v)=2/1) to afford the title compound as an off-white solid (50 mg, 73.0%).

MS (ESI, pos. ion): 468.3 [M+H]⁺; HPLC: 99.2%;

¹H NMR (400 MHz, CDCl₃) δ (ppm): 8.43 (d, J=6.5 Hz, 1H), 8.06 (s, 1H), 7.59-7.51 (m, 3H), 7.50-7.44 (m, 2H), 7.34 (d, J=7.7 Hz, 1H), 7.30 (d, J=8.7 Hz, 1H), 7.21 (d, J=7.3 Hz, 1H), 6.47 (s, 1H), 4.86 (td, J=8.2, 4.5 Hz, 1H), 2.88 (s, 3H), 2.52 (s, 3H), 1.94-1.81 (m, 1H), 1.78-1.63 (m, 2H), 0.89 (t, J=7.4 Hz, 3H).

Example 3 (S)-3-(1-((6-amino-5-(3-methyl-1,2,4-oxadiazol-5-yl)pyrimidin-4-yl)amino propyl)-8-chloro-2-phenylisoquinolin-1(2H)-one

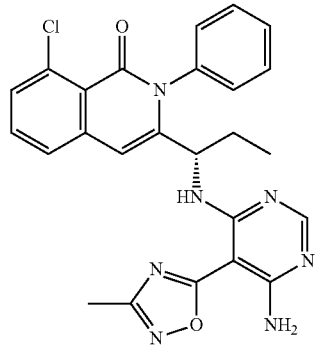 [SMILES: CC[C@H](Nc1ncnc(N)c1-c1nc(C)no1)c1cc2cccc(Cl)c2c(=O)n1-c1ccccc1]

Step 1) 2-chloro-6-methyl-N-phenylbenzamide

To a solution of 2-chloro-6-methylbenzoic acid (6.00 g, 35.17 mmol) in toluene (40 mL) was added SOCl₂ (10.21 mL, 140.69 mmol) at rt. The reaction was stirred at 110° C. for 5 hours, then cooled down to rt, and concentrated in vacuo. The residue was dissolved in DCM (50 mL), and to the resulted solution were added NEt₃ (14.71 mL, 105.51 mmol) and then aniline (2.95 g, 31.65 mmol) at 0° C. The resulted solution was stirred at rt overnight, washed with 200 mL of HA), 200 mL of saturated NaHCO₃ aq. and 200 mL of saturated brine, and then the organic phase was concentrated in vacuo. The residue was purified by a silica gel column chromatography (PE/EtOAc (v/v)=4/1) to give the title compound as a white solid (7.4 g, 86%).

MS (ESI, pos. ion) mz: 246.0 [M+H]⁺;

¹H NMR (400 MHz, CDCl₃) δ (ppm): 7.63-7.61 (d, J=8.0 Hz, 2H), 7.45 (br. s, 1H), 7.39-7.35 (t, J=8.0 Hz, 2H), 7.25-7.13 (m, 4H), 2.42 (s, 3H).

Step 2) (S)-3-(1-aminopropyl)-8-chloro-2-phenylisoquinolin-1(2H)-one

To a solution of 2-chloro-6-methyl-N-phenylbenzamide (1.50 g, 6.10 mmol THF (10 mL) was added n-BuLi in THF (2.5 M, 610 mL, 15.26 mmol) dropwise over 30 minutes at −30° C. under N₂ atmosphere, then the resulted dark yellowish solution was stirred at this temperature for 30 minutes, and used for the next step.

To a solution of tert-butyl(1-(methoxy(methyl)amino)-1-oxobutan-2-yl)carbamate (2.26 g, 9.16 mmol) in THF (15 mL) was added i-PrMgCl (2 M, 5.04 mL, 10.08 mmol) dropwise at −30° C. over 30 minutes under N₂ atmosphere. The reaction was stirred at −30° C. for another 30 minutes, and then was added to the above system dropwise at −30° C. The resulted solution was stirred at −15° C. for 2 hours, quenched with 50 mL of H₂O, and extracted with EtOAc (100 mL×2). The combined organic phases were washed with 100 mL of saturated NH₄Cl aqueous solution and 100 mL of saturated brine, and concentrated in vacuo to give yellowish oil which was not purified for the next step.

To the solution of the above yellow oil in 20 mL of MeOH was added 15 mL of concentrate HCl at rt. The resulted solution was stirred at 95° C. overnight, cooled to rt, and concentrated in vacuo to remove the organic solvent. The residue was extracted with PE/EtOAc (50 mL/25 mL). The aqueous layer was basified with NaHCO₃ powder to pH=8.5, and then extracted with DCM (80 mL×3). The combined organic phases were washed with 100 mL of saturated brine, and concentrated in vacuo, and the residue was purified by a silica gel column chromatography (DCM/MeOH (v/v)=20/1) to give the title compound as yellowish oil (1.2 g, 63%).

MS (ESI, pos. ion) mz: 313.0 [M+H]⁺;

¹H NMR (400 MHz, CDCl₃) δ (ppm): 7.53-7.39 (m, 6H), 7.25-7.23 (m, 2H), 6.62 (s, 1H), 3.42-3.38 (dd, J=7.2, 5.2 Hz, 0H), 1.74-1.64 (m, 1H), 1.51 (m, 1H), 0.80-0.76 (t, J=7.2 Hz, 1H).

Step 3) (S)-3-(1-((6-amino-5-(3-methyl-1,2,4-oxadiazol-5-yl)pyrimidin-4-yl)amino)propyl)-8-chloro-2-phenylisoquinolin-1(2H)-one A mixture of (S)-3-(1-aminopropyl)-8-chloro-2-phenylisoquinolin-1(2H)-one (44 mg, 0.14 mmol), 6-chloro-5-(3-methyl-1,2,4-oxadiazol-5-yl)pyrimidin-4-amine (30 mg, 0.14 mmol) and DIPEA (55 mg, 0.42 mmol) in n-BuOH (1 mL) was heated to 125° C. for 16 hours, cooled down to rt, and concentrated in vacuo. The residue was purified by a silica gel column chromatography (DCM/MeOH (v/v)=200/4) to give the title compound as a yellowish solid (43 mg, 62%).

MS (ESI, pos. ion) mz: 488.0 [M+1]⁺; HPLC: 98%;

¹H NMR (400 MHz, DMSO-d₆) δ (ppm): 8.53 (d, J=6.4 Hz, 1H), 8.02 (s, 1H), 7.58-7.42 (m, 8H), 6.65 (s, 1H), 4.56-4.51 (m, 1H), 2.44 (s, 3H), 1.86-1.79 (m, 1H), 1.69-1.61 (m, 1H), 0.78-0.74 (t, J=7.2 Hz, 3H).

Example 4 (S)-3-(1-((6-amino-5-(5-methyl-1,3,4-oxadiazol-2-yl)pyrimidin-4-yl)amino)ethyl)-8-chloro-2-cyclopropylisoquinolin-1(2H)-one

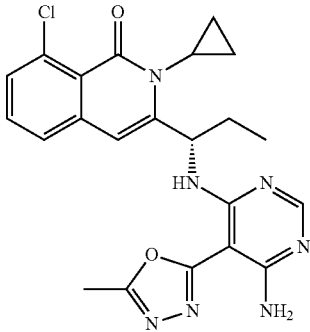 [SMILES: CC[C@H](Nc1ncnc(N)c1-c1nnc(C)o1)c1cc2cccc(Cl)c2c(=O)n1C1CC1]

Step 1) 2-chloro-N-cyclopropyl-6-methylbenzamide

To a suspension of 2-chloro-6-methylbenzoic acid (4.0 g, 23.45 mmol) in toluene (30 mL) was added SOCl₂ (8.0 mL, 106.54 mmol) at rt. The reaction was stirred at 90° C. overnight, then cooled down to rt, and concentrated in vacuo. The residue was dissolved in 30 mL of DCM, and then to the solution were added NEt₃ (13.00 mL, 93.79 mmol) and cyclopropanamine (1.80 mL, 25.79 mmol) dropwise at 0° C. The resulted solution was stirred at rt overnight, then quenched with 50 mL of saturated brine. The organic phase was washed with of 100 mL saturated NaHCO₃ aq, and 100 mL of saturated brine, dried over anhydrous Na₂SO₄, and concentrated in vacuo. The residue was purified by a silica gel column chromatography (PE/EtOAc (v/v)=1/1) to give the title compound as a white solid (4.5 g, 90%).

¹H NMR (600 MHz, CDCl₃) δ (ppm): 7.16-7.15 (m, 2H), 7.06-7.05 (m, 1H), 5.93 (br. s, 1H), 2.90-2.87 (m, 1H), 2.31 (s, 3H), 0.87-0.84 (m, 2H), 0.64-0.61 (m, 2H).

Step 2 (S)-2-((tert-butoxycarbonyl)amino)propanoic acid

To a suspension of (S)-2-aminopropanoic acid (10.00 g, 112.24 mmol) in H₂O (56 mL) was added NaOH (6.73 g, 168.36 mmol) at 0° C., followed by adding 56 mL of THF and (Boc)₂O (31.85 g, 145.91 mmol) via funnel. The resulted solution was stirred at rt for 17 hours, and extracted with petroleum ether (100 mL×2). The aqueous layer was acidified to pH=1 with 4 M HCl aqueous solution, then was extracted with EtOAc (100 mL×4). The combined organic phase was washed with 100 mL of saturated brine, dried over anhydrous Na₂SO₄, and concentrated in vacuo to give the title compound as colorless oil that was used for the next step without further purification (21.2 g, 100%).

¹H NMR (600 MHz, CDCl₃) δ (ppm): 9.95 (br. s, 1H), 5.19-5.18 (d, J=5.5 Hz, 1H), 4.32-4.31 (m, 1H), 1.41 (s, 9H), 1.41-1.39 (d, J=7.8 Hz, 3H).

Step 3) (S)-tert-butyl(1-(methoxy(methyl)amino)-1-oxopropan-2-yl)carbamate

To a mixture of (S)-2-((tert-butoxycarbonyl)amino)propanoic acid (22.00 g, 116.27 mmol), N,O-dimethylhydroxyamine hydrochloride (12.35 g, 127.90 mmol) and HOAT (18.99 g, 139.53 mmol) in DCM (232 mL) was added NEt₃ (64.8 mL, 465.09 mmol) at 0° C., and followed by addition of EDCI (26.75 g, 139.53 mmol) portionwise at −10° C., After addition, the resulted mixture was stirred at −10° C. for 1 hour, and then stirred at rt for 2 days, quenched with 200 mL of 1:120. The organic phase was washed with 200 mL of saturated NaHCO₃ aq. and 200 mL of saturated brine, dried over anhydrous Na₂SO₄, and concentrated in vacuo. The residue was purified by a silica gel column chromatography (PE/EtOAc (v/v)=4/1) to give the title compound as a white solid (7.4 g, 86%).

MS (ESI, pos. ion) mz: 177.0 [M-C₄H₈+H]⁺, 133.0 [M-Boc+H]⁺;

¹H NMR (600 MHz, CDCl₃) δ (ppm): 5.24 (d, J=5.4 Hz, 1H), 4.68 (m, 1H), 3.76 (s, 3H), 3.20 (s, 3H), 1.43 (s, 9H), 1.31-1.30 (d, J=6.6 Hz, 3H).

Step 4) (S)-3-(1-aminoethyl)-8-chloro-2-cyclopropylisoquinolin-1(2H)-one

To a solution of 2-chloro-N-cyclopropyl-6-methylbenzamide (1.50 g, 7.15 mmol) in THF (10 mL) was added n-BuLi (2.5 M, 7.15 mL, 17.87 mmol) dropwise at −30° C. under N₂ atmosphere over 30 minutes, and then the resulted dark yellowish solution was stirred at this temperature for 30 minutes, and used for the next step directly.

To a solution of (S)-tert-butyl(1-(methoxy(methyl)amino)-1-oxopropan-2-yl)carbamate (2.49 g, 10.73 mmol) in THF (15 mL) was added i-PrMgCl (2 M, 5.90 mL, 11.80 mmol) dropwise at −30° C. under N₂ atmosphere over 30 minutes. The reaction was stirred at −30° C. for another 30 minutes, and added to the above system dropwise at −30° C. The resulted solution was stirred at −15° C. for 3 hours, then quenched with 40 mL of H₂O, and added 60 mL of EtOAc and 60 mL of saturated NH₄Cl aqueous solution. The aqueous layer was extracted with EtOAc (100 mL×2), then the combined organic phases were washed with 100 mL of saturated NH₄Cl aq. and 100 mL of saturated brine, and concentrated in vacuo to give the title compound as yellowish oil which was used for next step without further purification.

To the solution of the above yellowish oil in 15 mL of MeOH was added 15 mL of concentrate HCl at rt. The resulted solution was stirred at 95° C. overnight, then cooled down to rt, and concentrated in vacuo. The residue was extracted with PE/EtOAc (50 mL/25 mL). The aqueous layer was basified to pH=8.5 with NaHCO₃ powder, then extracted with DCM (100 mL×3). The combined organic phases were washed with 100 mL of saturated brine, and concentrated in vacuo. The residue was purified by a silica gel column chromatography (DCM/MeOH (v/v)=20/1) to give the title compound as a yellowish solid (1.67 g, 89%).

MS (ESI, pos. ion) mz: 263.0 [M+H]⁺;
¹H NMR (600 MHz, DMSO-d₆) δ (ppm): 7.53-7.50 (t, J=7.8 Hz, 1H), 7.48-7.46 (dd, J=7.8, 1.0 Hz, 1H), 7.38-7.37 (dd, J=7.8, 1.2 Hz, 1H), 6.72 (s, 1H), 4.61-4.57 (q, J=6.6 Hz, 1H), 2.97 (m, 1H), 1.31-1.30 (d, J=6.6 Hz, 3H), 1.18-1.16 (m, 2H), 0.78-0.75 (m, 1H), 0.65-0.62 (m, 1H).

Step 5) (S)-3-(1-((6-amino-5-(5-methyl-1,3,4-oxadiazol-2-yl)pyrimidin-4-yl)amino)ethyl)-8-chloro-2-cyclopropylisoquinolin-1(2H)-one A mixture of (S)-3-(1-aminoethyl)-8-chloro-2-cyclopropyl isoquinolin-1(2H)-one (39 mg, 0.148 mmol), 6-chloro-5-(5-methyl-1,3,4-oxadiazol-2-yl)pyrimidin-4-amine (30 mg, 0.142 mmol) and DIPEA (55 mg, 0.42 mmol) in n-BuOH (1 mL) was heated to 130° C. and stirred further for 24 hours, then cooled to rt, and concentrated in vacuo. The residue was purified by a silica gel column chromatography (DCM/MeOH (v/v)=100/1) to give the title compound as a yellowish solid (35 mg, 56%).

MS (ESI, pos. ion) mz: 438.0 [M+H]⁺; HPLC: 98%;
¹H NMR (400 MHz, DMSO-d₆) δ (ppm): 8.41 (d, J=4.4 Hz, 1H), 8.02 (s, 1H), 7.48-7.40 (m, 3H), 7.28 (s, 2H), 6.54 (s, 1H), 5.95 (m, 1H), 3.02 (m, 1H), 2.60 (s, 3H), 1.59 (s, 3H), 1.22 (m, 4H).

Example 5 (S)-3-(1-((6-amino-5-(5-methyl-1,3,4-oxadiazol-2-yl)pyrimidin-4-yl)amino propyl)-8-chloro-2-phenylisoquinolin-1(2H)-one

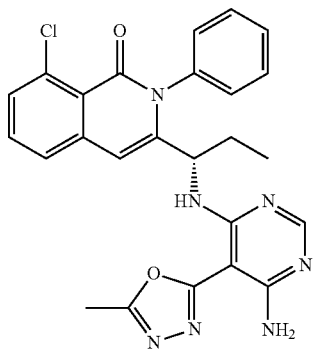 [SMILES: CC[C@H](Nc1ncnc(N)c1-c1nnc(C)o1)c1cc2cccc(Cl)c2c(=O)n1-c1ccccc1]

To a mixture of (S)-3-(1-aminopropyl)-8-chloro-2-phenylisoquinolin-1(24)-one (46 mg, 0.147 mmol), 6-chloro-5-(5-methyl-1,3,4-oxadiazol-2-yl)pyrimidin-4-amine (30 mg, MS (ESI, pos. ion) mz: 263.0 [M+H]⁺;

0.142 mmol) and IN PEA (55 mg, 0.42 mmol) in n-BuOH (1.5 mL) was heated to 125° C. for 16 hours, then cooled down to rt and concentrated in vacuo. The residue was purified by a silica gel column chromatography (DCM/MeOH (v/v)=50/1) to give a crude product which was further purified by preparative TLC to give the title compound as a light yellowish solid (39 mg, 56%).

MS (ESI, pos. ion) mz: 488.0 [M+H]⁺; HPLC: 97%;
¹H NMR (400 MHz, DMSO-d₆) δ (ppm): 8.35 (s, 1H), 8.00 (s, 1H), 7.55-7.24 (m, 8H), 6.62 (s, 1H), 4.52 (m, 1H), 2.60 (s, 3H), 1.82 (m, 1H), 1.63 (m, 1H), 0.74 (m, 3H).

Example 6 (S)-3-(1-((6-amino-5-(5-methyl-1,3,4-oxadiazol-2-yl)pyrimidin-4-yl)amino) propyl)-2-cyclopyropyl-8-methylisoquinolin-1(2H)-one

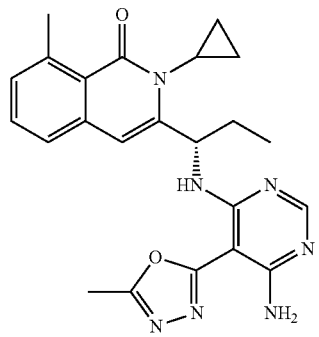 [SMILES: CC[C@H](Nc1ncnc(N)c1-c1nnc(C)o1)c1cc2cccc(C)c2c(=O)n1C1CC1]

Step 1) N-cyclopropyl-2,6-dimethylbenzamide

To a suspension of 2,6-dimethylbenzoic acid (4.0 g, 26.64 mmol) in toluene (30 mL) was added SOCl₂ (8.0 mL, 106.54 mmol) at rt. The reaction was stirred at 90° C. overnight, then cooled down to rt, and concentrated in vacuo. The residue was dissolved in 30 mL of DCM, then to the solution were added NEt₃ (14.85 mL, 106.54 mmol) and cyclopropanamine (2.03 mL, 29.30 mmol) dropwise at 0° C. The resulted solution was stirred at rt for 2 hours, and quenched with 50 mL of saturated brine. The separated organic phase was washed with 100 mL of saturated NaHCO₃ aqueous solution, and 100 mL of saturated brine, dried over anhydrous Na₂SO₄ and concentrated in vacuo. The residue was purified by a silica gel column chromatography (PE/EtOAc (v/v) 4/1) to give the title compound as an off-white solid (4.0 g, 80%).

¹H NMR (400 MHz, CDCl₃) δ (ppm): 7.14-7.10 (dd, J=7.6, 7.6 Hz, 1H), 6.99-6.97 (d, J=7.6 Hz, 2H), 5.81 (br. s, 1H), 3.92-2.86 (m, 1H), 2.28 (s, 6H), 0.88-0.84 (m, 2H), 0.60-0.56 (m, 2H).

Step 2) (S)-3-(1-aminopropyl)-2-cyclopropyl-8-methylisoquinolin-1(2H)-one

To a solution of N-cyclopropyl-2,6-dimethylbenzamide (2000 g, 10.57 mmol) in THF (20 mL) was added n-BuLi (10.57 mL, 26.42 mmol) dropwise over 30 minutes at −30° C. under N₂ atmosphere, and then the resulted dark yellowish solution was stirred at this temperature for 30 minutes, and used for the next step directly.

To a solution of (S)-tert-butyl(1-(methoxy(methyl)amino)-1-oxobutan-2-yl)carbamate (3.90 g, 15.85 mmol) in THF (20 mL) was added i-PrMgBr (1M, 17.44 mL, 17.44 mmol) dropwise at −30° C. under N₂ atmosphere over 30 minutes. The mixture was stirred at −30° C. for another 30 minutes, and then added to the above system dropwise at −30° C. The resulted solution was stirred at −15° C. for 3 hours, quenched with 50 mL H₂O, extracted with EtOAc (100 mL×2), and the combined organic phases were washed with 100 mL of saturated NH₄Cl aqueous solution and 100 mL of saturated brine, and concentrated in vacuo to give yellowish oil which was used for the next step without further purification.

To a solution of the above yellowish oil in 20 mL of MeOH was added 20 mL of concentrated HCl at rt. The reaction was stirred at 80° C. for 1 hour, then cooled to rt, and concentrated in vacuo. The residue was extracted with PE/EtOAc (50 mL/25 mL). The aqueous layer was basified to pH=8.5 with NaHCO₃ powder, and then extracted with DCM (100 mL×3). The combined organic phases were washed with 100 mL of saturated brine, and concentrated in vacuo. The residue was purified by a silica gel column chromatography (DCM/MeOH (v/v)=10/1) to give the title compound as yellowish oil (1.7 g, 62%).

MS (ESI, pos. ion) mz: 257.0 [M+H]⁺;
¹H NMR (600 MHz, CDCl₃) δ (ppm): 7.40-7.37 (dd, J=7.8, 7.2 Hz, 1H), 7.25-7.23 (d, J=7.8 Hz, 1H), 7.14-7.13 (d, J=7.2 Hz, 1H), 6.48 (s, 1H), 4.55-4.53 (dd, J=7.2, 5.4 Hz, 1H), 2.91-2.87 (m, 1H), 2.87 (s, 3H), 1.85-1.78 (m, 1H), 1.33-1.22 (m, 3H), 0.99 (t, J=7.4 Hz, 3H), 0.85-0.76 (m, 2H).

Step 3 (S)-3-(1-((6-amino-5-(5-methyl-1,3,4-oxadiazol-2-yl)pyrimidin-4-yl)amino)propyl)-2-cyclopropyl-8-methylisoquinolin-1(2H)-one To a mixture of (S)-3-(1-aminopropyl)-2-cyclopropyl-8-methylisoquinolin-1(2H)-one (38 mg, 0.148 mmol), 6-chloro-5-(5-methyl-1,3,4-oxadiazol-2-yl)pyrimidin-4-amine (30 mg, 0.142 mmol) and DIPEA (55 mg, 0.42 mmol) in n-BuOH (1.5 mL) was heated to 130° C. and stirred further for 116 hours, then cooled down to rt, and concentrated in vacuo. The residue was purified by a silica gel column chromatography (DCM/MeOH (v/v)=50/1) to give crude product which was further purified by a preparative TLC to give the title compound as a light yellowish solid (39 mg, 63.6%).

MS (ESI, pos. ion) mz: 432.0 [M+H]⁺; HPLC: 94%;
¹H NMR (400 MHz, DMSO-d₆) δ (ppm): 8.47 (s, 1H), 8.01 (s, 1H), 7.39-7.14 (m, 3H), 6.38 (s, 1H), 5.84 (m, 1H), 2.98 (m, 1H), 2.74 (s, 3H), 2.60 (s, 3H), 2.02 (m, 1H), 1.78 (m, 1H), 1.22 (m, 4H), 1.04 (m, 3H).

Example 7 (S)-3-(1-((6-amino-5-(3-methyl-1,2,4-oxadiazol-5-yl)pyrimidin-4-yl)amino) propyl)-8-chloro-2-cyclopropylisoquinolin-1(2H)-one

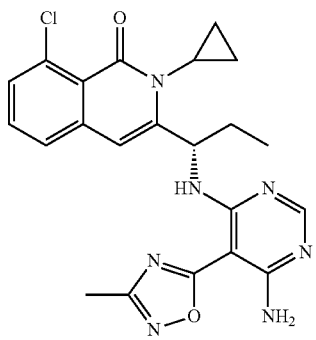 [SMILES: CC[C@H](Nc1ncnc(N)c1-c1nc(C)no1)c1cc2cccc(Cl)c2c(=O)n1C1CC1]

Step 1) 2-chloro-N-cyclopropyl-6-methylbenzamide

To a suspension of 2-chloro-6-methylbenzoic acid (4.0 g, 2145 mmol) in toluene (30 mL) was added SOCl₂ (8.0 mL, 106.54 mmol) at rt. The reaction was stirred at 90° C. overnight, then cooled down to rt, and concentrated in vacuo. The residue was dissolved in 30 mL of DCM, then to the solution were added NEt₃ (13.00 mL, 93.79 mmol) and cyclopropanamine (1.80 mL, 25.79 mmol) dropwise at 0° C. The resulted solution was stirred at rt overnight, then quenched with 50 mL of saturated brine. The separated organic phase was washed with 100 mL of saturated NaHCO₃ aq. and 100 mL of saturated brine, dried over anhydrous Na₂SO₄, and concentrated in vacuo. The residue was purified by a silica gel column chromatography (PE/EtOAc (v/v)=1/1) to give the title compound as a white solid (4.5 g, 90%).

¹H NMR (600 MHz, CDCl₃) δ (ppm): 7.16-7.15 (m, 2H), 7.06-7.05 (m, 1H), 5.93 (br. s, 1H), 2.90-2.87 (m, 1H), 2.31 (s, 3H), 0.87-0.84 (m, 2H), 0.64-0.61 (m, 2H).

Step 2) (S)-3-(1-aminopropyl)-8-chloro-2-cyclopropylisoquinolin-1(2H)-one

To a solution of 2-chloro-N-cyclopropyl-6-methylbenzamide (2.00 g, 9.54 mmol) in THF (20 mL) was added n-BuLi (10.50 mL, 25.75 mmol) dropwise over 30 minutes at −30° C. under N₂, atmosphere, and then the resulted dark yellowish solution was stirred at this temperature for 30 minutes, and used for the next step directly.

To a solution of (S)-tert-butyl(1-(methoxy(methyl)amino)-1-oxobutan-2-yl) carbamate (3.99 g, 16.22 mmol) in THF (20 mL) was added i-PrMgBr (2M, 9.54 mL, 19.08 mmol) dropwise at −30° C. under N₂ atmosphere over 30 minutes. The reaction was stirred at −30° C. for another 30 minutes, and then added to the above system drop wise at −30° C. The resulted solution was stirred at −15° C. for 3 hours, quenched with 50 mL H₂O, extracted with EtOAc (100 mL×2). The combined organic phases were washed with 100 mL of saturated NH₄Cl aq. and 100 mL of saturated brine, concentrated in vacuo to give yellowish oil which was used for the next step without further purification.

To a solution of the above yellowish oil in 20 mL of MeOH was added 20 mL of concentrated HCl at rt. The resulted solution was stirred at 80° C. for 1 hour, then cooled down to rt, and concentrated in vacuo. The residue was extracted with PE/EtOAc (50 mL/25 mL). The aqueous layer was basified to pH=8.5 with NaHCO₃ powder, and then extracted with DCM (100 mL×3). The combined organic phases were washed with 100 mL of saturated brine, and concentrated in vacuo. The residue was purified by a silica gel column chromatography (DCM/MeOH (v/v)=20/1) to give the title compound as yellowish oil (2.5 g, 95%).

MS (ESI, pos. ion) mz: 277.0 [M+H]⁺;
¹H NMR (400 MHz, CDCl₃) δ (ppm): 7.38-7.35 (m, 2H), 7.29-7.27 (dd, J=6.8, 2.4 Hz, 1H), 6.50 (s, 1H), 4.56-4.53 (dd, J=7.2, 5.2 Hz, 1H), 2.92-2.86 (m, 1H), 1.86-1.75 (m, 1H), 1.34-1.29 (m, 1H), 1.28-1.23 (m, 2H), 1.02-0.96 (t, J=7.6 Hz, 3H), 0.86-0.80 (m, 2H).

Step 3) (S)-3-(1-((6-amino-5-(3-methyl-1,2,4-oxadiazol-5-yl)pyrimidin-4-yl)amino)propyl)-8-chloro-2-cyclopropylisoquinolin-1(2H)-one A mixture of (S)-3-(1-aminopropyl)-8-chloro-2-cyclopropyl isoquinolin-1(2l)-one (47 mg, 0.17 mmol), 6-chloro-5-(3-methyl-1,2,4-oxadiazol-5-yl)pyrimidin-4-amine (30 mg, 0.14 mmol) and DIPEA (55 mg, 0.42 mmol) in n-BuOH (1 mL) was heated to 130° C. and stirred further for 24 hours, then cooled down to rt, and concentrated in vacuo. The residue was purified by a silica gel column chromatography (DCM/MeOH (v/v) 100/1) to give the title compound as a yellowish solid (46 mg, 72%).

MS (ESI, pos. ion) mz: 452.0 [M+H]$^+$; HPLC: 96%;

$^1$H NMR (600 MHz, CDCl$_3$) δ (ppm): 8.59-8.58 (d, J=5.4 Hz, 1H), 8.11 (s, 1H), 7.38-7.34 (m, 2H), 7.22-7.21 (dd, J=6.6, 2.4 Hz, 1H), 6.30 (s, 1H), 6.00-5.97 (td, J=7.8, 4.8 Hz, 1H), 3.02-2.98 (m, 1H), 2.50 (s, 3H), 2.08-2.01 (m, 1H), 1.86-1.79 (m, 1H), 1.51-1.47 (m, 1H), 1.42-1.37 (m, 1H), 1.33-1.28 (m, 1H), 1.12-1.09 (t, J=7.8 Hz, 3H), 0.90-0.86 (m, 1H).

Example 8 (S)-3-(1-(((6-amino-5-(3-methyl-1,2,4-oxadiazol-5-yl)pyrimidin-4-yl)amino)ethyl)-8-chloro-2-phenylisoquinolin-1(2H)-one

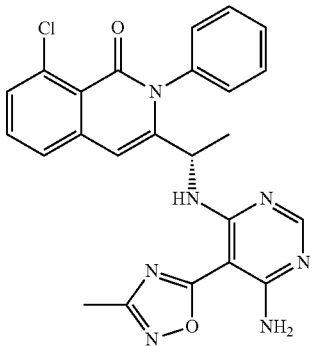 [SMILES: Cc1noc(-c2c(N)ncnc2N[C@@H](C)c2cc3cccc(Cl)c3c(=O)n2-c2ccccc2)n1]

Step 1) 2-chloro-6-methyl-N-phenylbenzamide

To a solution of 2-chloro-6-methylbenzoic acid (6.00 g, 35.17 mmol) ire Toluene (40 mL) was added SOCl$_2$ (10.21 mL, 140.69 mmol) at rt. The reaction was stirred at 110° C. for 5 hours, then cooled to rt, and concentrated in vacuo. The residue was dissolved in DCM (50 mL), then to the solution were added NEt$_3$ (14.71 mL, 105.51 mmol) and then aniline (2.95 g, 31.65 mmol) at 0° C. The resulted mixture was stirred at rt overnight, and washed with 200 mL of H$_2$O, 200 mL of saturated. NaHCO$_3$ aqueous solution and 200 mL of saturated brine. The separated organic phase was concentrated in vacuo. The residue was purified by a silica get column chromatography (PE/EtOAc (v/v) 4/1) to give the title compound as a white solid (7.4 g, 86%).

MS (ESI, pos. ion) mz: 246.0 [M+H]$^+$;

$^1$H NMR (400 MHz, CDCl$_3$) δ (ppm): 7.63-7.61 (d, J=8.0 Hz, 2H), 7.45 (br. s, 1H), 7.39-7.35 (t, J=8.0 Hz, 2H), 7.25-7.13 (m, 4H), 2.42 (s, 3H).

Step 2) (S)-3-(1-aminoethyl)-8-chloro-2-phenylisoquinolin-1(2H)-one

To a solution of 2-chloro-6-methyl-N-phenylbenzamide (2.00 g, 8.14 mmol) in THF (15 mL) was added n-BuLi (8.14 mL, 20.35 mmol) dropwise over 30 minutes at −30° C. under N$_2$ atmosphere, and then the resulted dark yellowish solution was stirred at this temperature for 30 minutes, and used for the next step.

To a solution of (S)-tert-butyl(1-(methoxy(methyl) amino)-1-oxopropan-2-yl)carbamate (2.84 g, 12.21 mmol) in THF (20 mL) was added i-PrMgCl (2 M, 6.72 mL, 13.43 mmol) dropwise over 30 minutes at −30° C. under N$_2$ atmosphere. The reaction was stirred at −30° C. for another 30 minutes, and added to the above system dropwise at −30° C. The resulted solution was stirred at −15° C. for 3 hours, quenched with 40 mL of H$_2$O, and added 100 mL of EtOAc and 100 mL of saturated NH$_4$Cl aqueous solution. The aqueous solution was extracted with EtOAc (100 mL×2). The combined organic phases were washed with 100 mL of saturated NH$_4$Cl aq and 100 mL of saturated brine, concentrated in vacuo to give yellowish oil which was used for next step without for further purification.

To the solution of the above yellowish oil in 15 mL of MeOH was added 15 mL of concentrate HCl at rt. The resulted solution was stirred at 95° C. for 14 hours, cooled to rt, concentrated in vacuo to remove the organic solvent. The residue was extracted with PE/EtOAc (50 mL/25 mL). The aqueous layer was basified with NaHCO$_3$ powder to pH=8.5, and then extracted with DCM (100 mL×3). The combined organic phases were washed with 100 mL of saturated brine, concentrated in vacuo, and the residue was purified by a silica gel column chromatography (DCM/MeOH (v/v)=10/1) to give the title compound as a yellowish solid (2.0 g, 78.6%).

MS (ESI, pos. ion) mz: 299.0 [M+H]$^+$;

$^1$H NMR (600 MHz, CDCl$_3$) δ (ppm): 7.54-7.41 (m, 6H), 7.27-7.26 (m, 2H), 6.71 (s, 1H), 3.72-3.69 (q, J=6.6 Hz, 1H), 1.25-1.24 (d, J=6.6 Hz, 3H).

Step 3) (S)-3-(1-((6-amino-5-(3-methyl-1,2,4-oxadiazol-5-yl)pyrimidin-4-yl)amino)ethyl)-8-chloro-2-phenylisoquinolin-1(2H)-one A mixture of (S)-3-(1-aminoethyl)-8-chloro-2-phenylisoquioilin-1(2H)-one (42 mg, 0.13 mmol), 6-chloro-5-(3-methyl-1,2,4-oxadiazol-5-yl)pyrimidin-4-amine (25 mg, 0.12 mmol) and DIPEA (46 mg, 0.35 mmol) in n-BuOH (1 mL) was heated to 125° C. for 7 hours, cooled down to rt, and concentrated in vacuo. The residue was purified by a silica gel column chromatography (DCM/MeOH (v/v)=50/1) to give the title compound as an off-white solid (17 mg, 30%).

MS (ESI, pos. ion) mz: 474.0 [M+H]$^+$; HPLC: 98%;

$^1$H NMR (600 MHz, CDCl$_3$) δ (ppm): 8.29-8.28 (d, J=5.4 Hz, 1H), 8.03 (s, 1H), 7.54-7.43 (m, 6H), 7.38-7.36 (dd, J=7.2, 1.2 Hz, 1H), 7.34-7.33 (d, J=7.2 Hz, 1H), 6.53 (s, 1H), 5.00-4.98 (m, 1H), 2.50 (s, 3H), 1.47 (d, J=6.8 Hz, 3H).

Example 9 (S)-3-(1-((6-amino-5-(5-methyl-1,3,4-oxadiazol-2-yl)pyrimidin-4-yl)amino)ethyl)-8-chloro-2-phenylisoquinolin-1(2H)-one

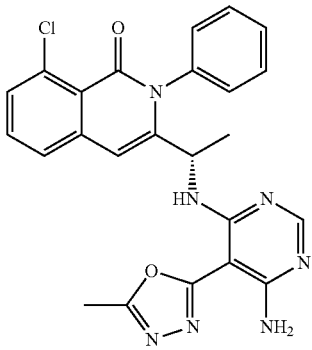 [SMILES: Cc1nnc(-c2c(N)ncnc2N[C@@H](C)c2cc3cccc(Cl)c3c(=O)n2-c2ccccc2)o1]

To a suspension of (S)-3-(1-aminoethyl)-8-chloro-2-phenylisoquinolin-1(2H)-one (50 mg, 0.16 mmol) and 6-chloro-5-(5-methyl-1,3,4-oxadiazol-2-yl)pyrimidin-4-amine (45 mg, 0.21 mmol) in n-BuOH (5 mL) was added DIPEA (45 mg, 0.35 mmol). The resulted mixture was heated at reflux for 16 hours, and monitored by TLC (PE/EtOAc, v/v, 1/2). Then the mixture was cooled to room temperature and concentrated in vacuo. The residue was purified by a silica gel column chromatography (PE/EtOAc (v/v)=1/2) to give the title compound as a white solid (65 mg, 86%).

MS (ESI, pos, ion): 474.1 [M+H]$^+$; HPLC: 99.3%;

$^1$H NMR (600 MHz, CDCl$_3$) δ (ppm): 8.88 (d, J=6.6 Hz, 1H), 8.02 (s, 1H), 7.60-7.11 (m, 7H), 6.56 (s, 1H), 6.45 (s, 2H), 5.03 (dd, J=13.4, 6.7 Hz, 1H), 4.14 (q, J 7.1 Hz, 1H), 2.69 (s, 3H), 1.49 (d, J=6.8 Hz, 3H).

Example 10 (S)-3-(1-((6-amino-5-(5-methyl-1,3,4-oxadiazol-2-yl)pyrimidin-4-yl)amino) propyl)-8-chloro-2-cyclopropylisoquinolin-1(2H)-one

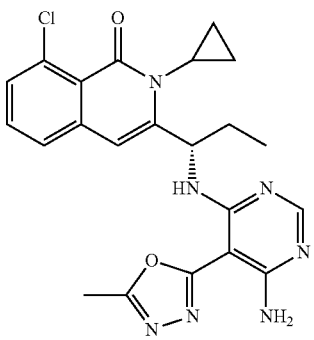 [SMILES: CC[C@H](Nc1ncnc(N)c1-c1nnc(C)o1)c1cc2cccc(Cl)c2c(=O)n1C1CC1]

To a suspension of (S)-3-(1-aminopropyl)-8-chloro-2-cyclopropylisoquinolin-1(2H)-one (80 mg, 0.29 mmol) and 6-chloro-5-(5-methyl-1,3,4-oxadiazol-2-yl)pyrimidin-4-amine (60 mg, 0.28 mmol) in n-BuOH (5 mL) was added DIPEA (90 mg, 0.58 mmol). The resulted mixture was heated at reflux for 24 hours, and the reaction was monitored by TLC (PE/EtOAc, v/v, 1/2). Then the mixture was cooled to room temperature and concentrated in vacuo. The residue was purified by a silica gel column chromatography (PE/EtOAc (v/v)=1/2) to give the title compound as a white solid (51 mg, 39%).

MS (ESI, pos, ion): 452.2 [M+H]$^+$; HPLC: 96.8%;

$^1$H NMR (600 MHz, CDCl$_3$) δ (ppm): 8.83 (d, J=7.0 Hz, 1H), 8.13 (d, J=11.5 Hz, 1H), 7.37 (dd, J=6.8, 3.6 Hz, 2H), 7.22 (dd, J=5.9, 3.2 Hz, 1H), 6.35 (s, 1H), 6.14 (s, 2H), 6.01 (td, J=8.5, 4.1 Hz, 1H), 3.13 (m, 1H), 2.69 (d, J=10.6 Hz, 3H), 1.87 (m, 1H), 1.52 (m, 1H), 1.45 (m, 1H), 1.32 (m, 1H), 1.13 (t, J=7.4 Hz, 3H). 0.91 (m, 2H).

Example 11 (S)-3-(1-((6-amino-5-(5-methyl-1,2,4-oxadiazol-3-yl)pyrimidin-4-yl)amino)ethyl)-8-chloro-2-cyclopropylisoquinolin-1(2H)-one

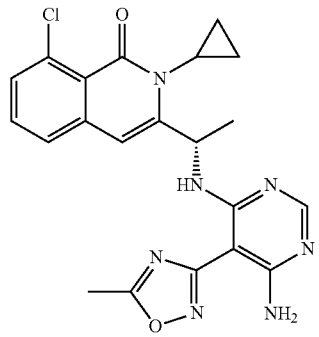 [SMILES: Cc1nc(-c2c(N)ncnc2N[C@@H](C)c2cc3cccc(Cl)c3c(=O)n2C2CC2)no1]

To a suspension of (S)-3-(1-aminoethyl)-8-chloro-2-cyclopropylisoquinolin-1(2H)-one (80 mg, 0.30 mmol) and 6-chloro-5-(5-methyl-1,2,4-oxadiazol-3-yl)pyrimidin-4-amine (60 mg, 0.28 mmol) in n-BuOH (5 was added DIPEA (90 mg, 0.58 mmol). The resulting mixture was heated at reflux for 24 hours, and the reaction was monitored by TLC (PE/EtOAc, v/v, 1/2). Then the mixture was cooled to room temperature and concentrated in vacuo. The residue was purified by a silica gel column chromatography (PE/EtOAc (v/v)=1/2) to give the title compound as a white solid (42 mg, 35%).

MS (ESI, pos, ion): 438.1 [M+H]$^+$; HPLC: 96.3%;

$^1$H NMR (400 MHz, CDCl$_3$) δ (ppm): 8.35 (d, J=6.5 Hz, 1H), 8.12 (s, 1H), 7.51-7.33 (m, 2H), 7.25 (m, 1H), 6.42 (s, 1H), 6.20-6.07 (m, 1H), 3.01 (s, 1H), 2.73 (s, 3H), 1.65 (m, 3H), 1.44 (m, 2H), 0.91 (m 2H).

Example 12 (S)-3-(1-((6-amino-5-(2-methyl-2H-tetrazol-5-yl)pyrimidin-4-yl)amino)ethyl)-8-chloro-2-cyclopropylisoquinolin-1(2H)-one

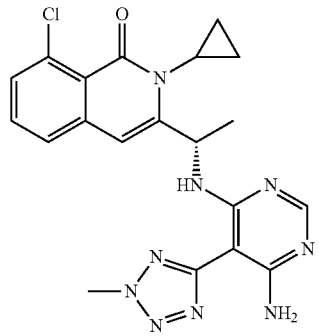 [SMILES: C[C@H](Nc1ncnc(N)c1-c1nnn(C)n1)c1cc2cccc(Cl)c2c(=O)n1C1CC1]

Step 1) 5-iodo-2-methyl-2H-tetrazole

To a mixture of 2-methyl-2H-tetrazol-5-amine (15.0 g, 153 mmol), CH$_2$I$_2$ (62 mL, 765 mmol) and CuI (29.0 g, 153 mmol) in THF (160 mL) was added isopentyl nitrite (62 mL, 549 mmol). The reaction mixture was heated to reflux and stirred further for 1 hour, then cooled to room temperature, and concentrated in vacuo. The residue was diluted with EtOAc (150 mL). The separated organic phase was washed with ammonium hydroxide (20 mL, 25% solution in water) and brine (10 mL), dried over anhydrous Na$_2$SO$_4$, and concentrated in vacuo. The residue was purified by a silica gel column chromatography (PE/EtOAc (v/v)=20/1) to give the title compound as a white solid (24.2 g, 76%).

MS (ESI, pos. ion.) mz: 211.0 [M+H]$^+$;
$^1$H NMR (400 MHz, CDCl$_3$) δ (ppm): 4.42 (s, 3H).

Step 2) 2-methyl-5-(tributylstannyl)-2H-tetrazole

To a solution of 5-iodo-2-methyl-2H-tetrazole (3.0 g, 14.3 mmol) in dried THF (70 mL) at −78° C. was added n-BuLi (2.5 M in hexane, 7.15 mL, 17.9 mmol) dropwise under N$_2$ atmosphere. The mixture was stirred at −78° C. for 30 minutes, and then tributyltinchloride (4.3 mL, 15.7 mmol) was added dropwise. The reaction mixture was stirred at −78° C. for another 30 minutes and then warmed to room temperature and stirred further for 2 hours. The mixture was quenched by the addition of a 5% NH$_4$Cl aqueous solution (30 mL) and extracted with EtOAc, (30 mL×3). The combined organic phases were washed with water (2 mL) and brine (2 mL), dried over anhydrous Na$_2$SO$_4$, and concentrated in vacuo. The residue was purified by a silica gel column chromatography (PE/EtOAc (v/v)=20/1) to give the title compound as colorless liquid (3.6 g, 68%).

MS (ESI, pos. ion.) mz: 375.1 [M+H]$^+$.

Step 3) 4,6-dimethoxy-5-(2-methyl-2H-tetrazol-5-yl)pyrimidine

A mixture of 2-methyl-5-(tributylstannyl)-2H-tetrazole (1.85 g, 4.96 mmol), 5-bromo-4,6-dimethoxypyrimidine (543 mg, 2.48 mmol) and 1,1'-bis(diphenyl-phosphino)ferrocene-palladium(II)dichloride dichloromethane complex (204 mg, 0.25 mmol) in dried DMF (10 nit) was heated to 120° C. and stirred for 24 hours under N$_2$ atmosphere, then cooled to room temperature. The reaction mixture was concentrated in vacuo. The residue was purified by a silica gel column chromatography (PE/EtOAc (v/v)=10/1) to afford the title compound as a white solid (300 mg, 55%).

MS (ESI, pos. ion.) mz: 223.2 [M+H]$^+$;
$^1$H NMR (600 MHz, CDCl$_3$) δ (ppm): 8.55 (s, 1H), 4.45 (s, 3H), 4.00 (s, 6H).

Step 4) 5-(2-methyl-2H-tetrazol-5-yl)pyrimidine-4,6-diol

To a solution of 4,6-dimethoxy-5-(2-methyl-2H-tetrazol-5-yl)pyrimidine (65 mg, 0.29 mmol) in acetic acid (1 mL) was added concentrated hydrochloride acid (12 M, 1 The reaction was heated to reflux for 4 hours, then cooled to room temperature. The reaction mixture was concentrated in vacuo to give the title compound as a white solid (53 mg, 95%).

MS (ESI, pos. ion.) mz: 195.1 [M+H]$^+$.

Step 5) 4,6-dichloro-5-(2-methyl-2H-tetrazol-5-yl)pyrimidine

To a solution of 5-(2-methyl-2H-tetrazol-5-yl)pyrimidine-4,6-diol (53 mg, 0.27 mmol) in POCl$_3$ (2 mL) was added DMF (0.3 mL), The reaction was heated to reflux and stirred further for 5 hours, then concentrated in vacuo to remove the excess POCl$_3$. To the residue was added 2 g of ice water and the resulted mixture was extracted with EtOAc (5 mL×3). The combined organic phases were washed with H$_2$O (1 mL), dried over anhydrous Na$_2$SO$_4$, and concentrated in vacuo to obtain the title compound as brown syrup (57 mg, 91%) which was used in the next step without further purification.

MS (ESI, pos. ion.) mz: 231.0 [M+H]$^+$.

Step 6) 6-chloro-5-(2-methyl-2H-tetrazol-5-yl)pyrimidin-4-amine

To a solution of 4,6-dichloro-5-(2-methyl-2H-tetrazol-5-yl)pyrimidine (65 mg, 0.28 mmol) in THF (3 nit) was bubbled through NH$_3$ gas overnight with stirring. The mixture was concentrated in vacuo and the residue was dissolved in EtOAc (5 mL). The resulted mixture was washed with H$_2$O (1 mL) and brine (1 mL), and the separated organic phase was dried over anhydrous Na$_2$SO$_4$, and concentrated in vacuo. The residue was purified by a silica gel column chromatography (hexane/EtOAc (v/v)=2/1) to afford the title compound as a white solid (34 mg, 56%).

MS (ESI, pos. ion.) mz: 212.1 [M+H]$^+$;
$^1$H NMR (600 MHz, CDCl$_3$) δ (ppm): 8.40 (s, 1H), 4.51 (s, 3H).

Step 7) (S)-3-(1-((6-amino-5-(2-methyl-2H-tetrazol-5-yl)pyrimidin-4-yl)amino)ethyl)-8-chloro-2-cyclopropylisoquinolin-1(2H)-one To a solution of 6-chloro-5-(2-methyl-2H-tetrazol-5-yl)pyrimidin-4-amine (60 mg, 0.284 mmol) and (S)-3-(1-aminoethyl)-8-chloro-2-cyclopropylisoquinolin-1(2H)-one (78.3 mg, 0.298 mmol) in 5 mL of n-BuOH was added DIPEA (0.2 mL, 0.568 mmol). The mixture was stirred at 120° C. for 36 hours, then cooled to room temperature, and concentrated in vacuo. The residue was dissolved in EtOAc (20 mL) and the resulted mixture was washed with water (15 mL) and brine (15 mL). The separated organic phase was dried over anhydrous Na$_2$SO$_4$, and concentrated in vacuo. The residue was purified by a silica gel column chromatography (PE/EtOAc (v/v)=3/1) to give the title compound as an off-white solid (66 mg, 53%).

MS (ESI, pos. ion) mz: 438.1 [M+H]$^+$;
$^1$H NMR (400 MHz, CDCl$_3$) δ (ppm): 8.57 (d, J=6.8 Hz, 1H), 8.15 (s, 1H), 7.42-7.34 (m, 2H), 7.23 (dd, J=6.5, 2.6 Hz, 1H), 6.44 (s, 1H), 6.22-6.12 (m, 1H), 4.50 (s, 3H), 3.55 (s, 2H), 3.06-2.97 (m, 1H), 1.68 (d, J=6.8 Hz, 3H), 1.51-1.39 (m, 2H), 0.97-0.89 (m, 2H).

Example 13 (S)-3-(1-((6-amino-5-(2-methyl-2H-tetrazol-5-yl)pyrimidin-4-yl)amino)propyl)-8-chloro-2-cyclopropylisoquinolin-1(2H)-one

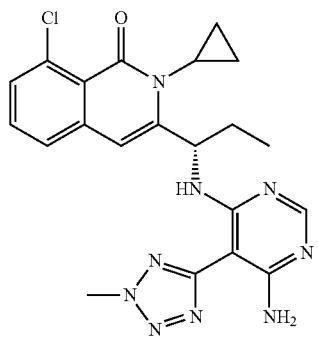 [SMILES: CC[C@H](Nc1ncnc(N)c1-c1nnn(C)n1)c1cc2cccc(Cl)c2c(=O)n1C1CC1]

To a suspension of 6-chloro-5-(2-methyl-2H-tetrazol-5-yl)pyrimidin-4-amine (60 mg, 0.284 mmol) and (S)-3-(1-aminopropyl)-8-chloro-2-cyclopropylisoquinolin-1(2H)-one (82.5 mg, 0.298 mmol) in 5 mL of n-BuOH was added DIPEA (0.2 mL, 0.568 mmol). The mixture was stirred at 120° C. for 36 hours, then cooled to room temperature, and concentrated in vacuo. The residue was dissolved in EtOAc (20 mL), and the resulted mixture was washed with water (15 mL) and brine (15 nit), The organic phase was dried over anhydrous Na$_2$SO$_4$, and concentrated in vacuo. The residue was purified by a silica gel column chromatography (DCM/MeOH (v/v)=20/1) to give the title compound as an off-white solid (32 mg, 24.9%).

MS (ESI, pos. ion) mz: 452.1 [M+H]$^+$;

$^1$H NMR (400 MHz, CDCl$_3$) δ (ppm): 8.66 (d, J=7.3 Hz, 1H), 8.14 (s, 1H), 7.43-7.32 (m, 2H), 7.20 (dd, J=6.8, 2.2 Hz, 1H), 6.37 (s, 1H), 6.05 (d, J=8.0 Hz, 1H), 4.52 (s, 3H), 3.65-3.42 (m, 2H), 3.04 (s, 1H), 2.07 (s, 2H), 1.42 (dd, J=13.2, 7.1 Hz, 2H), 1.15 (t, J=7.4 Hz, 2H), 0.90 (t, J=6.7 Hz, 3H).

Example 14 (S)-butyl 3-(4-amino-6-((1-(8-chloro-2-cyclopropyl-1-oxo-1,2-dihydroisoquinolin-3-yl)propyl)amino)pyrimidin-5-yl)-1-methyl-1H-1,2,4-triazole-5-carboxylate

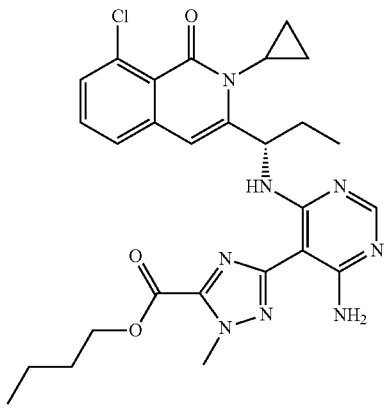 [SMILES: CCCCOC(=O)c1nc(-c2c(N)ncnc2N[C@@H](CC)c2cc3cccc(Cl)c3c(=O)n2C2CC2)nn1C]

Step 1) ethyl 3-(4,6-dichloropyrimidin-5-yl)-1-methyl-1H-1,2,4-triazole-5-carboxylate To a solution of ethyl 3-(4,6-dimethoxypyrimidin-5-methyl-1H-1,2,4-triazole-5-carboxylate (500 mg, 1.70 mmol) in toluene (25 mL) were added POCl$_3$ (2 mL, 17.0 mmol) and DMF (4 mL). The mixture was stirred at 120° C. for 48 hours, then cooled to room temperature, and concentrated in vacuo. The residue was purified by a silica gel column chromatography (PE/EtOAc (v/v)=10/1) to give the title compound as pale yellow oil (375 mg, 73%).

MS (ESI, pos. ion): 303.1 [M+H]$^+$.

Step 2) ethyl 3-(4-amino-6-chloropyrimidin-5-yl)-1-methyl-1H-1,2,4-triazole-5-carboxylate To a solution of ethyl 3-(4,6-dichloropyrimidin-5-yl)-1-methyl-1H-1,2,4-triazole-5-carboxylate (375 mg, 1.24 mmol) in dried THF (20 mL) was bubbled with NH$_3$ gas and stirred at room temperature for 5 hours. The reaction was monitored by TLC (EtOAc), The mixture was filtered and the filter cake was washed with EtOAc (10 mL). The filtrate was concentrated in vacuo to give the title compound as a white solid (320 mg, 91.2%).

MS (ESI, pos. ion): 283.1 [M+H]$^+$;

$^1$H NMR (400 MHz, CDCl$_3$) δ (ppm): 8.35 (s, 1H), 4.53 (q, J=7.1 Hz, 2H), 4.36 (s, 3H), 1.69 (s, 2H), 1.49 (t, J=7.1 Hz, 3H).

Step 3) (S)-butyl 3-(4-amino-6-((1-(8-chloro-2-cyclopropyl-1-oxo-1,2-dihydroisoquinolin-3-yl)propyl)amino)pyrimidin-5-yl)-1-methyl-1H-1,2,4-triazole-5-carboxylate To a suspension of ethyl 3-(4-amino-6-chloropyrimidin-5-yl)-1-methyl-1H-1,2,4-triazole-5-carboxylate (60 mg, 0.212 mmol) and (S)-3-(1-aminopropyl)-8-chloro-2-cyclopropylisoquinolin-1(2H)-one (61.4 mg, 0.222 mmol) in 5 mL of n-BuOH was added DIPEA (0.2 mL, 0.424 mmol). The mixture was stirred at 160° C. in a sealed tube for 24 hours, then concentrated in vacuo, and the residue was dissolved in EtOAc (15 mL). The resulted mixture was washed with water (15 mL) and brine (15 mL). Then the organic phase was concentrated in vacuo, and the residue was purified by a silica gel column chromatography (PE/EtOAc (v/v)=3/1) to give the title compound as a white solid (34 mg, 29%).

MS (ESI, pos. ion) mz: 551.2 [M+H]$^+$; HPLC: 95.6%;

$^1$H NMR (400 MHz, CDCl$_3$) δ (ppm): 9.32 (d, J=6.8 Hz, 1H), 8.08 (s, 1H), 7.35 (q, J=7.3 Hz, 2H), 7.20 (dd, J=7.0, 2.1 Hz, 1H), 6.38 (s, 1H), 6.01 (m, 1H), 4.47-4.40 (m, 2H), 4.36 (s, 3H), 3.03 (m, 1H), 2.13-2.00 (m, 2H), 1.91-1.80 (m, 1H), 1.77 (dd, J=14.7, 6.8 Hz, 3H), 1.63 (m, 1H), 1.53-1.38 (m, 3H), 1.38-1.32 (m, 1H), 1.14 (t, J=7.4 Hz, 3H), 0.95 (t, J=7.4 Hz, 3H), 0.93-0.84 (m, 1H).

Example 15 (S)-3-(1-((6-amino-5-(2-methyl-2H-tetrazol-5-yl)pyrimidin-4-yl)amino)ethyl)-8-chloro-2-phenylisoquinolin-1(2H)-one

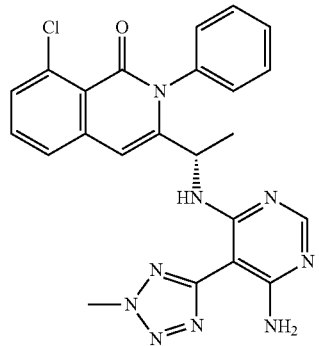 [SMILES: C[C@H](Nc1ncnc(N)c1-c1nnn(C)n1)c1cc2cccc(Cl)c2c(=O)n1-c1ccccc1]

To a suspension of 6-chloro-5-(2-methyl-2H-tetrazol-5-yl)pyrimidin-4-amine (30 mg, 0.142 mmol) and (S)-3-(1-aminoethyl)-8-chloro-2-phenylisoquinolin-1(2H)-one (44 mg, 0.149 mmol) in n-BuOH (3 mL) was added DIPEA (37 mg, 0.284 mmol). The resulted mixture was heated at reflux for 42 hours and monitored by TLC (PE/EtOAc, v/v, 1/3). The mixture was cooled to room temperature and concentrated in vacuo. The residue was diluted with EtOAc (15 mL), washed with water (15 mL) and brine (10 mL). The organic phase was dried over anhydrous Na$_2$SO$_4$ and concentrated in vacuo. The residue was purified by a preparative TLC (PE/EtOAc (v/v)=1/4) to give the title compound as a pale yellow solid (35 mg, 52.1%).

MS (ESI, pos. ion): 474.1 [M+H]$^+$; HPLC: 91.4%;

$^1$H NMR (400 MHz, CDCl$_3$) δ (ppm): 8.79 (d, J=6.8 Hz, 1H), 8.01 (s, 1H), 7.56-7.32 (m, 8H), 6.58 (s, 1H), 5.11 (d, J=6.9 Hz, 1H), 4.52 (s, 3H), 1.53 (d, J=6.8 Hz, 3H).

Example 16 (S)-3-(1-((6-amino-5-(1-methyl-1H-1,2,4-triazol-3-yl)pyrimidin-4-yl)amino)ethyl)-8-chloro-2-cyclopropylisoquinolin-1(2H)-one

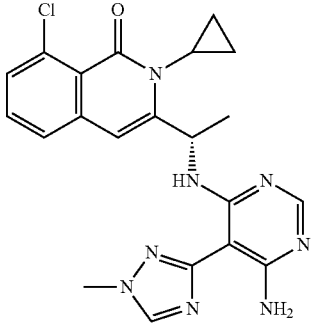 [SMILES: C[C@H](Nc1ncnc(N)c1-c1ncn(C)n1)c1cc2cccc(Cl)c2c(=O)n1C1CC1]

To a suspension of 6-chloro-5-(1-methyl-1H-1,2,4-triazol-3-yl)pyrimidin-4-amine (31 mg, 0.147 mmol) and (S)-3-(1-aminoethyl)-8-chloro-2-cyclopropylisoquinolin-1(2H)-one (41 mg, 0.155 mmol) in n-BuOH (3 mL) was added DIPEA (38 mg, 0.294 mmol). The resulted mixture was heated at reflux for 20 hours. The reaction was monitored by TLC (CH$_2$Cl$_2$/MeOH, v/v, 25/1). The mixture was cooled to room temperature and concentrated in vacuo. The residue was diluted with EtOAc (15 mL), and the resulted mixture was washed with water (15 mL) and brine (10 mL). The separated organic phase was dried over anhydrous Na$_2$SO$_4$, and concentrated in vacuo. The residue was purified by a silica gel column chromatography (DCM/MeOH (v/v)=200/3) to give the title compound as a pale yellow solid (32 mg, 51.4%).

MS (ESI, pos, ion): 437.2 [M+H]$^+$; HPLC: 94.9%;
$^1$H NMR (400 MHz, CDCl$_3$) δ (ppm): 9.59 (d, J=6.9 Hz, 1H), 8.18 (s, 1H), 8.11 (s, 1H), 7.44-7.36 (m, 2H), 7.25 (dd, J=6.5, 2.5 Hz, 1H), 6.43 (s, 1H), 6.20-6.09 (m, 1H), 4.06 (s, 3H), 2.98 (dt, J=6.8, 5.7 Hz, 1H), 1.68 (d, J=6.7 Hz, 3H), 1.34-1.30 (m, 2H), 0.96-0.86 (m, 2H).

Example 17 (S)-3-(1-((6-amino-5-(5-(methoxymethyl)-1-methyl-1H-1,2,4-triazol-3-yl) pyrimidin-4-yl)amino)propyl)-8-chloro-2-cyclopropylisoquinolin-1(2H)-one

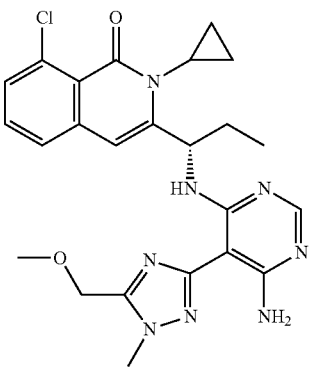 [SMILES: CC[C@H](Nc1ncnc(N)c1-c1nc(COC)n(C)n1)c1cc2cccc(Cl)c2c(=O)n1C1CC1]

To a suspension of 6-chloro-5-(5-(methoxymethyl)-1-methyl-1H-1,2,4-triazol-3-yl)pyrimidin-4-amine (25 mg, 0.098 mmol) and (S)-3-(1-aminopropyl)-8-chloro-2-cyclopropylisoquinolin-1(2H)-one (40 mg, 0.145 mmol) in n-BuOH (3 mL) was added DIPEA (25 mg, 0.196 mmol). The resulted mixture was heated at reflux for 16 hours. The reaction was monitored by TLC (CH$_2$Cl$_2$/MeOH, v/v, 25/1). The mixture was cooled to room temperature and concentrated in vacuo. The residue was diluted with EtOAc (15 mL), and the resulted mixture was washed with water (15 mL) and brine (10 mL), The separated organic phase was dried over anhydrous Na$_2$SO$_4$ and concentrated in vacuo. The residue was purified by a preparative TLC (CH$_2$Cl$_2$/MeOH (v/v)=25/1) to give the title compound as a light pink solid (19 mg, 39.1%).

MS (ESI, pos, ion): 495.2 [M+H]$^+$; HPLC: 93.7%;
$^1$H NMR (400 MHz, CDCl$_3$) δ (ppm): 9.26 (d, J=6.6 Hz, 1H), 8.06 (s, 1H), 7.42-7.32 (m, 2H), 7.20 (dd, J=6.7, 2.3 Hz, 1H), 6.38 (s, 1H), 5.99 (td, J=7.5, 4.5 Hz, 1H), 4.71 (s, 2H), 4.04 (s, 3H), 3.48 (s, 3H), 3.09-2.95 (m, 1H), 2.06-2.00 (m, 1H), 1.65-1.56 (m, 1H), 1.36-1.32 (m, 2H), 1.13 (t, J=7.3 Hz, 3H), 0.90-0.82 (m, 2H).

Example 18 (S)-3-(1-((6-amino-5-(5-methyl-1,2,4-oxadiazol-3-yl)pyrimidin-4-yl)amino) propyl)-8-fluoro-2-phenylisoquinolin-1(2H)-one

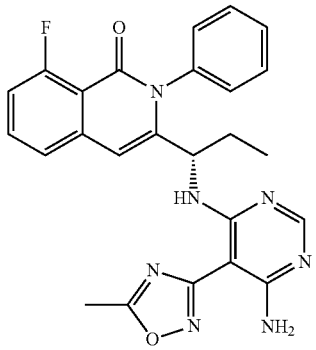 [SMILES: CC[C@H](Nc1ncnc(N)c1-c1noc(C)n1)c1cc2cccc(F)c2c(=O)n1-c1ccccc1]

Step 1) 2-fluoro-6-methyl-N-phenylbenzamide

To a suspension of 2-fluoro-6-methylbenzoic acid (7.7 g, 50.0 mmol) in toluene (50 mL) was added SOCl$_2$ (23.8 g, 200 mmol), and then the mixture was heated to reflux and stirred further for 12 hours. The reaction mixture was concentrated in vacuo, and the residue was dissolved in anhydrous THF (30 mL), then a solution of aniline (4.7 g, 50 mmol) and Et$_3$N (15.2 g, 150 mmol) in anhydrous THF (30 mL) was added dropwise at 0° C. under N$_2$ atmosphere. Then the mixture was warmed to rt and stirred for another 5 hours, Filtered and the filtrate was concentrated in vacuo to give a brown solid which was washed with ethyl ether (10 mL×3) later to give the title compound as a white solid (10.7 g, 93%).

MS (ESI, pos. ion) mz: 230.1 [M+H]$^+$;
$^1$H NMR (600 MHz, CDCl$_3$) δ (ppm): 7.65 (d, J=7.9 Hz, 2H), 7.59 (br. s, 1H), 7.40 (t, J=7.8 Hz, 2H), 7.34-7.30 (m, 1H), 7.19 (t, J=7.4 Hz, 1H), 7.07 (d, J=7.6 Hz, 1H), 6.99 (t, J=8.9 Hz, 1H), 2.49 (s, 3H).

Step 2) (S)-3-(1-aminopropyl)-8-fluoro-2-phenylisoquinolin-1(2H)-one

To a stirred solution of 2-fluoro-6-methyl-N-phenylbenzamide (2.3 g, 10.0 mmol) in anhydrous THF (40 mL) was added a solution of n-butyllithium ire THF (25 mmol, 2.5 M) dropwise at −30° C. under nitrogen atmosphere over 10 minutes. The resulted mixture was then stirred at −30° C. for 30 minutes, and the solution was used for the below step.

To a stirred solution of (S)-tert-butyl(1-(methoxy(methyl) amino)-1-oxobutan-2-yl)carbamate (3.7 g, 15 mmol) in anhydrous THF (40 mL) was added a solution of isopropylmagnesium chloride in THF (16.5 mmol, 2.0 M) dropwise at −30° C. under nitrogen atmosphere over 10 minutes. The mixture was then stirred at −30° C. for 30 minutes, and then the above solution was added dropwise. The resulted mixture was then stirred at −15° C. for 4 hours, then quenched with water (20 mL) and adjusted to pH=1-3 with concentrated HCl. The mixture was concentrated in vacuo, and the residue was dissolved in MeOH (40 mL) and concentrated HCl (20 mL). The resulted mixture was heated to reflux for 2 hours, then concentrated in vacuo to remove the most of MeOH, and extracted with ethyl acetate (100 mL). The aqueous layer was basified to pH=7-8 with saturation NaHCO$_3$ aqueous solution, and then extracted with ethyl acetate (100 mL×3). The combined organic phases were dried over anhydrous Na$_2$SO$_4$, concentrated in vacuo and the residue was purified by a silica gel column chromatography (ethyl acetate) to give the title as a light yellow solid (2.32 g, 78%).

MS (ESI, pos. ion) mz: 297.2 [M+H]$^+$;

$^1$H NMR (600 MHz, DMSO-d$_6$) δ (ppm): 7.70 (td, J=8.0, 4.9 Hz, 1H), 7.58-7.53 (m, 2H), 7.50 (d, J=7.4 Hz, 1H), 7.47 (d, J=7.9 Hz, 1H), 7.36 (dd, J=7.2, 1.6 Hz, 1H), 7.31 (dd, J=5.4, 4.2 Hz, 1H), 7.17 (dd, J=11.5, 8.1 Hz, 1H), 6.87 (d, J=1.6 Hz, 1H), 3.16 (dd, J=7.6, 4.8 Hz, 1H), 1.81 (br. s, 2H), 1.61-1.53 (m, 1H), 1.30 (tt, J=14.7, 7.3 Hz, 1H), 0.65 (t, J=7.3 Hz, 3H);

$^{13}$C NMR (151 MHz, DMSO-d$_6$) δ (ppm): 163.0, 161.3, 159.82, 159.79, 151.5, 140.3, 138.4, 134.4, 134.3, 130.2, 129.8, 129.6, 129.4, 128.8, 122.6, 122.5, 113.53, 113.47, 113.0, 112.9, 101.59, 101.58, 53.3, 30.5, 11.2.

Step 3) (S)-3-(1-((6-amino-5-(5-methyl-1,2,4-oxadiazol-3-yl)pyrimidin-4-yl)amino)propyl)-8-fluoro-2-phenylisoquinolin-1(2H)-one A mixture of 6-chloro-5-(5-methyl-1,2,4-oxadiazol-3-yl) pyrimidin-4-amine (23.0 mg, 0.11 mmol), (S)-3-(1-aminopropyl)-8-fluoro-2-phenylisoquinotin-1(2H)-one (39.0 mg, 0.13 mmol) and N,N-diisopropylethylamine (42.6 mg, 0.33 mmol) ire n-butanol (2.0 mL) was heated to 150 in a sealed tube for 12 hours, then concentrated in vacuo, and the residue was purified by a silica gel column chromatography (PE/EtOAc (v/v)=1/2) to give the title compound as a white solid (47 mg, 91%).

MS (ESI, pos. ion) m/z: 472.2 [M+H]$^+$; HPLC: 99.61%;

$^1$H NMR (600 MHz, CDCl$_3$) δ (ppm): 8.32 (d, J=6.3 Hz, 1H), 8.06 (s, 1H), 7.90 (br. s, 1H), 7.62 (d, J=7.3 Hz, 1H), 7.57-7.50 (m, 3H), 7.49-7.45 (m, 1H), 7.38-7.33 (m, 1H), 7.21 (d, J=8.0 Hz, 1H), 7.05 (dd, J=11.2, 8.1 Hz, 1H), 6.48 (s, 1H), 5.56 (br. s, 1H), 4.85-4.79 (m, 1H), 2.74 (s, 3H), 1.85 (ddt, J=14.7, 11.4, 7.4 Hz, 1H), 1.67 (dq, J=22.3, 7.4 Hz, 1H), 0.87 (t, J=7.4 Hz, 3H);

$^{13}$C NMR (151 MHz, CDCl$_3$) δ (ppm): 174.3, 166.0, 163.6, 161.8, 161.3, 160.83, 160.79, 159.7, 158.5, 147.1, 139.7, 137.5, 133.33, 133.25, 129.43, 129.36, 129.1, 128.7, 121.7, 121.6, 114.4, 114.3, 113.1, 112.0, 101.63, 101.60, 82.6, 53.3, 28.3, 12.4, 10.7.

Example 19 (S)-3-(1-((6-amino-5-(isoxazol-3-yl) pyrimidin-4-yl)amino)propyl)-8-fluoro-2-phenylisoquinolin-1(2H)-one

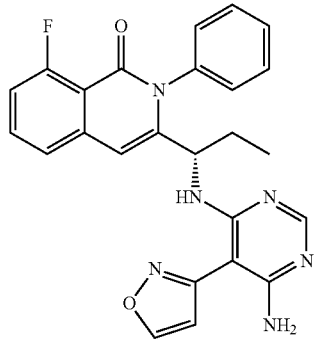 [SMILES: CC[C@H](Nc1ncnc(N)c1-c1ccon1)c1cc2cccc(F)c2c(=O)n1-c1ccccc1]

A mixture of 6-chloro-5-(isoxazol-3-yl)pyrimidin-4-amine (49.1 mg, 0.25 (S)-3-(1-aminopropyl)-8-fluoro-2-phenylisoquinolin-1(2H)-one (88.9 mg, 0.30 mmol) and N,N-diisopropylethylamine (96.9 mg, 0.75 mmol) in n-butanol (2.0 mL) was heated to 150 in a sealed tube for 36 hours. After completion, the reaction mixture was concentrated in vacuo and the residue was purified by a silica gel column chromatography (EtOAc) to give the title compound as a white solid (15 mg, 13%).

MS (ESI, pos. ion) m/z: 457.2 [M+H]$^+$; HPLC: 96.41%;

$^1$H NMR (600 MHz, CDCl$_3$) δ (ppm): 8.60 (s, 1H), 8.05 (s, 1H), 7.60-7.43 (m, 5H), 7.31 (d, J=7.8 Hz, 1H), 7.25 (s, 1H), 7.24 (d, J=8.0 Hz, 1H), 7.06 (dd, J=11.1, 8.2 Hz, 1H), 6.85 (d, J=1.1 Hz, 1H), 6.48 (d, J=1.2 Hz, 1H), 5.58 (br. s, 2H), 4.77 (dd, J=11.5, 7.7 Hz, 1H), 1.87-1.79 (m, 1H), 1.62 (dq, J=22.3, 7.3 Hz, 1H), 0.83 (t, J=7.3 Hz, 3H).

Example 20 (S)-3-(1-((6-amino-5-(1-methyl-1H-1,2, 4-triazol-3-yl)pyrimidin-4-yl)amino) propyl)-8-chloro-2-cyclopropylisoquinolin-1(2H)-one

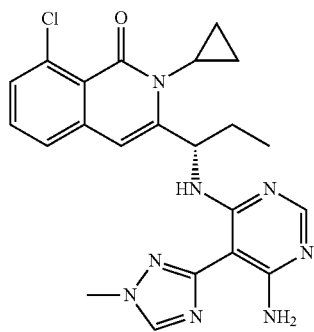 [SMILES: CC[C@H](Nc1ncnc(N)c1-c1ncn(C)n1)c1cc2cccc(Cl)c2c(=O)n1C1CC1]

To a suspension of (S)-3-(1-aminopropyl)-8-chloro-2-cyclopropylisoquinolin-1(2H)-one (55.4 mg, 0.2 mmol) and 6-chloro-5-(1-methyl-1H-1,2,4-triazol-3-yl)pyrimidin-4-amine (42 mg, 0.2 mmol) in n-BuOH (2 mL) was added DIPEA (51.7 mg, 0.4 mmol). The reaction mixture was heated to reflux and stirred further for 24 hours, then cooled to room temperature and concentrated in vacuo. The residue was dissolved in EtOAc (10 mL), and the resulted mixture was washed with water (10 mL×2) and brine (10 mL), The separated organic phase was dried over Na$_2$SO$_4$, and concentrated in vacuo. The residue was purified by a silica gel column chromatography (CH$_2$Cl$_2$/MeOH (v/v)=100/2) to give the title compound as a white solid (26.7 mg, 29.6%).

MS (ESI, pos. ion) mz: 451.2 [M+H]$^+$;

¹H NMR (400 MHz, CDCl₃) δ (ppm): 8.17 (s, 1H), 8.08 (s, 1H), 7.35 (m, 2H), 7.20 (dd, J=6.8, 2.2 Hz, 1H), 6.38 (s, 1H), 5.99 (td, J=7.7, 4.1 Hz, 1H), 4.05 (s, 3H), 3.02 (ddd, J=11.0, 7.1, 4.2 Hz, 1H), 1.83 (m, 1H), 1.60 (m, 1H), 1.33 (m, 2H), 1.13 (t, J=7.4 Hz, 3H), 0.93 (m, 2H).

Example 21 (S)-3-(1-((6-amino-5-(5-methyl-1,2,4-oxadiazol-3-yl)pyrimidin-4-yl)amino) propyl)-8-chloro-2-cyclopropylisoquinolin-1(2H)-one

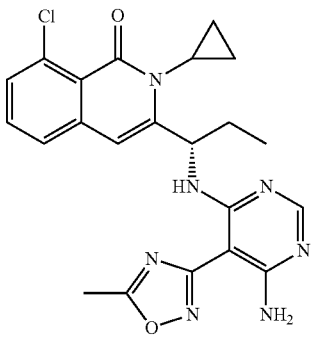 [SMILES: CC[C@H](Nc1ncnc(N)c1-c1noc(C)n1)c1cc2cccc(Cl)c2c(=O)n1C1CC1]

To a suspension of (S)-3-(1-aminopropyl)-8-chloro-2-cyclopropylisoquinolin-1(2H)-one 55.4 mg, 0.2 mmol) and 6-chloro-5-(5-methyl-1,2,4-oxadiazol-3-yl)pyrimidin-4-amine (42.3 mg, 0.2 mmol) in n-BuOH (2 mL) was added DIPEA (51.7 mg, 0.4 mmol). The reaction mixture was heated to reflux overnight, then cooled to room temperature and concentrated in vacuo. The residue was dissolved in EtOAc (10 mL), and the resulted mixture was washed with water (10 mL×2) and brine (10 mL). The separated organic phase was dried over Na₂SO₄ and concentrated in vacuo. The residue was purified by a silica gel column chromatography (CH₂Cl₂/MeOH (v/v)=80/1) to afford the title compound as a pale yellow solid (43 mg, 47.6%).

MS (ESI, pos, ion) mz: 452.2 [M+H]⁺;
¹H NMR (400 MHz, CDCl₃) δ (ppm): 8.42 (d, J=6.8 Hz, 1H), 8.10 (s, 1H), 7.37 (m, 2H), 7.23 (dd, J=6.3, 2.9 Hz, 1H), 6.35 (s, 1H), 6.00 (td, J=7.9, 4.2 Hz, 1H), 3.02 (ddd, J=11.0, 7.2, 4.1 Hz, 1H), 2.75 (s, 3H), 2.06 (m, 2H), 1.84 (m, 2H), 1.57 (m, 1H), 1.40 (m, 1H), 1.13 (t, J=7.4 Hz, 3H).

Example 22 (S)-3-(1-((6-amino-5-(3-ethyl-1,2,4-oxadiazol-5-yl)pyrimidin-4-yl)amino) propyl)-8-chloro-2-cyclopropylisoquinolin-1(2H)-one

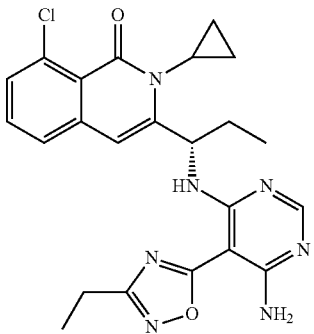 [SMILES: CCc1noc(-c2c(N)ncnc2N[C@@H](CC)c2cc3cccc(Cl)c3c(=O)n2C2CC2)n1]

To a suspension of(S)-3-(1-aminopropyl)-8-chloro-2-cyclopropylisoquinolin-1(2H)-one (70 mg, 0.252 mmol) and 6-chloro-5-(3-ethyl-1,2,4-oxadiazol-5-yl) amine (55 mg, 0.243 mmol) in n-BuOH (4 mL) was added DIPEA (75 rag, 0.580 mmol). The resulting mixture was heated at reflux for 12 hours. The reaction was monitored by TLC (PE/EtOAc, v/v, 1/1). After the reaction was completed, the mixture was cooled to room temperature and concentrated in vacuo. The residue was purified by a silica gel column chromatography (PE/EtOAc (v/v)=2/1) to give the title compound as a white solid (62 mg, 55%).

MS (ESI, pos, ion) mz: 466.2 [M+H]⁺; HPLC: 98.9%;
¹H NMR (400 MHz, CDCl₃) δ (ppm): 8.71 (d, J=5.6 Hz, 1H), 8.14 (s, 1H), 7.40-7.36 (m, 2H), 7.26-7.23 (m, 1H), 6.34 (s, 1H), 6.05-6.00 (m, 1H), 3.03 (m, 1H), 2.90 (q, J=7.4 Hz, 2H), 2.06 (s, 2H), 1.85-1.81 (m, 1H), 1.51-1.48 (m, 1H), 1.42 (t, J=7.4 Hz, 3H), 1.38 (m, 2H), 1.13 (t, J=7.1 Hz, 3H), 0.96-0.88 (m, 2H).

Example 23 (S)-3-(1-((6-amino-5-(3-methyl-1,2,4-oxadiazol-5-yl)pyrimidin-4-yl)amino)ethyl)-8-chloro-2-(3-fluorophenyl)isoquinolin-1(2H)-one

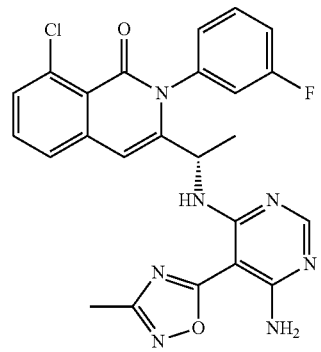 [SMILES: Cc1noc(-c2c(N)ncnc2N[C@@H](C)c2cc3cccc(Cl)c3c(=O)n2-c2cccc(F)c2)n1]

Step 1)
2-chloro-N-(3-fluorophenyl)-6-methylbenzamide

To a suspension of 2-chloro-6-methylbenzoic acid (2.0 g, 11.72 mind) in toluene (20 mL) was added SOCl₂ (3.4 mL, 46.90 mmol) at rt. The reaction was heated to reflux and stirred further for 6 hours, then cooled to it and concentrated in vacuo. The residue was dissolved in DCM (20 mL), then to the resulted solution were added triethylamine (3.4 mL, 24.66 mmol) and 3-fluoroaniline (1.3 g, 11.74 mmol) dropwise at 0° C. The mixture was stirred at rt overnight, then washed with saturated. NaHCO₃ aqueous solution (25 mL) and brine (20 mL). The separated organic phase was dried over anhydrous Na₂SO₄, and concentrated in vacuo. The residue was purified by a silica gel column chromatography (PE/EtOAc (v/v)=10/1) to give the title compound as a pink solid (2.55 g, 82.3%).

¹H NMR (400 MHz, DMSO-d₆) δ (ppm): 10.79 (s, 1H), 7.69 (dt, J=11.6, 2.2 Hz, 1H), 7.44 (ddd, J=7.5, 4.5, 2.9 Hz, 1H), 7.41-7.35 (m, 3H), 7.34-7.28 (m, 1H), 7.00-6.93 (m, 1H), 2.32 (s, 3H).

Step 2) (S)-3-(1-aminoethyl)-8-chloro-2-(3-fluorophenyl)isoquinolin-1(2H)-one

To a solution of 2-chloro-N-(3-fluorophenyl)-6-methylbenzamide (2.5 g, 9.48 mmol) in THF (30 mL) was added 2.4 M n-BuLi in hexanes (9.88 mL, 23.70 mmol) dropwise at −30° C. under N₂ atmosphere. The resulted dark orange mixture was stirred at this temperature for 30 minutes. To a solution of (S)-tert-butyl(1-(methoxy(methyl)amino)-1-oxopropan-2-yl)carbamate (3.3 g, 14.22 mmol) in THF (30 mL) was added 2 M i-PrMgCl in THF (7.11 mL, 14.22 mmol)

dropwise at −30° C. under N$_2$ atmosphere. The resulted mixture was stirred at −30° C. for another 30 minutes. This solution was added to above reaction mixture dropwise at −30° C. The resulted mixture was warmed to −15° C. and stirred further for 4 hours, then quenched with H$_2$O (20 mL). The mixture was acidified to pH=1-2 with conc. HCl at 0° C. and concentrated in vacuo. The residue was dissolved in MeOH (50 mL) and then was added conc. HCl aqueous solution (30 mL). The resulted mixture was stirred at reflux for 1.5 hours, then cooled to rt and concentrated in vacuo. The residue was diluted with H$_2$O (40 mL), then the mixture was neutralized to pH=7-8 with solid Na$_2$CO$_3$ and extracted with EtOAc (100 mL×2). The combined organic phase was washed with brine (100 mL), dried over Na$_2$SO$_4$, and concentrated in vacuo. The residue was purified by a silica gel column chromatography (DCM/MeOH (v/v)=1001) to give the title compound as a orange-yellow solid (2.5 g, yield 64.2%).

MS (ESI, pos. ion) mz: 317.2 [M+H]$^+$.

Step 3) (S)-3-(1-((6-amino-5-(3-methyl-1,2,4-oxadi-azol-5-yl)pyrimidin-4-yl)amino)ethyl)-8-chloro-2-(3-fluorophenyl)isoquinolin-1(2H)-one To a suspension of 6-chloro-5-(3-methyl-1,2,4-oxadiazol-5-yl)pyrimidin-4-amine (50 mg, 0.236 mmol) and (S)-3-(1-aminoethyl)-8-chloro-2-(3-fluorophenyl)isoquinolin-1(2H)-one (85 mg, 0.268 mmol) was added DIPEA (61 mg, 0.473 mmol). The reaction mixture was heated to reflux and stirred further for 4 hours. The reaction was monitored by TLC (PE/EtOAc, v/v, 1/3). The reaction mixture was cooled down to rt and concentrated in vacuo. The residue was diluted with DCM (20 mL), and the resulted mixture was washed with water (15 mL) and brine (10 mL). The separated organic phase was dried over Na$_2$SO$_4$ and concentrated in vacuo. The residue was purified by a preparative TLC (PE/EtOAc (v/v)=13) to give the title compound as a pale yellow solid (51 mg, yield 43.9%).

MS (ESI, pos, ion): 492.2 [M+H]$^+$; HPLC: 96.9%;
$^1$H NMR (600 MHz, CDCl$_3$) δ(ppm): 8.30 (d, J=5.6 Hz, 1H), 8.06 (d, J=11.9 Hz, 1H), 7.57-7.44 (m, 3H), 7.45-7.35 (m, 2H), 7.33-7.29 (m, 1H), 7.28-7.25 (m, 1H), 7.19-7.08 (m, 2H), 6.55 (s, 1H), 5.07-4.91 (m, 1H), 2.51 (d, J=1.5 Hz, 3H), 1.49 (dd, J=6.7, 5.4 Hz, 3H).

Example 24 (S)-3-(1-(((6-amino-5-(3-methyl-1,2,4-oxadiazol-5-yl)pyrimidin-4-yl)amino)ethyl)-8-chloro-2-cyclopropylisoquinolin-1(2H)-one

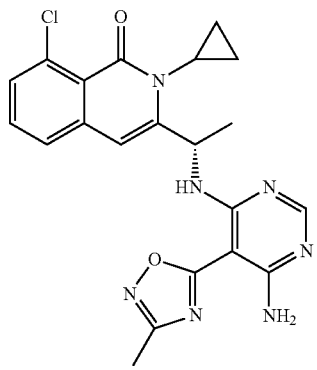 [SMILES: Cc1noc(-c2c(N)ncnc2N[C@@H](C)c2cc3cccc(Cl)c3c(=O)n2C2CC2)n1]

Step 1) 4,6-dichloropyrimidine-5-carbonyl chloride

To a solution of 4,6-dichloropyrimidin-5-carbaldehyde (10 g, 56.50 mmol) in carbon tetrachloride (100 mL) were added sulfuryl chloride (11.44 g, 84.75 mmol) and 2,2-azobis(2-methylpropionitrile) (0.464 g, 2.83 mmol). The mixture was stirred at 80° C. for 4.5 hours, then cooled to room temperature and filtered. The filtrate was concentrated in vacuo and the residue was dried under a reduced pressure to obtain the title compound as a yellow colloid (12.22 g, yield: 100%).

Step 2) 4,6-dichloropyrimidine-5-carboxamide

A solution of 4,6-dichloropyrimidine-5-carbonyl chloride (36 g, 170 mmol) in THF (200 mL) under NH$_3$ gas atmosphere was stirred at rt. The reaction was monitored by TLC until the stating material disappeared. The reaction mixture was concentrated in vacuo and the residue was partitioned between EtOAc (300 mL) and H$_2$O (100 mL). The aqueous phase was extracted with EtOAc (100 mL×2). The combined organic phase was washed with brine (100 mL), dried over anhydrous Na$_2$SO$_4$ and concentrated in vacuo to give the title compound as a yellow solid (27.2 g, yield: 83.2%).

MS (ESI, pos. ion) mz: 191.9 [M+H]$^+$;
$^1$H NMR (600 MHz, CDCl$_3$) δ (ppm): 8.85 (s, 1H), 6.23 (br. s, 1H), 5.96 (br. s, 1H).

Step 3) 4,6-dimethoxypyrimidine-5-carboxamide

To a solution of 4,6-dichloropyrimidine-5-carboxamide (24.6 g, 128 mmol) in methanol (200 mL) was added a solution of sodium methylate (15.2 g, 282 mmol) in MeOH (100 mL). The resulted mixture was stirred at rt for 4.5 hours and concentrated in vacuo. The residue was purified by a silica gel column chromatography (EtOAc/MeOH (v/v)=25/1) to give the title compound as a pale yellow solid (18.3 g, yield: 71.1%).

MS (ESI, pos. ion) mz: 184.1 [M+H]$^+$;
$^1$H NMR (600 MHz, CDCl$_3$) δ (ppm): 8.47 (s, 1H), 6.30 (br. s, 1H), 5.98 (br. s, 1H), 4.07 (s, 6H).

Step 4) N-(1-(dimethylamino)ethylidene)-4,6-dimethoxypyrimidine-5-carboxamide

A mixture of 4,6-dimethoxypyrimidine-5-carboxamide (5.0 g, 27.3 mmol) and 1,1-dimethoxy-N,N-dimethylethanamine (15 mL) was heated to 110° C. and stirred further for 1 hour. The reaction was monitored by TLC (EtOAc). After the reaction was completed, the reaction mixture was concentrated in vacuo to give the title compound as a yellow-brown solid (6.89 g, 100%) which was used in next step without further purification.

Step 5) 5-(4,6-dimethoxypyrimidin-5-yl)-3-methyl-1,2,4-oxadiazole

To a solution of N-(1-(dimethylamino)ethylidene)-4,6-dimethoxypyrimidine-5-carboxamide (6.89 g, 27.31 mmol) in 1,4-dioxane (50 mL) was added a solution of hydroxylamine hydrochloride (2.0 g, 28.7 mmol) and 5 M NaOH aqueous solution (6 mL), followed by adding H$_2$O (14 mL) and AcOH (50 mL). The mixture was heated to 110° C. and stirred further for 1 hour, then cooled to rt, and diluted with H$_2$O (150 mL). The resulted mixture was extracted with EtOAc (150 mL×3). The combined organic phases were washed with brine (100 mL), dried over anhydrous Na$_2$SO$_4$ and concentrated in vacuo. The residue was purified by a silica gel column chromatography (PE/EtOAc (v/v)=10/1) to give the title compound as an off-white solid (5.14 g, yield 84.7% for two steps).

MS (ESI, pos. ion) mz: 223.1 [M+H]+.

Step 6) 5-(4,6-dichloropyrimidin-5-yl)-3-methyl-1,2,4-oxadiazole

To a suspension of 5-(4,6-dimethoxypyrimidin-5-yl)-3-methyl-1,2,4-oxadiazole (5.14 g, 23.1 mmol) in anhydrous toluene (100 mL) was added POCl₃ (21 mL, 231 mmol) and DMF (10 mL). The resulted mixture was heated to reflux and stirred further for 24 hours. The supernatant was separated and concentrated in vacuo to give part of the crude product as yellow oil. The dark brown residue was suspended in H₂O (150 mL) and the resulted mixture was extracted with EtOAc (150 mL). The organic phase was washed with brine (50 mL) and concentrated in vacuo. The two parts of the crude product was combined together and purified by a silica gel column chromatography (PE/EtOAc (v/v)=401) to give the title compound as white powder (4.76 g, yield 89.1%).

MS (ESI, pos. ion): 231.0 [M+H]+;

¹H NMR (400 MHz, CDCl₃) δ (ppm): 8.98 (s, 1H), 2.60 (s, 3H);

¹³C NMR (101 MHz, CDCl₃) δ (ppm): 168.70 (s), 168.16 (s), 161.87 (s), 159.61 (s), 120.81 (s), 11.68 (s).

Step 7) 6-chloro-5-(3-methyl-1,2,4-oxadiazol-5-yl)pyrimidin-4-amine

To a solution of 5-(4,6-dichloropyrimidin-5-yl)-3-methyl-1,2,4-oxadiazole (4.76 g, 20.6 mmol) in THF (100 mL) under NH₃ gas atmosphere was stirred at rt for 1 hour. The reaction was monitored by TLC (PE/EtOAc, v/v, 4/1). The mixture was filtered and the filter cake was washed with EtOAc (20 mL). The filtrate was concentrated in vacuo to give the title compound as a white cotton-like solid (4.22 g, yield: 96.8%).

MS (ESI, pos. ion): 212.0 [M+H]+;

¹H NMR (400 MHz, CDCl₃) δ (ppm): 8.81 (br. s, 1H), 8.43 (s, 1H), 6.16 (br. s, 1H), 2.54 (s, 3H), 1.63 (s, 1H).

Step 8) (S)-3-(1-((6-amino-5-(3-methyl-1,2,4-oxadiazol-5-yl)pyrimidin-4-yl)amino)ethyl)-8-chloro-2-cyclopropylisoquinolin-1(2H)-one A mixture of (S)-3-(1-aminoethyl)-8-chloro-2-cyclopropylisoquinolin-1(2H)-one (30 mg, 0.114 mmol), 6-chloro-5-(3-methyl-1,2,4-oxadiazol-5-yl)pyrimidin-4-amine (24 mg, 0.114 mmol) and DIPEA (29 mg, 0.228 mmol) in n-BuOH (1 mL) was heated to 125° C. and stirred further for 4 hours, then cooled to rt, and concentrated in vacuo. The residue was purified by a silica gel column chromatography (DCM/MeOH (v/v)=1001) to give the title compound as an off-white solid (24 mg, 48%).

MS (ESI, Pos. ion) mz: 438.0 [M+H]+; HPLC: 99%;

¹H NMR (400 MHz, CDCl₃) δ (ppm): 8.45 (s, 1H), 8.12 (s, 1H), 7.38 (m, 3H), 6.40 (s, 1H), 6.08 (m, 1H), 3.00 (m, 1H), 2.49 (s, 3H), 1.64-1.63 (d, J=4.0 Hz, 3H), 1.39 (m, 2H), 1.31 (m, 1H), 0.88 (m, 1H).

Example 25 (S)-3-(1-((6-amino-5-(5-methyl-1,3,4-oxadiazol-2-yl)pyrimidin-4-yl)amino)ethyl)-2-cyclopropyl-8-(1-methyl-1H-pyrazol-4-yl)isoquinolin-1(2H)-one

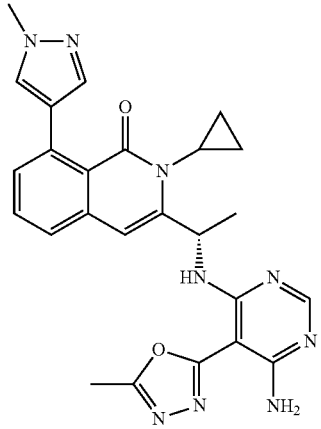 [SMILES: Cc1nnc(-c2c(N)ncnc2N[C@@H](C)c2cc3cccc(-c4cnn(C)c4)c3c(=O)n2C2CC2)o1]

To a solution of (S)-3-(1-((6-amino-5-(5-methyl-1,3,4-oxadiazol-2-yl)pyrimidin-4-yl)amino)ethyl)-8-chloro-2-cyclopropylisoquinolin-1(2H)-one (51 mg, 0.1165 mmol) and 1-methyl-4-(4,4,5,5-tetramethyl-1,3,2-dioxaborolan-2-yl)pyrazole (48 mg, 0.230 mmol) in DMAC/H₂O (0.6 mL/0.3 mL) were added Pd(dppf)Cl₂·CH₂Cl₂ (22 mg, 0.0264 mmol) and Na₂CO₃ (38 mg, 0.3585 mmol) at rt. The reaction was degassed with N₂ three times and heated at 120° C. for 100 minutes. The black solution was cooled to rt, then EtOAc (60 mL) was added. The separated organic layer was washed with H₂O (20 mL×2), dried over anhydrous Na₂SO₄, and concentrated in vacuo. The crude product was purified by a silica gel column chromatography (DCM/MeOH (v/v)=50/1) to give the title compound as a yellow solid (29.6 mg, 52.6%).

MS (ESI, pos. ion) mz: 483.9 [M+H]+;

¹H NMR (600 MHz, DMSO-d₆) δ (ppm): 8.44 (d, J=7.0 Hz, 1H), 8.06 (s, 1H), 7.81 (s, 1H), 7.55 (t, J=7.6 Hz, 1H), 7.51 (s, 1H), 7.42 (d, J=7.8 Hz, 1H), 7.26 (d, J=7.4 Hz, 1H), 7.26 (br s, 2H), 6.55 (s, 1H), 6.06-5.98 (m, 1H), 3.90 (s, 3H), 3.02-2.95 (m, 1H), 2.64 (S, 3H), 2.07-1.99 (m, 1H), 1.64 (d, J=6.7 Hz, 3H), 1.38 (d, J=9.4 Hz, 1H), 1.24-1.17 (m, 2H), 0.91-0.87 (m, 1H), 0.84-0.80 (m, 1H).

Example 26 (S)-3-(1-((6-amino-5-(3-methyl-1,2,4-oxadiazol-5-yl)pyrimidin-4-yl)amino)ethyl)-2-cyclopropyl-8-(1-methyl-1H-pyrazol-4-yl)isoquinolin-1(2H)-one

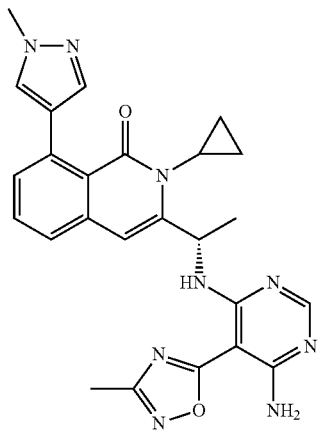 [SMILES: Cc1noc(-c2c(N)ncnc2N[C@@H](C)c2cc3cccc(-c4cnn(C)c4)c3c(=O)n2C2CC2)n1]

Step 1) (S)-tert-butyl(1-(8-chloro-2-cyclopropyl-1-oxo-1,2-dihydroisoquinolin-3-yl)ethyl)carbamate To a solution of (S)-3-(1-aminoethyl)-8-chloro-2-cyclopropylisoquinolin-1(2H)-one (1.00 g, 3.81 mmol) and sodium carbonate (806.7 mg, 50.29 mmol) in THF (6 mL) and water (6 mL) was added di-tert-butyl dicarbonate (1.1 mL) dropwise at rt, the reaction was stirred at rt for 2.5 hours, then diluted with $H_2O$ (20 mL) and EtOAc (25 mL). The separated organic phase was washed with HCl aqueous solution (1M, 12 mL), and saturated brine (25 mL), dried over anhydrous $Na_2SO_4$, and concentrated in vacuo to give the crude product as yellowish solid (1.69 g) which was used for the next step without further purification.

MS (ESI, pos. ion) mz: 362.9 [M+H]$^+$;

$^1$H NMR (400 MHz, CDCl$_3$) δ (ppm): 7.40-7.39 (d, J=4.4 Hz, 2H), 7.30-7.29 (m, 1H), 6.41 (s, 1H), 5.55-5.51 (m, 1H), 4.88-4.87 (d, J=6.0 Hz, 1H), 2.96-2.91 (m, 1H), 1.48-1.47 (d, J=7.2 Hz, 3H), 1.45 (s, 9H), 1.37-1.30 (m, 2H), 1.10 (m, 1H), 0.87-0.81 (m, 1H).

Step 2) (S)-tert-butyl(1-(2-cyclopropyl-8-(1-methyl-1H-pyrazol-4-yl)-1-oxo-1,2-dihydroisoquinolin-3-yl)ethyl)carbamate A mixture of (S)-tert-butyl(1-(8-chloro-2-cyclopropyl-1-oxo-1,2-dihydroisoquinolin-3-yl)ethyl)carbamate (1.69 g, 4.66 mmol), 1-methyl-4-(4,4,5,5-tetramethyl-1,3,2-dioxaborolan-2-yl)pyrazole (1.46 g, 7.02 mmol) and sodium carbonate (990 mg, 9.34 mmol) in water (7 mL) and N,N-dimethylacetamide (7 mL) was heated to 120° C. and stirred further for 3.5 hours, then cooled to rt, and diluted with $H_2O$ (60 mL) and EtOAc (60 mL). The separated organic phase was washed with $H_2O$ (60 mL), and saturated brine (60 mL), and concentrated in vacuo. The residue was purified by a silica gel column chromatography (PE/EtOAc (v/v)=16) to give the title compound as a yellowish solid (1.4 g, 90.3% for two steps).

MS (ESI, pos. ion) mz: 408.9 [M+H]$^+$;

$^1$H NMR (400 MHz, CDCl$_3$) δ (ppm): 7.60 (s, 1H), 7.57 (s, 1H), 7.51-7.47 (dd, J=7.6, 7.6 Hz, 1H), 7.34-7.32 (d, J=7.6 Hz, 1H), 7.28-7.26 (d, J=8.0 Hz, 1H), 6.44 (s, 1H), 5.54-5.51 (m, 1H), 4.79-4.77 (d, J=6.4 Hz, 1H), 3.96 (s, 3H), 2.91-2.85 (m, 1H), 1.48-1.46 (d, J=6.8 Hz, 3H), 1.44 (s, 9H), 1.28-1.25 (m, 2H), 1.04 (m, 1H), 0.78-0.73 (m, 1H).

Step 3) (S)-3-(1-aminoethyl)-2-cyclopropyl-8-(1-methyl-1H-pyrazol-4-yl) isoquinolin-1(2H)-one To a solution of (S)-tert-butyl(1-(2-cyclopropyl-8-(1-methyl-1H-pyrazol-4-yl)-1-oxo-1,2-dihydroisoquinolin-3-yl)ethyl)carbamate (1.40 g, 3.43 mmol) in dichloromethane (4 mL) was added a solution of hydrogen chloride in EtOAc (3 M, 20 mL), the mixture was stirred at rt for 2 days, then concentrated in vacuo. The residue was dissolved in $H_2O$ (30 mL), and the resulted mixture was extracted with EtOAc (20 mL×2). The aqueous layer was basified to pH=8.5 with NaHCO$_3$ powder, and extracted with DCM (30 mL×2). The combined organic phases was washed with saturated brine (30 mL), dried over anhydrous $Na_2SO_4$, and concentrated in vacuo to give the title compound as a white solid (800 mg, 75.7%).

$^1$H NMR (400 MHz, CDCl$_3$) δ (ppm): 7.61 (s, 1H), 7.58 (s, 1H), 7.52-7.48 (d, J=7.6, 7.6 Hz, 1H), 7.37-7.35 (d, J=8.0 Hz, 1H), 7.27-7.26 (m, 1H), 6.60 (s, 1H), 4.79 (q, J=6.4 Hz, 1H), 3.96 (s, 3H), 2.93-2.88 (m, 1H), 1.46-1.44 (d, J=6.5 Hz, 3H), 1.30-1.22 (m, 2H), 0.80-0.77 (m, 2H).

Step 4) (S)-3-(1-((6-amino-5-(3-methyl-1,2,4-oxadiazol-5-yl)pyrimidin-4-yl)amino)ethyl)-2-cyclopropyl-8-(1-methyl-1H-pyrazol-4-yl)isoquinolin-1(2H)-one To a solution of (S)-3-(1-aminoethyl)-2-cyclopropyl-8-(1-methyl-1H-pyrazol-4-yl) isoquinolin-1(2H)-one (40 mg, 0.1297 mmol) in butan-1-ol (0.5 mL) and N-ethyl-N-isopropyl-propan-2-amine (0.1 mL) was added 6-chloro-5-(3-methyl-1,2,4-oxadiazol-5-yl)pyrimidin-4-amine (30 mg, 0.14 mmol) at rt. The reaction was heated to 100° C. and stirred further for 4 hours, then cooled to rt. Water (30 mL) was added to the reaction, and the resulted mixture was extracted with DCM (20 mL×3). The combined organic layers were dried over anhydrous $Na_2SO_4$, and concentrated in vacuo. The residue was purified by a silica gel column chromatography (DCM/MeOH (v/v)=30/1) to give the title compound as a yellow solid (46.6 mg, 74%).

MS (ESI, pos. ion) mz: 483.8 [M+H]$^+$;

$^1$H NMR (400 MHz, CDCl$_3$) δ (ppm): 8.45 (d, J=6.8 Hz, 1H), 8.13 (s, 1H), 7.61 (s, 1H), 7.58 (s, 1H), 7.47 (t, J=7.7 Hz, 1H), 7.30 (s, 1H), 6.43 (s, 1H), 6.19-6.09 (m, 1H), 3.96 (s, 3H), 3.01-2.90 (m, 1H), 2.49 (s, 3H), 1.65 (d, J=6.8 Hz, 3H), 1.36-1.30 (m, 2H), 0.89-0.81 (m, 2H).

Example 27 (S)-3-(1-(((6-amino-5-(5-methyl-1,3,4-oxadiazol-2-yl)pyrimidin-4-yl)amino)ethyl)-8-(1-methyl-1H-pyrazol-4-yl)-2-phenylisoquinolin-1(2H)-one

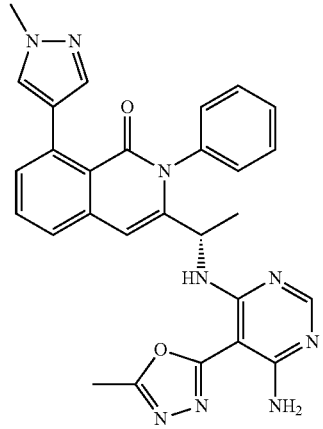 [SMILES: Cc1nnc(-c2c(N)ncnc2N[C@@H](C)c2cc3cccc(-c4cnn(C)c4)c3c(=O)n2-c2ccccc2)o1]

To a solution of (S)-3-(1-(((6-amino-5-(5-methyl-1,3,4-oxadiazol-2-yl)pyrimidin-4-yl)amino)ethyl)-8-chloro-2-phenylisoquinolin-1(2H)-one (144 mg, 0.30 mmol) and 1-methyl-4-(4,4, 5,5-tetramethyl-1,3,2-dioxaborolan-2-yl) pyrazole (124 mg, 0.60 mmol) in N,N-dimethylacetamide (3 mL) and water (1 mL) was added sodium carbonate (102 mg, 0.96235 mmol) and Pd(dppf)Cl$_2$.CH$_2$Cl$_2$ (47 mg, 0.0564 mmol) at rt. The reaction was degassed with N$_2$ for three times, then heated to 120° C. and stirred further for 3 hours. H$_2$O (30 mL) was added to the mixture, and the aqueous layer was extracted with DCM (20 mL×3). The combined organic layers was dried over anhydrous Na$_2$SO$_4$, and concentrated in vacuo. The residue was purified by a silica gel column chromatography (DCM/MeOH (v/v)=30/1) to give the title compound as a yellow solid (28 mg, 18%).

MS (ESI, pos. ion) mz: 520.3 [M+H]⁺;

¹H NMR (600 MHz, CDCl₃) δ (ppm): 8.60 (d, J=7.0 Hz, 1H), 8.00 (s, 1H), 7.59 (s, 1H), 7.57 (s, 1H), 7.54 (t, J=7.7 Hz, 1H), 7.50-7.46 (m, 1H), 7.44-7.41 (m, 1H), 7.40-7.37 (m, 2H), 7.31-7.28 (m, 2H), 6.58 (s, 1H), 4.99-4.95 (m, 1H), 3.86 (s, 3H), 2.68 (s, 3H), 1.46 (d, J=6.8 Hz, 3H).

Example 28 (S)-3-(1-(((6-amino-5-(3-methyl-1,2,4-oxadiazol-5-yl)pyrimidin-4-yl)amino)ethyl)-8-(1-methyl-1H-pyrazol-4-yl)-2-phenylisoquinolin-1(2H)-one

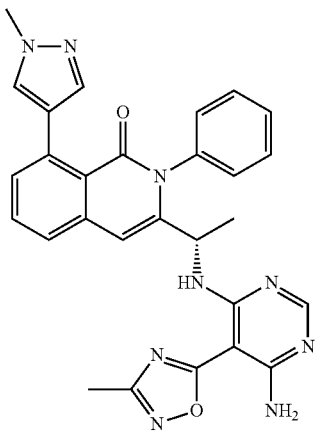 [SMILES: Cc1noc(-c2c(N)ncnc2N[C@@H](C)c2cc3cccc(-c4cnn(C)c4)c3c(=O)n2-c2ccccc2)n1]

Step 1) (S)-tert-butyl(1-(8-chloro-1-oxo-2-phenyl-1,2-dihydroisoquinolin-3-yl)ethyl) carbamate To a solution of (S)-3-(1-aminoethyl)-8-chloro-2-phenylisoquinolin-1(2H)-one (201 mg, 0.6727 mmol) in DCM (8 mL) was added N,N-diethylethanamine (0.28 mL, 2.0 mmol) and di-tert-butyl dicarbonate (0.23 mL, 1.0 mmol) at rt. The reaction was stirred at rt for 3.5 hours, then H₂O (20 mL) was added, and the aqueous layer was extracted with DCM (10 mL×3). The combined organic layers were dried over anhydrous Na₂SO₄, and concentrated in vacuo. The residue was purified by a silica gel column chromatography (DCM/MeOH (v/v)=20/1) to give the title compound as a white solid (262 mg, 98%).

MS (ESI, pos. ion) mz: 399.9 [M+H]⁺;

¹H NMR (400 MHz, CDCl₃) δ (ppm): 7.56-7.39 (m, 6H), 7.31-7.26 (m, 2H), 6.54 (s, 1H), 4.67 (brs, 1H), 4.38 (br s, 1H), 1.40 (s, 9H), 1.24 (d, J=6.8 Hz, 3H).

Step 2) (S)-tert-butyl(1-(8-(1-methyl-1H-pyrazol-4-yl)-1-oxo-2-phenyl-1,2-dihydroisoquinolin-3-yl)ethyl)carbamate To a solution of (S)-tert-butyl (1-(8-chloro-1-oxo-2-phenyl-1,2-dihydroisoquinolin-3-yl)ethyl)carbamate (270 mg, 0.6769 mmol) and 1-methyl-4-(4,4,5,5-tetramethyl-1,3,2-dioxaborolan-2-yl)pyrazole (283 mg, 1.360 mmol) in N,N-dimethylacetamide (4 mL) and water (2 mL) was added sodium carbonate (210 mg, 1.98 mmol) and Pd(dppf)Cl₂.CH₂Cl₂ (95 mg, 0.114 mmol, 98.0 mass %) at rt. The reaction was degassed with N₂ for three times, then heated to 120° C. and stirred further for 2 hours. H₂O (30 mL) was added to the mixture, and the aqueous layer was extracted with DCM (20 mL×3). The combined organic layers was dried with anhydrous Na₂SO₄, and concentrated in vacuo.

The residue was purified by a silica gel column chromatography (DCM/MeOH (v/v)=30/1) to give the title compound as a yellow solid (285 mg, 95%).

MS (ESI, pos. ion) mz: 445.9 [M+H]⁺.

Step 3) (S)-3-(1-aminoethyl)-8-(1-methyl-1H-pyrazol-4-yl)-2-phenylisoquinolin-1(2H)-one To a mixture of (S)-tert-butyl(1-(8-(1-methyl-1H-pyrazol-4-yl)-1-oxo-2-phenyl-1,2-dihydroisoquinolin-3-yl)ethyl) carbamate (280 mg, 0.63 mmol) in DCM (1 mL) was added a solution of HCl in EtOAc (3M, 3 mL) at rt. The reaction was stirred at rt for 3 hours, then saturated NaHCO₃ (20 mL) aqueous solution was added to the mixture, and the aqueous layer was extracted with EtOAc (20 mL×7). The combined organic layers were dried over anhydrous Na₂SO₄, and concentrated in vacuo. The residue was purified by a silica gel column chromatography (DCM/MeOH (v/v)=20/1) to give the title compound as a yellow solid (96 mg, 44.3%).

MS (ESI, pos. ion) mz: 345.0 [M+H]⁺;

¹H NMR (600 MHz, CDCl₃) δ (ppm): 7.61-7.56 (m, 3H), 7.55-7.41 (m, 5H), 7.32 (dd, J=7.5, 1.2 Hz, 1H), 7.25-7.23 (m, 1H), 6.73 (s, 1H), 3.87 (s, 3H), 3.66 (q, J=6.5 Hz, 1H), 1.27 (d, J=6.5 Hz, 3H).

Step 4) (S)-3-(1-((6-amino-5-(3-methyl-1,2,4-oxadiazol-5-yl)pyrimidin-4-yl)amino)ethyl)-8-(1-methyl-1H-pyrazol-4-yl)-2-phenylisoquinolin-1(2H)-one To a solution of (S)-3-(1-aminoethyl)-8-(1-methyl-1H-pyrazol-4-yl)-2-phenylisoquinolin-1(2H)-one (95 mg, 0.276 mmol) in N-ethyl-N-isopropyl-propan-2-amine (0.2 mL) and butan-1-ol (1.5 mL) was added 6-chloro-5-(3-methyl-1,2,4-oxadiazol-5-yl)pyrimidin-4-amine (85 mg, 0.402 mmol) at rt. The mixture was heated to 100° C. and stirred further for 1 hours, then H₂O (30 mL) was added to the mixture, and the aqueous layer was extracted with DCM (20 mL×3). The combined organic layers was dried over anhydrous Na₂SO₄, and concentrated in vacuo. The residue was purified by a silica gel column chromatography (DCM/MeOH (v/v)=30/1) to give the title compound as a white solid (112 mg, 78%).

MS (ESI, pos. ion) mz: 520.8 [M+H]⁺;

¹H NMR (400 MHz, CDCl₃) δ (ppm): 8.23 (d, J=6.9 Hz, 1H), 8.00 (s, 1H), 7.59 (s, 1H), 7.57 (s, 1H), 7.56-7.53 (m, 1H), 7.51-7.45 (m, 1H), 7.43-7.34 (m, 4H), 7.34-7.27 (m, 2H), 6.57 (s, 1H), 5.04-4.93 (m, 1H), 4.72 (br s, 2H), 3.86 (s, 3H), 2.49 (s, 3H), 1.46 (d, J=6.8 Hz, 3H).

Biological Testing

The LC/MS/MS system used in the analysis consists of an Agilent 1200 Series vacuum degasser, binary pump, wellplate autosampler, thermostatted column compartment, the Agilent G6430 Triple Quadrupole Mass Spectrometer with an electrosprayionization (ESI) source. Quantitative analysis was carried out using MRM mode. The parameters for MRM transitions are in the Table A.

TABLE A

| MRM | 490.2→383.1 |
|---|---|
| Fragmentor | 230 V |
| CE | 55 V |
| Drying Gas Temp | 350° C. |
| Nebulize | 40 psi |
| Drying Gas Flow | 10 L/min |

An Agilent XDB-C18, 2.1×30 mm, 3.5 μM column was used for the analysis. 5 μL of the samples were injected.

Analysis condition: The mobile phase was 0.1% formic acid in water (A) and 0.1% formic acid in methanol (B). The flow rate was 0.4 mL/min. And the gradient of Mobile phase was in the Table B.

TABLE B

| Time | Gradient of Mobile Phase B |
|---|---|
| 0.5 min | 5% |
| 1.0 min | 95% |
| 2.2 min | 95% |
| 2.3 min | 5% |
| 5.0 min | stop |

Alternatively, an Agilent 6330 series LC/MS/MS spectrometer equipped with G1312A binary pumps, a G1367A autosampler and a G1314C UV detector were used in the analysis. An ESI source was used on the LC/MS/MS spectrometer. The analysis was done in positive ion mode as appropriate and the MRM transition for each analyte was optimized using standard solution. A Capcell MP-C18 100× 4.6 mm I.D., 5 µM column (Phenomenex, Torrance, Calif., USA) was used during the analysis. The mobile phase was 5 mM ammonia acetate, 0.1% MeOH in water (A): 5 mM ammonia acetate, 0.1% MeOH in acetonitrile (B) (70:30, v/v). The flow rate was 0.6 mL/min. Column was maintained at ambient temperature. 20 µL of the samples were injected.

Example A: Compound Stability in Human and Rat Liver Microsomes

Human or rat liver microsomes incubations were conducted in duplicate in polypropylene tubes. The typical incubation mixtures consisted of human or rat liver microsomes (0.5 mg protein/mL), compounds of interest (5 µM) and NADPH (1.0 mM) in a total volume of 200 µL potassium phosphate buffer (PBS, 100 mM, pH 7.4). Compounds were dissolved in DMSO and diluted with PBS such that the final concentration of DMSO was 0.05%. The enzymatic reactions were commenced with the addition of protein after a 3-min preincubation and incubated in a water bath open to the air at 37° C. Reactions were terminated at various time points (0, 5, 10, 15, 30, 60 min) by adding equal volume of ice-cold acetonitrile. The samples were stored at −80° C. until LC/MS/MS assays.

The concentrations of compounds in the incubation mixtures of human or rat liver microsomes were determined by a LC/MS/MS method. The ranges of the linearity in the concentration range were determined for each tested compounds.

A parallel incubation was performed using denatured microsomes as the negative control, and reactions were terminated at various time points (0, 15, 60 min) after incubation at 37° C.

Dextromethorphan (70 µM) was selected as the positive control, and reactions were terminated at various time points (0, 5, 10, 15, 30, 60 min) after incubation at 37° C. Both positive and negative control samples were included in each assay to ensure the integrity of the microsomal incubation system.

Data Analysis

The concentrations of compounds in human or rat liver microsome incubations were plotted as a percentage of the relevant zero time point control for each reaction. The in vivo $CL_{int}$ were extrapolated (ref: Naritomi, Y.; Terashita, S.; Kimura, S.; Suzuki, A.; Kagayama, A.; and Sugiyama, Y.; Prediction of human hepatic clearance from in vivo animal experiments and in vitro metabolic studies with liver microsomes from animals and humans. *Drug Metab. Dispos.*, 2001, 29: 1316-1324).

TABLE 2

Human and rat liver microsomes Stability

| | Human | | Rat | |
|---|---|---|---|---|
| Example # | $T_{1/2}$ (min) | $CL_{int}$ (mL/min/kg) | $T_{1/2}$ (min) | $CL_{int}$ (mL/min/kg) |
| Ex. 1 | 10.21 | 243.26 | 11.33 | 219.22 |
| Ex. 2 | 2.07 | 839.77 | 5.94 | 418.13 |
| Ex. 3 | 12.93 | 134.44 | 16.73 | 148.46 |
| Ex. 4 | 20.38 | 85.30 | 24.42 | 101.71 |
| Ex. 5 | 59.61 | 29.16 | 23.10 | 107.52 |
| Ex. 6 | 18.68 | 93.06 | 7.66 | 324.24 |
| Ex. 7 | 11.84 | 146.82 | 9.92 | 250.42 |
| Ex. 8 | 8.88 | 195.76 | 10.86 | 228.70 |
| Ex. 9 | 20.78 | 83.65 | 13.44 | 184.80 |
| Ex. 10 | 20.01 | 86.87 | 14.69 | 169.08 |
| Ex. 11 | 3.19 | 544.93 | 7.83 | 317.20 |
| Ex. 13 | 11.06 | 157.17 | 18.18 | 136.62 |
| Ex. 14 | 7.73 | 224.88 | 19.92 | 124.68 |
| Ex. 15 | 6.06 | 286.85 | 24.87 | 99.87 |
| Ex. 16 | 7.92 | 219.49 | 14.33 | 173.32 |
| Ex. 18 | 7.70 | 225.76 | 7.53 | 329.84 |
| Ex. 20 | 6.93 | 250.91 | 24.85 | 99.95 |
| Ex. 21 | 6.73 | 258.29 | 19.17 | 129.56 |
| Ex. 22 | 12.56 | 138.40 | 9.58 | 259.23 |
| Ex. 23 | 3.63 | 478.74 | 5.45 | 456.06 |
| Ex. 24 | 15.28 | 113.76 | 13.09 | 189.74 |

Example B: Evaluation of Pharmacokinetics after Intravenous and Oral Administration of the Compounds Disclosed Herein in Mice, Rats, Dogs and Monkeys The compounds disclosed herein are assessed in pharmacokinetic studies in mice, rats, dogs or monkeys. The compounds are administered as a water solution, 2% HPMC+1% TWEEN®80 in water solution, 5% DMSO+5% solutol in saline, 4% MC suspension or capsule. For the intravenous administration, the animals are generally given at 1 or 2 mg/kg dose. For the oral (p.o.) dosing, mice and rats are generally given 5 or 10 mg/kg dose, and dogs and monkeys are generally given 10 mg/kg dose. The blood samples (0.3 mL) are drawn at 0.25, 0.5, 1.0, 2.0, 3.0, 4.0, 6.0, 8.0, 12 and 24 h time points or 0.083, 0.25, 0.5, 1.0, 2.0, 4.0, 6.0, 8.0 and 24 h time points and centrifuged at 3,000 or 4000 rpm for 2 to 10 min. The plasma solutions are collected, stored at −20° C. or −70° C. until analyzed by LC/MS/MS as described above.

TABLE 3

Pharmacokinetic profiles in Rats

| | | iv dosing | | | | |
|---|---|---|---|---|---|---|
| Example # | dose (mg/kg) | $T_{1/2}$ (h) | $AUC_{last}$ (ng · h/mL) | Cl/F (L/h/kg) | $V_{ss}$ (L/kg) | F % |
| Ex. 1 | 1 | 0.63 | 178 | 5.58 | 3.99 | 46.34 |
| Ex. 2 | 1 | 1.16 | 215 | 4.74 | 4.42 | 46.57 |
| Ex. 3 | 1 | 0.74 | 131 | 7.68 | 4.96 | 12.71 |
| Ex. 4 | 1 | 0.98 | 498 | 2.00 | 2.40 | 78.78 |
| Ex. 5 | 1 | 0.53 | 320 | 3.13 | 1.87 | 106.3 |
| Ex. 6 | 1 | 0.86 | 266 | 3.74 | 4.08 | 48.66 |
| Ex. 7 | 1 | 2.30 | 307 | 3.26 | 7.96 | 42.95 |
| Ex. 8 | 1 | 0.92 | 291 | 3.47 | 1.94 | 93.06 |

TABLE 3-continued

Pharmacokinetic profiles in Rats iv dosing

| Example # | dose (mg/kg) | $T_{1/2}$ (h) | $AUC_{last}$ (ng · h/mL) | Cl/F (L/h/kg) | $V_{ss}$ (L/kg) | F % |
|---|---|---|---|---|---|---|
| Ex. 9 | 1 | 1.38 | 964 | 1.04 | 1.04 | 66.87 |
| Ex. 10 | 1 | 1.44 | 333 | 3.00 | 5.35 | 81.33 |
| Ex. 12 | 1 | 0.70 | 555 | 1.80 | 1.42 | 32.09 |
| Ex. 13 | 1 | 1.66 | 465 | 2.17 | 4.42 | 67.9 |
| Ex. 15 | 1 | 0.86 | 758 | 1.36 | 0.92 | 48.92 |
| Ex. 16 | 1 | 0.61 | 186 | 5.36 | 2.94 | 11.44 |
| Ex. 18 | 1 | 0.775 | 323 | 3.10 | 1.66 | 38.15 |
| Ex. 20 | 1 | 0.81 | 341 | 2.92 | 2.65 | 64.61 |
| Ex. 22 | 1 | 1.32 | 167 | 5.99 | 6.07 | 16.23 |
| Ex. 24 | 1 | 0.75 | 139 | 7.20 | 5.46 | 12.28 |

TABLE 4

Pharmacokinetic profiles in Dogs and Monkeys iv dosing

| Example # | Species | dose (mg/kg) | $T_{1/2}$ (h) | $AUC_{last}$ (ng · h/mL) | Cl/F (L/h/kg) | $V_{ss}$ (L/kg) | F % |
|---|---|---|---|---|---|---|---|
| Ex. 8 | Dog | 1 | 1.70 | 1350 | 0.73 | 1.43 | 52.85 |
|  | Monkey | 1 | 0.65 | 711 | 1.46 | 1.20 | 13.1 |
| Ex. 9 | Dog | 1 | 1.25 | 695 | 1.42 | 2.04 | 72.99 |
|  | Monkey | 1 | 1.23 | 1120 | 0.89 | 1.17 | 179.7 |

Example C: Kinase Activity Assay

The efficacy of the compounds disclosed herein as inhibitors of PI3 kinases and mTOR kinases can be evaluated as follows.

General Description for Kinase Assays

Kinase assays can be performed by measurement of incorporation of $\gamma$-$^{33}$P ATP into immobilized myelin basic protein (MBP). High binding white 384 well plates (Greiner) are coated with MBP (Sigma #M-1891) by incubation of 60 µL/well of 20 µg/mL MBP in Tris-buffered saline (TBS; 50 mM Tris pH 8.0, 138 mM NaCl, 2.7 mM KCl) for 24 hours at 4° C. Plates are washed 3× with 100 µL TBS. Kinase reactions are carried out in a total volume of 34 µL in kinase buffer (5 mM Hepes pH 7.6, 15 mM NaCl, 0.01% bovine gamma globulin (Sigma #I-5506), 10 mM MgCl$_2$, 1 mM DTT, 0.02% TritonX-100). Compound dilutions are performed in DMSO and added to assay wells to a final DMSO concentration of 1%. Each data point is measured in duplicate, and at least two duplicate assays are performed for each individual compound determination. Enzyme is added to final concentrations of 10 nM or 20 nM, for example. A mixture of unlabeled ATP and $\gamma$-$^{33}$P ATP is added to start the reaction (2×10$^6$ cpm of $\gamma$-$^{33}$P ATP per well (3000 Ci/mmole) and 10 µM unlabeled ATP, typically. The reactions are carried out for 1 h at rt with shaking Plates are washed 7× with TBS, followed by the addition of 50 µL/well scintillation fluid (Wallac). Plates are read using a Wallac Trilux counter. This is only one format of such assays; various other formats are possible, as known to one skilled in the art.

The above assay procedure can be used to determine the IC$_{50}$ for inhibition and/or the inhibition constant, K$_i$. The IC$_{50}$ is defined as the concentration of compound required to reduce the enzyme activity by 50% under the condition of the assay. The IC$_{50}$ value is estimated by preparing a 10 point curve using a ½ log dilution series (for example, a typical curve may be prepared using the following compound concentrations: 10 µM, 3 µM, 1 µM, 0.3 µM, 0.1 µM, 0.03 µM, 0.01 µM, 0.003 µM, 0.001 µM and 0 µM).

PI3 Kinase General Assay Protocol

PI3K (p110α/p85α) (h) [Non-Radioactive Assay]

PI3K (p110α/p85α) (h) is incubated in assay buffer containing 10 µM phosphatidylinositol 4,5-bisphosphate and MgATP (concentration as required). The reaction is initiated by the addition of the ATP solution. After incubation for 30 minutes at room temperature, the reaction is stopped by the addition of stop solution containing EDTA and biotinylated phosphatidylinositol-3,4,5-trisphosphate. Finally, detection buffer is added, which contains europium-labelled anti-GST monoclonal antibody, GST-tagged GRP1 PH domain and streptavidin allophycocyanin. The plate is then read in timeresolved fluorescence mode and the homogenous time-resolved fluorescence (HTRF) signal is determined according to the formula HTRF=10000×(Em665 nm/Em620 nm).

PI3K (p110β/p85α) (h) [Non-Radioactive Assay]

PI3K (p110β/p85α) (h) is incubated in assay buffer containing 10 µM phosphatidylinositol-4,5-bisphosphate and MgATP (concentration as required). The reaction is initiated by the addition of the MgATP mix. After incubation for 30 minutes at room temperature, the reaction is stopped by the addition of stop solution containing EDTA and biotinylated phosphatidylinositol-3,4,5-trisphosphate. Finally, detection buffer is added, which contains europium-labelled anti-GST monoclonal antibody, GST-tagged GRP1 PH domain and streptavidin-allophycocyanin. The plate is then read in timeresolved fluorescence mode and the homogenous time-resolved fluorescence (HTRF) signal is determined according to the formula HTRF=10000×(Em665 nm/Em620 nm).

PI3K (p110δ/p85α) (h) [Non-Radioactive Assay]

PI3K (p110δ/p85α) (h) is incubated in assay buffer containing 10 µM phosphatidylinositol-4,5-bisphosphate and MgATP (concentration as required). The reaction is initiated by the addition of the MgATP mix. After incubation for 30 minutes at room temperature, the reaction is stopped by the addition of stop solution containing EDTA and biotinylated phosphatidylinositol-3,4,5-trisphosphate. Finally, detection buffer is added, which contains europium-labelled anti-GST monoclonal antibody, GST-tagged GRP1 PH domain and streptavidin-allophycocyanin. The plate is then read in timeresolved fluorescence mode and the homogenous time-resolved fluorescence (HTRF) signal is determined according to the formula HTRF=10000×(Em665 nm/Em620 nm).

PI3K (p120γ) (h) [Non-Radioactive Assay]

PI3K (p120γ) (h) is incubated in assay buffer containing 10 µM phosphatidylinositol-4,5-bisphosphate and MgATP (concentration as required). The reaction is initiated by the addition of the MgATP mix. After incubation for 30 minutes at room temperature, the reaction is stopped by the addition of stop solution containing EDTA and biotinylated phosphatidylinositol-3,4,5-trisphosphate. Finally, detection buffer is added, which contains europium-labelled anti-GST monoclonal antibody, GST-tagged GRP1 PH domain and streptavidin-allophycocyanin. The plate is then read in timeresolved fluorescence mode and the homogenous time-resolved fluorescence (HTRF) signal is determined according to the formula HTRF=10000×(Em665 nm/Em620 nm).

mTOR (h)

mTOR (h) is incubated with 50 mM HEPES pH 7.5, 1 mM EDTA, 0.01% TWEEN®20, 2 mg/mL substrate, 3 mM Manganese Chloride and [γ-33P-ATP] (specific activity approx. 500 cpm/pmol, concentration as required). The reaction is initiated by the addition of the MnATP mix. After incubation for 40 minutes at room temperature, the reaction is stopped by the addition of 3% phosphoric acid solution. 10 μL of the reaction is then spotted onto a P30 filtermat and washed three times for 5 minutes in 75 mM phosphoric acid and once in methanol prior to drying and scintillation counting.

The kinase assays described herein were performed at Millipore UK Ltd, Dundee Technology Park, Dundee DD2 1 SW, UK.

TABLE 5

Kinase inhibition data

| Example # | IC$_{50}$ (nM) PI3K (h) | | | |
|---|---|---|---|---|
| | p110α/p85α | p110β/p85α | p110δ/p85α | p120γ |
| Ex. 1 | NT | NT | 5 | NT |
| Ex. 2 | NT | NT | 2 | NT |
| Ex. 3 | NT | NT | 2 | NT |
| Ex. 4 | 1472 | 30 | 11 | 387 |
| Ex. 5 | >3000 | 259 | 6 | 388 |
| Ex. 6 | NT | NT | 18 | NT |
| Ex. 7 | NT | NT | 4 | NT |
| Ex. 8 | 276 | 33 | 1 | 74 |
| Ex. 9 | 2678 | 226 | 4 | 255 |
| Ex. 11 | 1482 | 102 | 13 | 375 |
| Ex. 12 | NT | NT | 12 | NT |
| Ex. 16 | NT | NT | 190 | NT |
| Ex. 18 | NT | NT | 32 | NT |
| Ex. 19 | NT | NT | 46 | NT |
| Ex. 21 | NT | NT | 15 | NT |
| Ex. 22 | NT | NT | 3 | NT |
| Ex. 23 | NT | NT | 3 | NT |
| Ex. 24 | 307 | 38 | 3 | 15 |

NT: Not tested

Alternatively, the kinase activities of the compounds can be measured using KINOMEscan™, which is based on a competition binding assay that quantitatively measures the ability of a compound to compete with an immobilized, active-site directed ligand. The assay was performed by combining three components: DNA-tagged kinase; immobilized ligand; and a test compound. The ability of the test compound to compete with the immobilized ligand was measured via quantitative PCR of the DNA tag.

For most assays, kinase-tagged T7 phage strains were prepared in an E. coli host derived from the BL21 strain. E. coli were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SEABLOCK™ (Pierce), 1% BSA, 0.05% TWEEN®20, 1 mM DTT) to remove unbound ligand and to reduce nonspecific binding. Binding reactions were assembled by combining kinases, liganded affinity beads, and test compounds in 1× binding buffer (20% SEA-BLOCK™, 0.17×PBS, 0.05% TWEEN®20, 6 mM DTT). All reactions were performed in polystyrene 96-well plates in a final volume of 0.135 mL. The assay plates were incubated at room temperature with shaking for 1 hour and the affinity beads were washed with wash buffer (1x PBS, 0.05% TWEEN®20). The beads were then re-suspended in elution buffer (1x PBS, 0.05% TWEEN®20, 0.5 μM non-biotinylated affinity ligand) and incubated at room temperature with shaking for 30 minutes. The kinase concentration in the eluates was measured by qPCR.

The kinase assays described herein were performed using KINOMEscan™ Profiling Service at DiscoveRx Corporation, 42501 Albrae St. Fremont, Calif. 94538, USA.

Finally, it should be noted that there are alternative ways of implementing the present invention. Accordingly, the present embodiments are to be considered as illustrative and not restrictive and the invention is not be limited to the details given herein, but may be modified within the scope and equivalents of the appended claims. All publications and patents cited herein are incorporated by reference.

What is claimed is:

1. A compound having Formula (I):

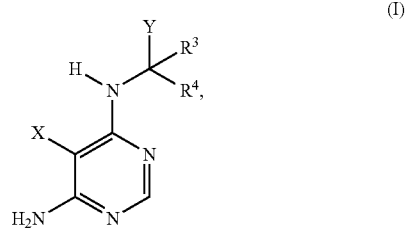

or a stereoisomer, a geometric isomer, a tautomer, an N-oxide, or a pharmaceutically acceptable salt thereof, wherein:
X is 5 membered heteroaryl, wherein X is optionally substituted by 1, 2, 3, 4 or 5 $R^1$ groups;
Y is

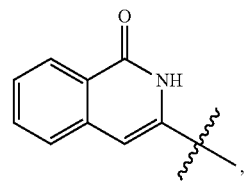

wherein Y is optionally substituted by 1, 2, 3, or 4 $R^2$ groups;
each $R^1$ is independently F, Cl, —C(=O)O$R^a$, —(C$_1$-C$_2$)alkylene-O$R^a$, (C$_1$-C$_4$) alkyl, or cyclopropyl;
each $R^2$ is independently F, Cl, Br, (C$_1$-C$_3$) alkyl, or cyclopropyl, phenyl, or 5 membered heteroaryl, wherein each of the phenyl and 5 membered heteroaryl is optionally substituted with 1, 2, 3 or 4 substitutents independently selected from F, Cl, Br, and (C$_1$-C$_3$) alkyl;
each of $R^3$ and $R^4$ is independently H or (C$_1$-C$_3$)alkyl; and
each $R^a$ is independently H, or (C$_1$-C$_6$)alkyl.

2. The compound according to claim 1, wherein X is a monovalent heteroaryl group derived from one of the following structures:

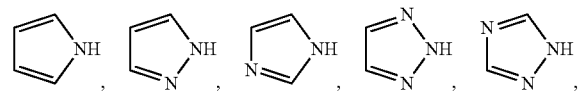

-continued
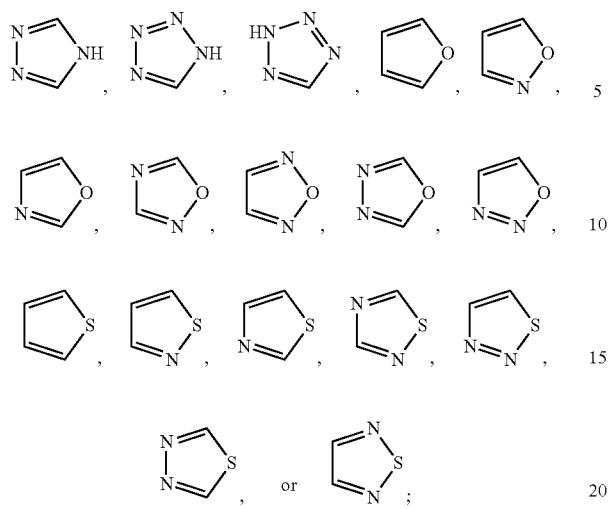
and wherein X is optionally substituted by 1, 2 or 3 R¹ groups.
3. The compound according to claim 1, wherein Y is
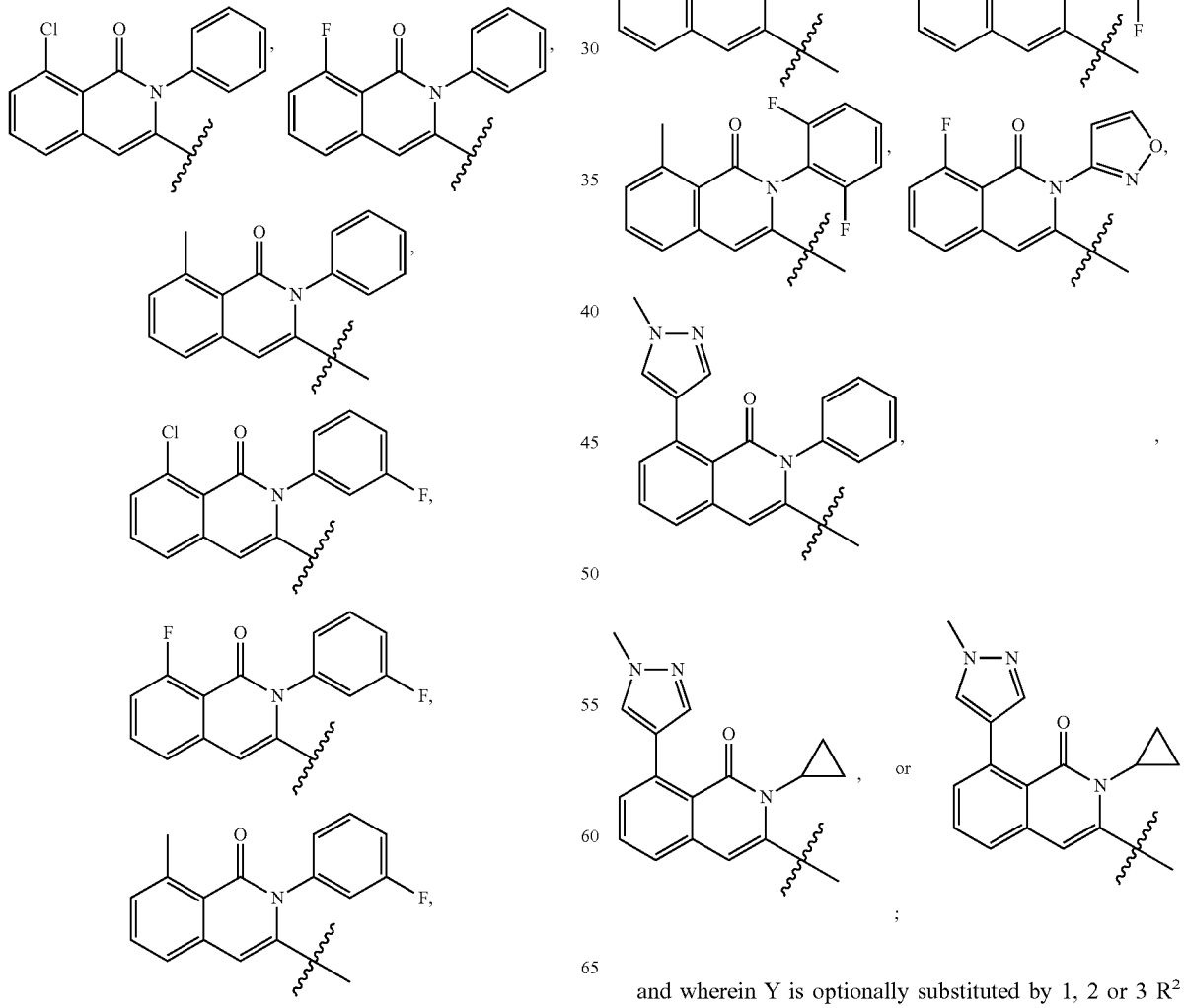
and wherein Y is optionally substituted by 1, 2 or 3 R² groups.

4. A compound having one of the following structures:
(1)
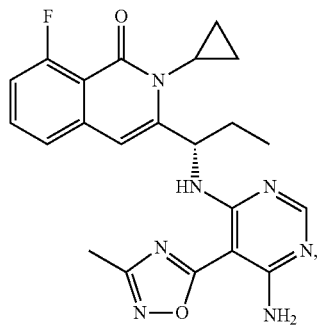
(2)
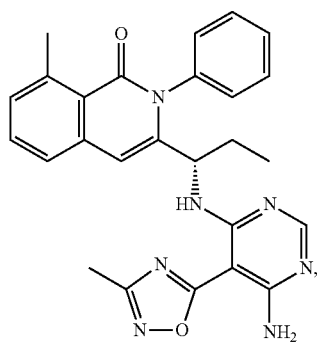
(3)
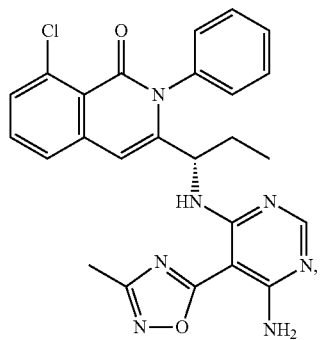
(4)
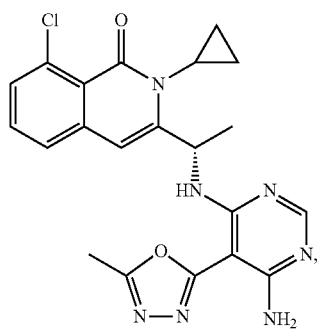
-continued
(5)
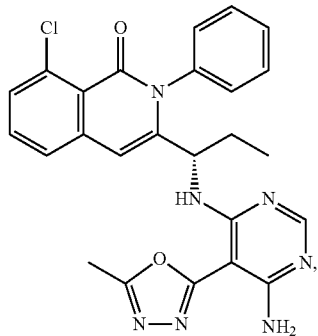
(6)
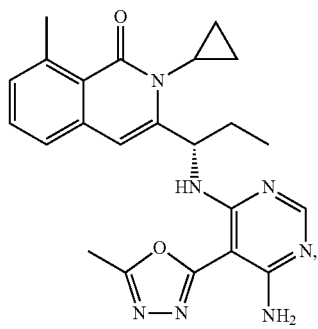
(7)
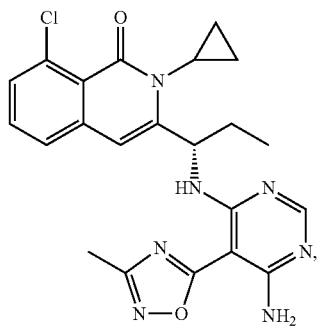
(8)
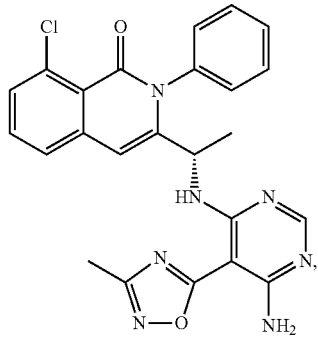

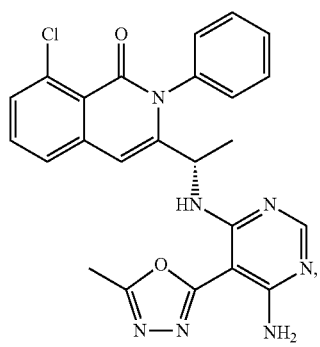
(9)
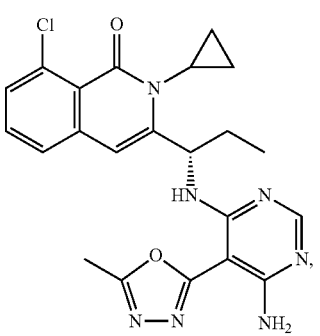
(10)
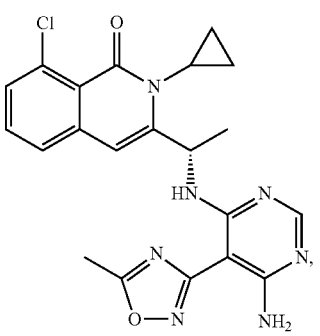
(11)
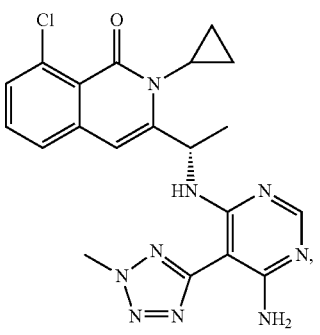
(12)
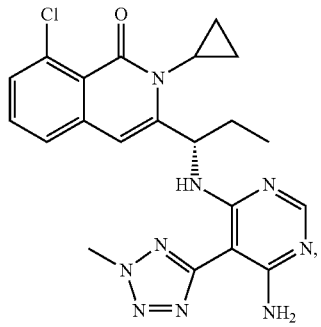
(13)
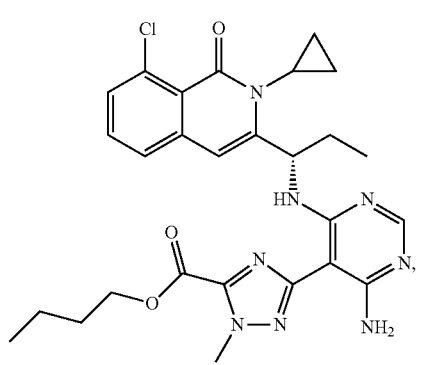
(14)
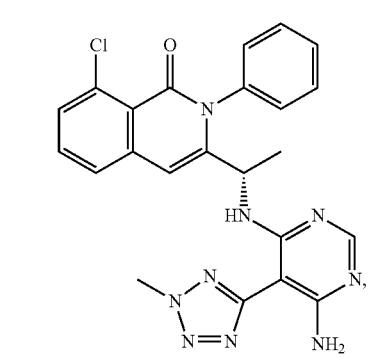
(15)
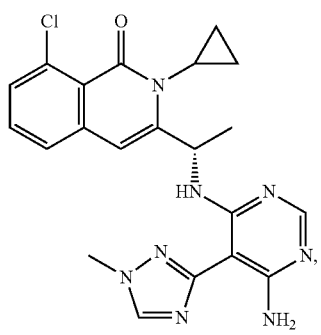
(16)

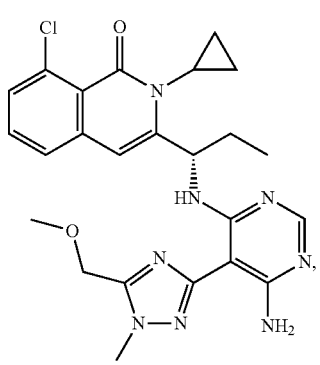 (17)
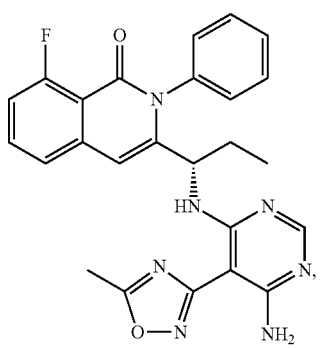 (18)
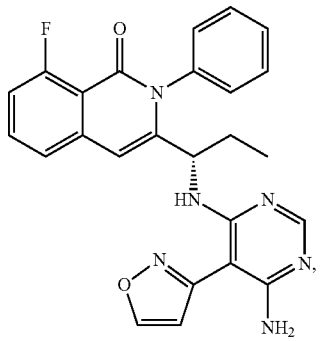 (19)
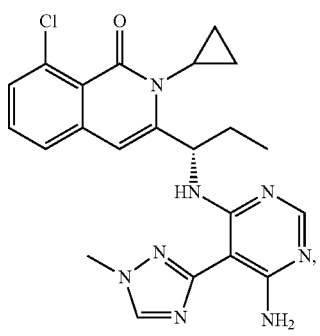 (20)
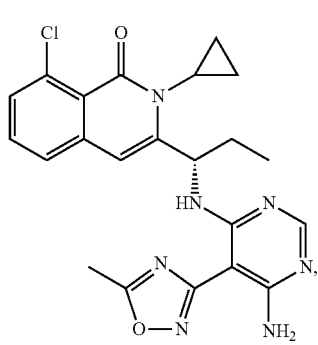 (21)
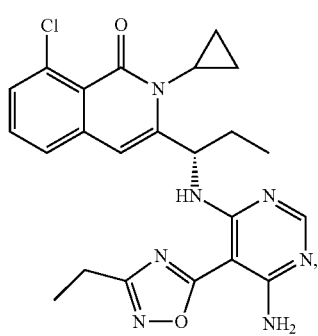 (22)
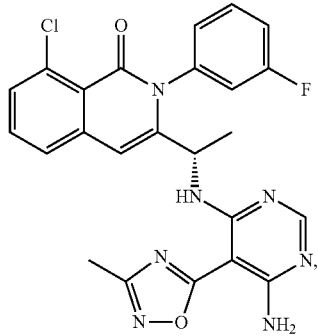 (23)
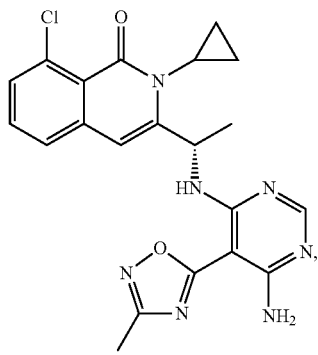 (24)

(25)
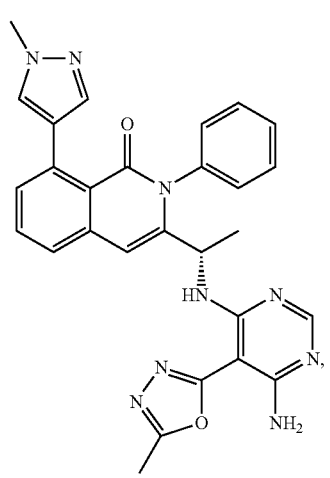
(28)
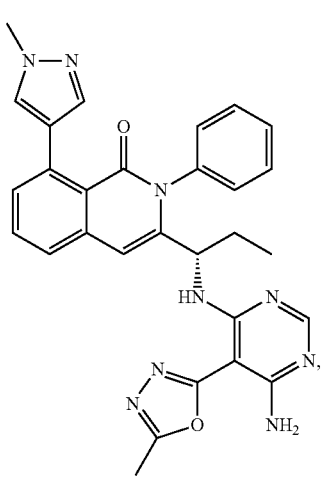
(26)
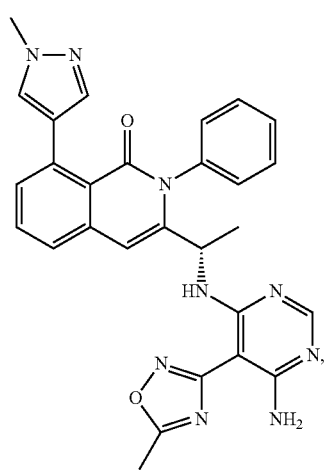
(29)
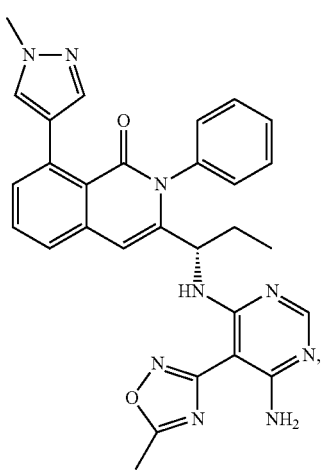
(27)
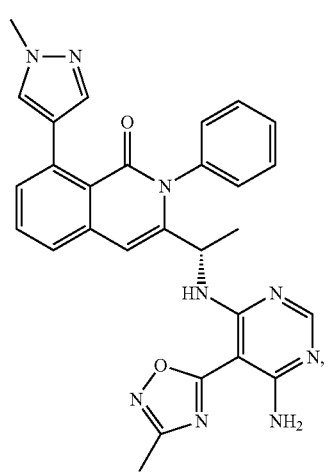
(30)
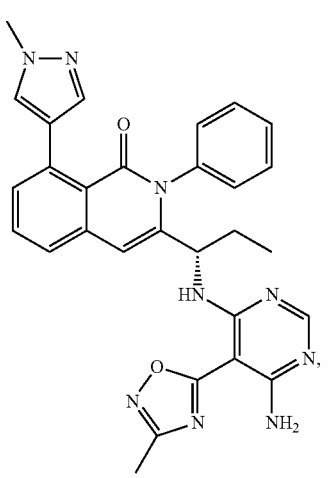

(31)
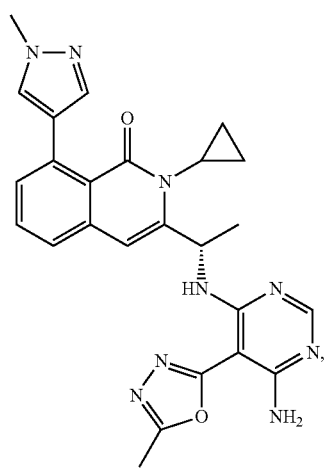
(32)
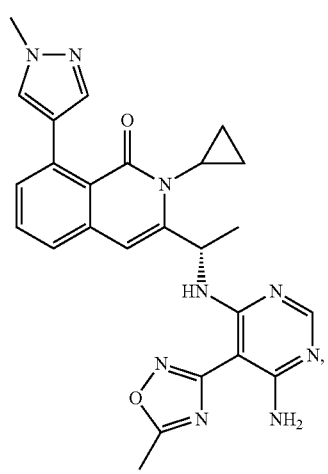
(33)
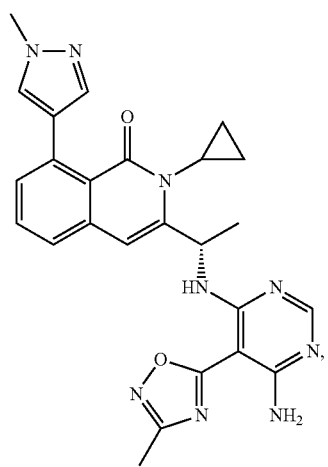
(34)
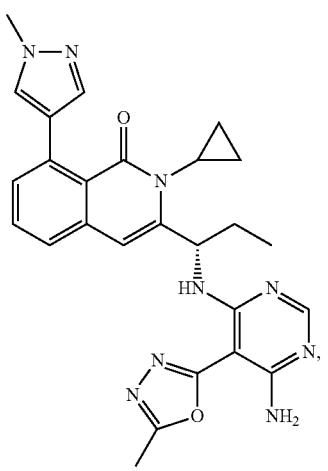
(35)
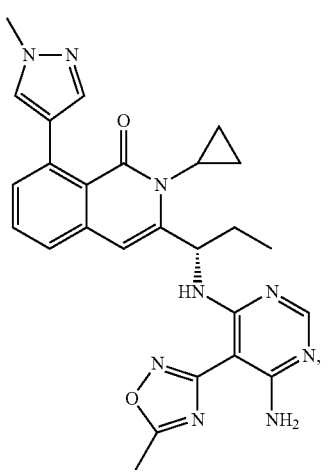
(36)
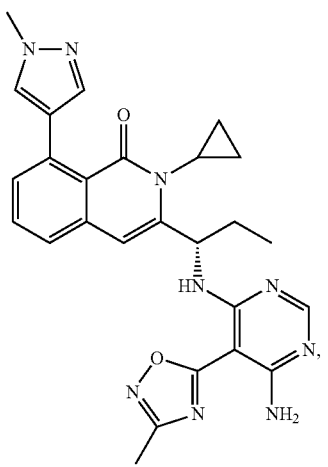

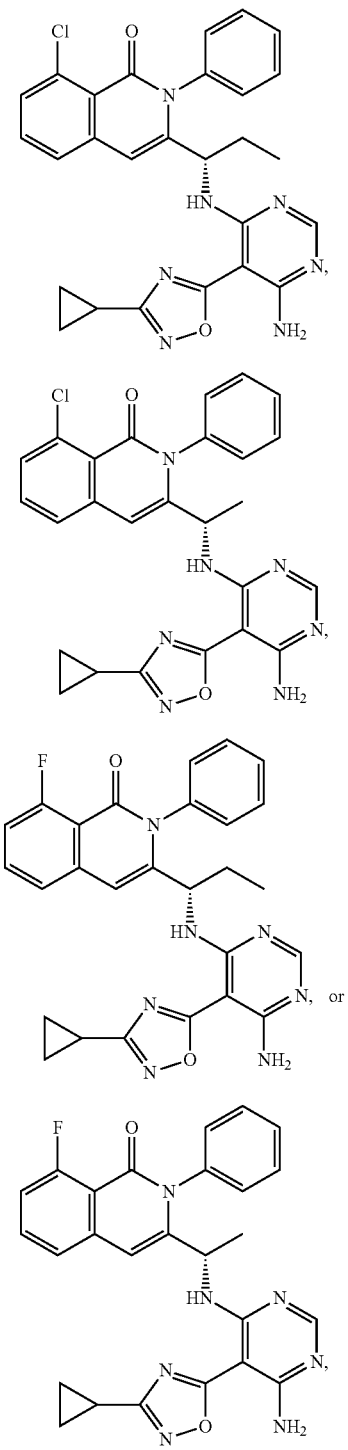

or a stereoisomer, a geometric isomer, a tautomer, an N-oxide, or a pharmaceutically acceptable salt thereof.

5. A pharmaceutical composition comprising the compound according to claim 1, and one or more pharmaceutically acceptable carriers, excipients, diluents, adjuvants, vehicles or a combination thereof.

6. The pharmaceutical composition according to claim 5 further comprising one or more therapeutic agents.

7. A method of treating a disorder mediated by inappropriate PI3-kinase activity comprising administering a therapeutically effective amount of the compound according to claim 1, to a patient in need thereof, wherein the disorder is hematologic malignancy.

8. A method of treating a disorder mediated by inappropriate PI3-kinase activity comprising administering the pharmaceutical composition according to claim 5, to a patient in need thereof, wherein the disorder is hematologic malignancy.

9. A method of modulating the activity of the PI3-kinase, in a subject, wherein the method comprises administering to the subject a therapeutically effective amount of the compound according to claim 1.

10. The method of claim 9, wherein the PI3-kinase is PI3Kδ.

11. A method of modulating the activity of the PI3-kinase, in a subject, wherein the method comprises administering to the subject a therapeutically effective amount of the pharmaceutical composition according to claim 5.

12. The method of claim 11, wherein the PI3-kinase is PI3Kδ.

13. A pharmaceutical composition comprising the compound according to claim 4, and one or more pharmaceutically acceptable carriers, excipients, diluents, adjuvants, vehicles or a combination thereof.

14. The pharmaceutical composition according to claim 13 further comprising one or more therapeutic agents.

15. A method of treating a disorder mediated by inappropriate PI3-kinase activity comprising administering a therapeutically effective amount of the compound according to claim 4, to a patient in need thereof, wherein the disorder is hematologic malignancy.

16. A method of treating a disorder mediated by inappropriate PI3-kinase activity comprising administering the pharmaceutical composition according to claim 13, to a patient in need thereof, wherein the disorder is hematologic malignancy.

* * * * *